US007585493B2

(12) United States Patent
Hale et al.

(10) Patent No.: US 7,585,493 B2
(45) Date of Patent: *Sep. 8, 2009

(54) THIN-FILM DRUG DELIVERY ARTICLE AND METHOD OF USE

(75) Inventors: Ron L. Hale, Woodside, CA (US); Amy Lu, Los Altos, CA (US); Daniel J. Myers, Mountain View, CA (US); Joshua D. Rabinowitz, Mountain View, CA (US); Martin J. Wensley, San Francisco, CA (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 995 days.

This patent is subject to a terminal disclaimer.

(21) Appl. No.: 10/633,877

(22) Filed: Aug. 4, 2003

(65) Prior Publication Data

US 2007/0031340 A1     Feb. 8, 2007

Related U.S. Application Data

(63) Continuation-in-part of application No. 10/322,227, filed on Dec. 17, 2002, now abandoned, application No. 10/633,877, which is a continuation-in-part of application No. 10/280,315, filed on Oct. 25, 2002, now abandoned, application No. 10/633,877, which is a continuation-in-part of application No. 10/302,614, filed on Nov. 21, 2002, application No. 10/633,877, which is a continuation-in-part of application No. 10/302,010, filed on Nov. 21, 2002, now Pat. No. 7,078,016, application No. 10/633,877, which is a continuation-in-part of application No. 10/154,594, filed on May 23, 2002, now Pat. No. 6,740,309, application No. 10/633,877, which is a continuation-in-part of application No. 10/154,765, filed on May 23, 2002, now Pat. No. 6,814,955, application No. 10/633,877, which is a continuation-in-part of application No. 10/155,097, filed on May 23, 2002, now Pat. No. 6,716,417, application No. 10/633,877, which is a continuation-in-part of application No. 10/155,373, filed on May 22, 2002, now Pat. No. 6,737,043, application No. 10/633,877, which is a continuation-in-part of application No. 10/155,621, filed on May 22, 2002, now Pat. No. 6,759,029, application No. 10/633,877, which is a continuation-in-part of application No. 10/155,703, filed on May 22, 2002, now Pat. No. 6,803,031, application No. 10/633,877, which is a continuation-in-part of application No. 10/155,705, filed on May 22, 2002, now Pat. No. 6,805,854, application No. 10/633,877, which is a continuation-in-part of (Continued)

(60) Provisional application No. 60/294,203, filed on May 24, 2001, provisional application No. 60/296,225, filed on Jun. 5, 2001, provisional application No. 60/317,479, filed on Sep. 5, 2001, provisional application No. 60/336,218, filed on Oct. 30, 2001, provisional application No. 60/335,049, filed on Oct. 30, 2001, provisional application No. 60/345,882, filed on Nov. 9, 2001, provisional application No. 60/345,145, filed on Nov. 9, 2001, provisional application No. 60/345,876, filed on Nov. 9, 2001, provisional application No. 60/332,280, filed on Nov. 21, 2001, provisional application No. 60/332,279, filed on Nov. 21, 2001, provisional application No. 60/332,165, filed on Nov. 21, 2001, provisional application No. 60/342,066, filed on Dec. 18, 2001, provisional application No. 60/371,457, filed on Apr. 9, 2002, provisional application No. 60/412,068, filed on Sep. 18, 2002.

(51) Int. Cl.
*A61K 9/12* (2006.01)
*A61K 9/14* (2006.01)
*A61M 15/00* (2006.01)

(52) U.S. Cl. .......................... 424/45; 424/46; 424/434; 424/489; 424/499; 514/958; 128/200.14; 128/200.15; 128/200.24

(58) Field of Classification Search .................. 424/45, 424/46, 489, 499, 434; 514/958; 128/200.14, 128/200.24, 203.15
See application file for complete search history.

(56) References Cited

U.S. PATENT DOCUMENTS 1,239,634 A     9/1917   Stuart (Continued)

FOREIGN PATENT DOCUMENTS

CA     2152684     1/1996

(Continued)

OTHER PUBLICATIONS

U.S. Appl. No. 10/633,876, filed Aug. 4, 2003, Hale et al.

(Continued)

*Primary Examiner*—Mina Haghighatian
(74) *Attorney, Agent, or Firm*—Swanson & Bratschun, L.L.C.

(57) ABSTRACT

An article for use in an aerosol device, for producing an aerosol of a drug composition is disclosed. The article includes a heat-conductive substrate having a surface with a selected surface area, and a drug composition film on the substrate surface having a selected film thickness of between 0.05 and 20 µm. The film thickness is such that an aerosol formed by vaporizing the drug composition by heating the substrate and condensing the vaporized compound contains 10% or less drug-degradation product and at least 50% of the total amount of drug composition contained in the film. The selected substrate surface area is such as to yield an effective human therapeutic dose of the drug aerosol. Also disclosed are methods of making and using the article.

12 Claims, 18 Drawing Sheets

Related U.S. Application Data application No. 10/153,839, filed on May 21, 2002, now Pat. No. 6,776,978, application No. 10/633,877, which is a continuation-in-part of application No. 10/153,311, filed on May 21, 2002, now Pat. No. 6,884,408, application No. 10/633,877, which is a continuation-in-part of application No. 10/153,831, filed on May 21, 2002, now Pat. No. 6,740,308, application No. 10/633,877, which is a continuation-in-part of application No. 10/153,313, filed on May 20, 2002, now abandoned, application No. 10/633,877, which is a continuation-in-part of application No. 10/153,139, filed on May 20, 2002, now Pat. No. 6,814,954, application No. 10/633,877, which is a continuation-in-part of application No. 10/152,652, filed on May 20, 2002, now Pat. No. 6,740,307, application No. 10/633,877, which is a continuation-in-part of application No. 10/152,640, filed on May 20, 2002, now Pat. No. 6,743,415, application No. 10/633,877, which is a continuation-in-part of application No. 10/152,639, filed on May 20, 2002, now Pat. No. 6,716,416, application No. 10/633,877, which is a continuation-in-part of application No. 10/150,857, filed on May 17, 2002, now Pat. No. 6,716,415, application No. 10/633,877, which is a continuation-in-part of application No.10/ 150,591, filed on May 17, 2002, now Pat. No. 6,780, 400, application No. 10/633,877, which is a continuation-in-part of application No. 10/151,596, filed on May 16, 2002, now Pat. No. 6,855,310, application No. 10/633,877, which is a continuation-in-part of application No. 10/151,626, filed on May 16, 2002, now Pat. No. 6,783,753, application No. 10/633,877, which is a continuation-in-part of application No. 10/150,267, filed on May 16, 2002, now Pat. No. 6,797,259, application No. 10/633,877, which is a continuation-in-part of application No. 10/150,268, filed on May 15, 2002, now Pat. No. 6,780,399, application No. 10/633,877, which is a continuation-in-part of application No. 10/150,056, filed on May 15, 2002, now Pat. No. 6,805,853, application No. 10/633,877, which is a continuation-in-part of application No. 10/146,516, filed on May 13, 2002, now Pat. No. 6,737,042, application No. 10/633,877, which is a continuation-in-part of application No. 10/146,515, filed on May 13, 2002, now Pat. No. 6,682,716, application No. 10/633,877, which is a continuation-in-part of application No. 10/146,088, filed on May 13, 2002, application No. 10/633,877, which is a continuation-in-part of application No. 10/146,080, filed on May 13, 2002, application No. 10/633,877, which is a continuation-in-part of application No. 10/057,197, filed on Oct. 26, 2001, application No. 10/633,877, which is a continuation-in-part of application No. 10/057,198, filed on Oct. 26, 2001.

(56) References Cited

U.S. PATENT DOCUMENTS

| | | |
|---|---|---|
| 1,535,486 A | 4/1925 | Lundy |
| 1,803,334 A | 5/1931 | Lehmann |
| 1,864,980 A | 6/1932 | Curran |
| 2,084,299 A | 6/1937 | Borden |
| 2,086,140 A | 7/1937 | Ernst |
| 2,230,753 A | 2/1941 | Klavehn et al. |
| 2,230,754 A | 2/1941 | Klavehn et al. |
| 2,243,669 A | 5/1941 | Clyne |
| 2,309,846 A | 2/1943 | Einar |
| 2,469,656 A | 5/1949 | Lienert |
| 2,714,649 A | 8/1955 | Critzer |
| 2,741,812 A | 4/1956 | Andre |
| 2,761,055 A | 8/1956 | Ike |
| 2,887,106 A | 5/1959 | Robinson |
| 2,898,649 A | 8/1959 | Murray |
| 2,902,484 A | 9/1959 | Horclois |
| 3,043,977 A | 7/1962 | Morowitz |
| 3,080,624 A | 3/1963 | Webber, III |
| 3,164,600 A | 1/1965 | Janssen et al. |
| 3,169,095 A | 2/1965 | Thiel et al. |
| 3,200,819 A | 8/1965 | Gilbert |
| 3,219,533 A | 11/1965 | Mullins |
| 3,282,729 A | 11/1966 | Richardson et al. |
| 3,296,249 A | 1/1967 | Bell |
| 3,299,185 A | 1/1967 | Oda et al. |
| 3,371,085 A | 2/1968 | Reeder et al. |
| 3,393,197 A | 7/1968 | Pachter |
| 3,433,791 A | 3/1969 | Bentley et al. |
| 3,560,607 A | 2/1971 | Hartley et al. |
| 3,701,782 A | 10/1972 | Hester |
| 3,749,547 A | 7/1973 | Gregory et al. |
| 3,763,347 A | 10/1973 | Whitaker et al. |
| 3,773,995 A | 11/1973 | Pachter et al. |
| 3,831,606 A | 8/1974 | Damani |
| 3,847,650 A | 11/1974 | Gregory et al. |
| 3,864,326 A | 2/1975 | Babington |
| 3,894,040 A | 7/1975 | Buzby, Jr. |
| 3,909,463 A | 9/1975 | Hartman |
| 3,930,796 A | 1/1976 | Haensel |
| 3,943,941 A | 3/1976 | Boyd et al. |
| 3,949,743 A | 4/1976 | Shanbrom |
| 3,971,377 A | 7/1976 | Damani |
| 3,982,095 A | 9/1976 | Robinson |
| 3,987,052 A | 10/1976 | Hester, Jr. |
| 4,008,723 A | 2/1977 | Borthwick et al. |
| 4,020,379 A | 4/1977 | Manning |
| 4,045,156 A | 8/1977 | Chu et al. |
| 4,079,742 A | 3/1978 | Rainer et al. |
| 4,104,210 A | 8/1978 | Coran et al. |
| 4,121,583 A | 10/1978 | Chen |
| 4,141,369 A | 2/1979 | Burruss |
| 4,160,765 A | 7/1979 | Weinstock |
| 4,166,087 A | 8/1979 | Cline et al. |
| 4,183,912 A | 1/1980 | Rosenthale |
| 4,184,099 A | 1/1980 | Lindauer et al. |
| 4,190,654 A | 2/1980 | Gherardi et al. |
| 4,198,200 A | 4/1980 | Fonda et al. |
| RE30,285 E | 5/1980 | Babington |
| 4,219,031 A | 8/1980 | Rainer et al. |
| 4,229,447 A | 10/1980 | Porter |
| 4,229,931 A | 10/1980 | Schlueter et al. |
| 4,232,002 A | 11/1980 | Nogrady |
| 4,236,544 A | 12/1980 | Osaka |
| 4,251,525 A | 2/1981 | Weinstock |
| 4,276,243 A | 6/1981 | Partus |
| 4,280,629 A | 7/1981 | Slaughter |
| 4,284,089 A | 8/1981 | Ray |
| 4,286,604 A | 9/1981 | Ehretsmann et al. |
| 4,303,083 A | 12/1981 | Burruss, Jr. |
| 4,340,072 A | 7/1982 | Bolt et al. |
| 4,346,059 A | 8/1982 | Spector |
| 4,347,855 A | 9/1982 | Lanzillotti et al. |
| 4,376,767 A | 3/1983 | Sloan |
| 4,391,285 A | 7/1983 | Burnett et al. |
| 4,423,071 A | 12/1983 | Chignac et al. |
| 4,474,191 A | 10/1984 | Steiner |
| 4,484,576 A | 11/1984 | Albarda |
| 4,508,726 A | 4/1985 | Coleman |
| 4,523,589 A | 6/1985 | Krauser |
| 4,556,539 A | 12/1985 | Spector |
| 4,566,451 A | 1/1986 | Badewien |

| | | | | | |
|---|---|---|---|---|---|
| 4,588,425 A | 5/1986 | Usry et al. | 5,093,894 A | 3/1992 | Deevi et al. |
| 4,588,721 A | 5/1986 | Mahan | 5,095,921 A | 3/1992 | Loose et al. |
| 4,591,615 A | 5/1986 | Aldred et al. | 5,099,861 A | 3/1992 | Clearman et al. |
| 4,605,552 A | 8/1986 | Fritschi | 5,105,831 A | 4/1992 | Banerjee et al. |
| 4,627,963 A | 12/1986 | Olson | 5,109,180 A | 4/1992 | Boultinghouse et al. |
| 4,647,428 A | 3/1987 | Gyulay | 5,112,598 A | 5/1992 | Biesalski |
| 4,647,433 A | 3/1987 | Spector | 5,118,494 A | 6/1992 | Schultz et al. |
| 4,654,370 A | 3/1987 | Marriott, III et al. | 5,119,834 A | 6/1992 | Shannon et al. |
| 4,683,231 A | 7/1987 | Glassman | 5,126,123 A | 6/1992 | Johnson |
| 4,693,868 A | 9/1987 | Katsuda et al. | 5,133,368 A | 7/1992 | Neumann et al. |
| 4,708,151 A | 11/1987 | Shelar | 5,135,009 A | 8/1992 | Muller et al. |
| 4,714,082 A | 12/1987 | Banerjee et al. | 5,137,034 A | 8/1992 | Perfetti et al. |
| 4,722,334 A | 2/1988 | Blackmer et al. | 5,144,962 A | 9/1992 | Counts et al. |
| 4,734,560 A | 3/1988 | Bowen | 5,146,915 A | 9/1992 | Montgomery |
| 4,735,217 A | 4/1988 | Gerth et al. | 5,149,538 A | 9/1992 | Granger et al. |
| 4,735,358 A | 4/1988 | Osamo et al. | 5,156,170 A | 10/1992 | Clearman et al. |
| 4,753,758 A | 6/1988 | Miller | 5,160,664 A | 11/1992 | Liu |
| 4,755,508 A | 7/1988 | Bock et al. | 5,164,740 A | 11/1992 | Ivri |
| 4,756,318 A | 7/1988 | Clearman et al. | 5,166,202 A | 11/1992 | Schweizer |
| 4,765,347 A | 8/1988 | Sensabaugh, Jr. et al. | 5,167,242 A | 12/1992 | Turner et al. |
| 4,771,795 A | 9/1988 | White et al. | 5,177,071 A | 1/1993 | Freidinger et al. |
| 4,774,971 A | 10/1988 | Vieten | 5,179,966 A | 1/1993 | Losee et al. |
| 4,793,365 A | 12/1988 | Sensabaugh, Jr. et al. | 5,186,164 A | 2/1993 | Raghuprasad |
| 4,793,366 A | 12/1988 | Hill | 5,192,548 A | 3/1993 | Velasquez et al. |
| 4,800,903 A | 1/1989 | Ray et al. | 5,224,498 A | 7/1993 | Deevi et al. |
| 4,801,411 A | 1/1989 | Wellinghoff et al. | 5,226,411 A | 7/1993 | Levine |
| 4,814,161 A | 3/1989 | Jinks et al. | 5,229,120 A | 7/1993 | DeVincent |
| 4,819,665 A | 4/1989 | Roberts et al. | 5,229,382 A | 7/1993 | Chakrabarti et al. |
| 4,848,374 A | 7/1989 | Chard et al. | 5,240,922 A | 8/1993 | O'Neill |
| 4,852,561 A | 8/1989 | Sperry | 5,249,586 A | 10/1993 | Morgan et al. |
| 4,853,517 A | 8/1989 | Bowen et al. | 5,255,674 A | 10/1993 | Oftedal et al. |
| 4,854,331 A | 8/1989 | Banerjee et al. | 5,261,424 A | 11/1993 | Sprin et al. |
| 4,858,630 A | 8/1989 | Banerjee et al. | 5,264,433 A | 11/1993 | Sato et al. |
| 4,863,720 A | 9/1989 | Burghart et al. | 5,269,327 A | 12/1993 | Counts et al. |
| 4,881,541 A | 11/1989 | Eger et al. | 5,284,133 A | 2/1994 | Burns et al. |
| 4,881,556 A | 11/1989 | Clearman et al. | 5,285,798 A | 2/1994 | Banerjee et al. |
| 4,889,850 A | 12/1989 | Thornfeldt et al. | 5,292,499 A | 3/1994 | Evans et al. |
| 4,892,109 A | 1/1990 | Strubel | 5,322,075 A | 6/1994 | Deevi et al. |
| 4,895,719 A | 1/1990 | Radhakrishnan et al. | 5,333,106 A | 7/1994 | Lanpher et al. |
| 4,906,417 A | 3/1990 | Gentry | 5,345,951 A | 9/1994 | Serrano et al. |
| 4,911,157 A | 3/1990 | Miller | 5,357,984 A | 10/1994 | Farrier et al. |
| 4,917,119 A | 4/1990 | Potter et al. | 5,363,842 A | 11/1994 | Mishelevich et al. |
| 4,917,120 A | 4/1990 | Hill | 5,364,838 A | 11/1994 | Rubsamen |
| 4,917,830 A | 4/1990 | Ortiz et al. | 5,366,770 A | 11/1994 | Wang |
| 4,922,901 A | 5/1990 | Brooks et al. | 5,372,148 A | 12/1994 | McCafferty et al. |
| 4,924,883 A | 5/1990 | Perfetti et al. | 5,376,386 A | 12/1994 | Ganderton et al. |
| 4,928,714 A | 5/1990 | Shannon | 5,388,574 A | 2/1995 | Ingebrethsen |
| 4,935,624 A | 6/1990 | Henion et al. | 5,391,081 A | 2/1995 | Lampotang et al. |
| 4,941,483 A | 7/1990 | Ridings et al. | 5,399,574 A | 3/1995 | Robertson et al. |
| 4,947,874 A | 8/1990 | Brooks et al. | 5,400,808 A | 3/1995 | Turner et al. |
| 4,947,875 A | 8/1990 | Brooks et al. | 5,400,969 A | 3/1995 | Keene |
| 4,950,664 A | 8/1990 | Goldberg | 5,402,517 A | 3/1995 | Gillett et al. |
| 4,955,945 A | 9/1990 | Weick | 5,408,574 A | 4/1995 | Deevi et al. |
| 4,959,380 A | 9/1990 | Wilson | 5,436,230 A | 7/1995 | Soudant et al. |
| 4,963,289 A | 10/1990 | Ortiz et al. | 5,451,408 A | 9/1995 | Mezei et al. |
| 4,968,885 A | 11/1990 | Willoughby | 5,455,043 A | 10/1995 | Fischel-Ghodsian |
| 4,984,158 A | 1/1991 | Hillsman | 5,456,247 A | 10/1995 | Shilling et al. |
| 4,989,619 A | 2/1991 | Clearman et al. | 5,456,677 A | 10/1995 | Spector |
| 5,016,425 A | 5/1991 | Weick | 5,457,100 A | 10/1995 | Daniel |
| 5,017,575 A | 5/1991 | Golwyn | 5,457,101 A | 10/1995 | Greenwood et al. |
| 5,019,122 A | 5/1991 | Clearman et al. | 5,459,137 A | 10/1995 | Andrasi et al. |
| 5,020,548 A | 6/1991 | Farrier et al. | 5,462,740 A | 10/1995 | Evenstad et al. |
| 5,027,836 A | 7/1991 | Shannon et al. | 5,468,936 A | 11/1995 | Deevi et al. |
| 5,033,483 A | 7/1991 | Clearman et al. | 5,479,948 A | 1/1996 | Counts et al. |
| 5,038,769 A | 8/1991 | Krauser | 5,501,236 A | 3/1996 | Hill et al. |
| 5,042,509 A | 8/1991 | Banerjee et al. | 5,505,214 A | 4/1996 | Collins et al. |
| 5,049,389 A | 9/1991 | Radhakrishnun | 5,507,277 A | 4/1996 | Rubsamen et al. |
| 5,060,666 A | 10/1991 | Clearman et al. | 5,511,726 A | 4/1996 | Greenspan et al. |
| 5,060,667 A | 10/1991 | Strubel | 5,519,019 A | 5/1996 | Andrasi et al. |
| 5,060,671 A | 10/1991 | Counts et al. | 5,525,329 A | 6/1996 | Snyder et al. |
| 5,067,499 A | 11/1991 | Banerjee et al. | 5,537,507 A | 7/1996 | Mariner et al. |
| 5,072,726 A | 12/1991 | Mazloomdoost et al. | 5,538,020 A | 7/1996 | Farrier et al. |
| 5,076,292 A | 12/1991 | Sensabaugh, Jr. et al. | 5,540,959 A | 7/1996 | Wang |

| Patent | Date | Name |
|---|---|---|
| 5,543,434 A | 8/1996 | Weg |
| 5,544,646 A | 8/1996 | Lloyd et al. |
| 5,564,442 A | 10/1996 | MacDonald et al. |
| 5,565,148 A | 10/1996 | Pendergrass |
| 5,577,156 A | 11/1996 | Costello |
| 5,584,701 A | 12/1996 | Lampotang et al. |
| 5,586,550 A | 12/1996 | Ivri et al. |
| 5,591,409 A | 1/1997 | Watkins |
| 5,592,934 A | 1/1997 | Thwaites |
| 5,593,792 A | 1/1997 | Farrier et al. |
| 5,605,146 A | 2/1997 | Sarela |
| 5,605,897 A | 2/1997 | Beasley, Jr. et al. |
| 5,607,691 A | 3/1997 | Hale et al. |
| 5,613,504 A | 3/1997 | Collins et al. |
| 5,613,505 A | 3/1997 | Campbell et al. |
| 5,619,984 A | 4/1997 | Hodson et al. |
| 5,622,944 A | 4/1997 | Hale et al. |
| 5,627,178 A | 5/1997 | Chakrabarti et al. |
| 5,649,554 A | 7/1997 | Sprinkel |
| 5,655,523 A | 8/1997 | Hodson et al. |
| 5,656,255 A | 8/1997 | Jones |
| 5,660,166 A | 8/1997 | Lloyd et al. |
| 5,666,977 A | 9/1997 | Higgins et al. |
| 5,690,809 A | 11/1997 | Subramaniam et al. |
| 5,694,919 A | 12/1997 | Rubsamen et al. |
| 5,718,222 A | 2/1998 | Lloyd et al. |
| 5,724,957 A | 3/1998 | Rubsamen et al. |
| 5,725,756 A | 3/1998 | Subramaniam et al. |
| 5,733,572 A | 3/1998 | Unger et al. |
| 5,735,263 A | 4/1998 | Rubsamen et al. |
| 5,738,865 A | 4/1998 | Baichwal et al. |
| 5,743,250 A | 4/1998 | Gonda et al. |
| 5,743,251 A | 4/1998 | Howell et al. |
| 5,744,469 A | 4/1998 | Tran |
| 5,747,001 A | 5/1998 | Wiedmann et al. |
| 5,756,449 A | 5/1998 | Andersen et al. |
| 5,758,637 A | 6/1998 | Ivri et al. |
| 5,767,117 A | 6/1998 | Moskowitz |
| 5,769,621 A | 6/1998 | Early et al. |
| 5,770,222 A | 6/1998 | Unger et al. |
| 5,771,882 A | 6/1998 | Psaros et al. |
| 5,776,928 A | 7/1998 | Beasley, Jr. |
| 5,804,212 A | 9/1998 | Illum |
| 5,809,997 A | 9/1998 | Wolf |
| 5,817,656 A | 10/1998 | Beasley, Jr. et al. |
| 5,819,756 A | 10/1998 | Mielordt |
| 5,823,178 A | 10/1998 | Lloyd et al. |
| 5,829,436 A | 11/1998 | Rubsamen et al. |
| 5,833,891 A | 11/1998 | Subramaniam et al. |
| 5,840,246 A | 11/1998 | Hammons et al. |
| 5,855,564 A | 1/1999 | Ruskewicz |
| 5,855,913 A | 1/1999 | Hanes et al. |
| 5,865,185 A | 2/1999 | Collins et al. |
| 5,874,064 A | 2/1999 | Edwards et al. |
| 5,874,481 A | 2/1999 | Weers et al. |
| 5,875,776 A | 3/1999 | Vaghefi |
| 5,878,752 A | 3/1999 | Adams et al. |
| 5,884,620 A | 3/1999 | Gonda et al. |
| 5,890,908 A | 4/1999 | Lampotang et al. |
| 5,894,841 A | 4/1999 | Voges |
| 5,904,900 A | 5/1999 | Bleuse et al. |
| 5,906,811 A | 5/1999 | Hersh |
| 5,907,075 A | 5/1999 | Subramaniam et al. |
| 5,910,301 A | 6/1999 | Farr et al. |
| 5,915,378 A | 6/1999 | Lloyd et al. |
| 5,918,595 A | 7/1999 | Olsson |
| 5,928,520 A | 7/1999 | Haumesser |
| 5,929,093 A | 7/1999 | Pang et al. |
| 5,934,272 A | 8/1999 | Lloyd et al. |
| 5,934,289 A | 8/1999 | Watkins et al. |
| 5,935,604 A | 8/1999 | Illum |
| 5,938,117 A | 8/1999 | Ivri |
| 5,939,100 A | 8/1999 | Albrechtsen et al. |
| 5,941,240 A | 8/1999 | Gonda et al. |
| 5,944,012 A | 8/1999 | Pera |
| 5,957,124 A | 9/1999 | Lloyd et al. |
| 5,960,792 A | 10/1999 | Lloyd et al. |
| 5,970,973 A | 10/1999 | Gonda et al. |
| 5,971,951 A | 10/1999 | Ruskewicz |
| 5,985,309 A | 11/1999 | Edwards et al. |
| 5,993,805 A | 11/1999 | Sutton et al. |
| 6,004,516 A | 12/1999 | Rasouli et al. |
| 6,004,970 A | 12/1999 | O'Malley et al. |
| 6,008,214 A | 12/1999 | Kwon et al. |
| 6,008,216 A | 12/1999 | Chakrabarti et al. |
| 6,013,050 A | 1/2000 | Bellhouse et al. |
| 6,014,969 A | 1/2000 | Lloyd et al. |
| 6,014,970 A | 1/2000 | Ivri et al. |
| 6,041,777 A | 3/2000 | Faithfull et al. |
| 6,044,777 A | 4/2000 | Walsh |
| 6,048,550 A | 4/2000 | Chan et al. |
| 6,048,857 A | 4/2000 | Ellinwood, Jr. et al. |
| 6,050,260 A | 4/2000 | Daniell et al. |
| 6,051,257 A | 4/2000 | Kodas et al. |
| 6,051,566 A | 4/2000 | Bianco |
| 6,053,176 A | 4/2000 | Adams et al. |
| RE36,744 E | 6/2000 | Goldberg |
| 6,085,026 A | 7/2000 | Hammons et al. |
| 6,089,857 A | 7/2000 | Matsuura et al. |
| 6,090,212 A | 7/2000 | Mahawili |
| 6,090,403 A | 7/2000 | Block et al. |
| 6,095,134 A | 8/2000 | Sievers et al. |
| 6,095,153 A | 8/2000 | Kessler et al. |
| 6,098,620 A | 8/2000 | Lloyd et al. |
| 6,102,036 A | 8/2000 | Slutsky et al. |
| 6,113,795 A | 9/2000 | Subramaniam et al. |
| 6,117,866 A | 9/2000 | Bondinell et al. |
| 6,125,853 A | 10/2000 | Susa et al. |
| 6,126,919 A | 10/2000 | Stefely et al. |
| 6,131,566 A | 10/2000 | Ashurst et al. |
| 6,131,570 A | 10/2000 | Schuster et al. |
| 6,133,327 A | 10/2000 | Kimura et al. |
| 6,135,369 A | 10/2000 | Prendergast et al. |
| 6,136,295 A | 10/2000 | Edwards et al. |
| 6,138,683 A | 10/2000 | Hersh et al. |
| 6,140,323 A | 10/2000 | Ellinwood, Jr. et al. |
| 6,143,277 A | 11/2000 | Ashurst et al. |
| 6,143,746 A | 11/2000 | Daugan et al. |
| 6,149,892 A | 11/2000 | Britto |
| 6,155,268 A | 12/2000 | Takeuchi |
| 6,158,431 A | 12/2000 | Poole |
| 6,167,880 B1 | 1/2001 | Gonda et al. |
| 6,178,969 B1 | 1/2001 | St. Charles |
| 6,234,167 B1 | 5/2001 | Cox et al. |
| 6,241,969 B1 | 6/2001 | Saidi et al. |
| 6,250,301 B1 | 6/2001 | Pate |
| 6,255,334 B1 | 7/2001 | Sands |
| 6,263,872 B1 | 7/2001 | Schuster et al. |
| 6,264,922 B1 | 7/2001 | Wood et al. |
| 6,284,287 B1 | 9/2001 | Sarlikiotis et al. |
| 6,299,900 B1 | 10/2001 | Reed et al. |
| 6,300,710 B1 | 10/2001 | Nakamori |
| 6,306,431 B1 | 10/2001 | Zhang et al. |
| 6,309,668 B1 | 10/2001 | Bastin et al. |
| 6,309,986 B1 | 10/2001 | Flashinski et al. |
| 6,313,176 B1 | 11/2001 | Ellinwood, Jr. et al. |
| 6,325,475 B1 | 12/2001 | Hayes et al. |
| 6,376,550 B1 | 4/2002 | Raber et al. |
| 6,390,453 B1 | 5/2002 | Frederickson et al. |
| 6,408,854 B1 | 6/2002 | Gonda et al. |
| 6,413,930 B1 | 7/2002 | Ratti et al. |
| 6,420,351 B1 | 7/2002 | Tsai et al. |
| 6,431,166 B2 | 8/2002 | Gonda et al. |
| 6,443,152 B1 | 9/2002 | Lockhart et al. |
| 6,461,591 B1 | 10/2002 | Keller et al. |
| 6,491,233 B2 | 12/2002 | Nichols |

| | | | | | | |
|---|---|---|---|---|---|---|
| 6,501,052 B2 | 12/2002 | Cox et al. | | 2003/0032638 A1 | 2/2003 | Kim et al. |
| 6,506,762 B1 | 1/2003 | Horvath et al. | | 2003/0033055 A1 | 2/2003 | McRae et al. |
| 6,514,482 B1 | 2/2003 | Bartus et al. | | 2003/0035776 A1 | 2/2003 | Hodges et al. |
| 6,516,796 B1 | 2/2003 | Cox et al. | | 2003/0049025 A1 | 3/2003 | Neumann et al. |
| 6,557,552 B1 | 5/2003 | Cox et al. | | 2003/0051728 A1 | 3/2003 | Lloyd et al. |
| 6,561,186 B2 | 5/2003 | Casper et al. | | 2003/0062042 A1 | 4/2003 | Wensley et al. |
| 6,568,390 B2 | 5/2003 | Nichols et al. | | 2003/0091511 A1 | 5/2003 | Rabinowitz et al. |
| 6,591,839 B2 | 7/2003 | Meyer et al. | | 2003/0106551 A1 | 6/2003 | Sprinkel et al. |
| 6,632,047 B2 | 10/2003 | Vinegar | | 2003/0118512 A1 | 6/2003 | Shen |
| 6,648,950 B2 | 11/2003 | Lee et al. | | 2003/0121906 A1 | 7/2003 | Abbott et al. |
| 6,671,945 B2 | 1/2004 | Gerber et al. | | 2003/0131843 A1 | 7/2003 | Lu |
| 6,680,668 B2 | 1/2004 | Gerber et al. | | 2003/0132219 A1 | 7/2003 | Cox et al. |
| 6,681,769 B2 | 1/2004 | Sprinkel et al. | | 2003/0138382 A1 | 7/2003 | Rabinowitz |
| 6,681,998 B2 | 1/2004 | Sharpe et al. | | 2003/0138508 A1 | 7/2003 | Novack et al. |
| 6,688,313 B2 | 2/2004 | Wrenn et al. | | 2003/0156829 A1 | 8/2003 | Cox et al. |
| 6,694,975 B2 | 2/2004 | Schuster et al. | | 2003/0206869 A1 | 11/2003 | Rabinowitz et al. |
| 6,701,921 B2 | 3/2004 | Sprinkel et al. | | 2003/0209240 A1 | 11/2003 | Hale et al. |
| 6,701,922 B2 | 3/2004 | Hindle et al. | | 2004/0009128 A1 | 1/2004 | Rabinowitz et al. |
| 6,715,487 B2 | 4/2004 | Nichols et al. | | 2004/0016427 A1* | 1/2004 | Byron et al. ............ 128/200.14 |
| 6,728,478 B2 | 4/2004 | Cox et al. | | 2004/0035409 A1 | 2/2004 | Harwig et al. |
| 6,772,756 B2 | 8/2004 | Shayan | | 2004/0055504 A1 | 3/2004 | Lee et al. |
| 6,772,757 B2 | 8/2004 | Sprinkel, Jr. et al. | | 2004/0081624 A1 | 4/2004 | Nguyen et al. |
| 6,779,520 B2 | 8/2004 | Genova et al. | | 2004/0096402 A1 | 5/2004 | Hodges et al. |
| 7,402,777 B2 | 7/2008 | Hale et al. | | 2004/0099266 A1 | 5/2004 | Cross et al. |
| 7,442,368 B2 | 10/2008 | Rabinowitz et al. | | 2004/0099269 A1 | 5/2004 | Hale et al. |
| 7,445,768 B2 | 11/2008 | Rabinowitz et al. | | 2004/0101481 A1 | 5/2004 | Hale et al. |
| 7,449,172 B2 | 11/2008 | Rabinowitz et al. | | 2004/0102434 A1 | 5/2004 | Hale et al. |
| 7,449,173 B2 | 11/2008 | Rabinowitz et al. | | 2004/0105818 A1 | 6/2004 | Hale et al. |
| 7,449,174 B2 | 11/2008 | Rabinowitz et al. | | 2004/0105819 A1 | 6/2004 | Hale et al. |
| 7,449,175 B2 | 11/2008 | Rabinowitz et al. | | 2004/0126326 A1 | 7/2004 | Rabinowitz et al. |
| 7,465,435 B2 | 12/2008 | Rabinowitz et al. | | 2004/0126327 A1 | 7/2004 | Rabinowitz et al. |
| 7,465,436 B2 | 12/2008 | Rabinowitz et al. | | 2004/0126328 A1 | 7/2004 | Rabinowitz et al. |
| 7,465,437 B2 | 12/2008 | Rabinowitz et al. | | 2004/0126329 A1 | 7/2004 | Rabinowitz et al. |
| 7,468,179 B2 | 12/2008 | Rabinowitz et al. | | 2004/0127481 A1 | 7/2004 | Rabinowitz et al. |
| 7,470,421 B2 | 12/2008 | Rabinowitz et al. | | 2004/0127490 A1 | 7/2004 | Rabinowitz et al. |
| 7,485,285 B2 | 2/2009 | Rabinowitz et al. | | 2004/0156788 A1 | 8/2004 | Rabinowitz et al. |
| 7,488,469 B2 | 2/2009 | Rabinowitz et al. | | 2004/0156789 A1 | 8/2004 | Rabinowitz et al. |
| 7,491,047 B2 | 2/2009 | Rabinowitz et al. | | 2004/0156790 A1 | 8/2004 | Rabinowitz et al. |
| 2001/0020147 A1 | 9/2001 | Staniforth et al. | | 2004/0156791 A1 | 8/2004 | Rabinowitz et al. |
| 2001/0042546 A1 | 11/2001 | Umeda et al. | | 2004/0234699 A1 | 11/2004 | Hale et al. |
| 2002/0031480 A1 | 3/2002 | Peart et al. | | 2004/0234914 A1 | 11/2004 | Hale et al. |
| 2002/0037828 A1 | 3/2002 | Wilson et al. | | 2004/0234916 A1 | 11/2004 | Hale et al. |
| 2002/0058009 A1 | 5/2002 | Bartus et al. | | 2005/0034723 A1 | 2/2005 | Bennett et al. |
| 2002/0061281 A1 | 5/2002 | Osbakken et al. | | 2005/0079166 A1 | 4/2005 | Damani et al. |
| 2002/0078955 A1 | 6/2002 | Nichols et al. | | 2005/0126562 A1 | 6/2005 | Rabinowitz et al. |
| 2002/0086852 A1 | 7/2002 | Cantor | | 2005/0131739 A1 | 6/2005 | Rabinowitz et al. |
| 2002/0097139 A1 | 7/2002 | Gerber et al. | | 2005/0268911 A1 | 12/2005 | Cross et al. |
| 2002/0112723 A1 | 8/2002 | Schuster et al. | | 2006/0032496 A1 | 2/2006 | Hale et al. |
| 2002/0117175 A1 | 8/2002 | Kottayil et al. | | 2006/0032501 A1 | 2/2006 | Hale et al. |
| 2002/0176841 A1 | 11/2002 | Barker et al. | | 2006/0120962 A1 | 6/2006 | Rabinowitz et al. |
| 2003/0000518 A1 | 1/2003 | Rabinowitz et al. | | 2006/0193788 A1 | 8/2006 | Hale et al. |
| 2003/0004142 A1 | 1/2003 | Prior et al. | | 2006/0233717 A1 | 10/2006 | Hale et al. |
| 2003/0005924 A1 | 1/2003 | Rabinowitz et al. | | 2006/0246011 A1 | 11/2006 | Rabinowitz et al. |
| 2003/0005925 A1 | 1/2003 | Hale et al. | | 2006/0246012 A1 | 11/2006 | Rabinowitz et al. |
| 2003/0007933 A1 | 1/2003 | Rabinowitz et al. | | 2006/0257329 A1 | 11/2006 | Rabinowitz et al. |
| 2003/0007934 A1 | 1/2003 | Rabinowitz et al. | | 2006/0269487 A1 | 11/2006 | Rabinowitz et al. |
| 2003/0012737 A1 | 1/2003 | Rabinowitz et al. | | 2006/0280692 A1 | 12/2006 | Rabinowitz et al. |
| 2003/0012738 A1 | 1/2003 | Rabinowitz et al. | | 2007/0014737 A1 | 1/2007 | Rabinowitz et al. |
| 2003/0012740 A1 | 1/2003 | Rabinowitz et al. | | 2007/0031340 A1 | 2/2007 | Hale et al. |
| 2003/0015189 A1 | 1/2003 | Rabinowitz et al. | | 2007/0122353 A1 | 5/2007 | Hale et al. |
| 2003/0015190 A1 | 1/2003 | Rabinowitz et al. | | 2007/0140982 A1 | 6/2007 | Every et al. |
| 2003/0015196 A1 | 1/2003 | Hodges et al. | | 2007/0286816 A1 | 12/2007 | Hale et al. |
| 2003/0015197 A1 | 1/2003 | Hale et al. | | 2008/0110872 A1 | 5/2008 | Hale et al. |
| 2003/0017114 A1 | 1/2003 | Rabinowitz et al. | | 2008/0175796 A1 | 7/2008 | Rabinowitz et al. |
| 2003/0017115 A1 | 1/2003 | Rabinowitz et al. | | 2008/0216828 A1 | 9/2008 | Wensley |
| 2003/0017116 A1 | 1/2003 | Rabinowitz et al. | | 2008/0299048 A1 | 12/2008 | Hale et al. |
| 2003/0017117 A1 | 1/2003 | Rabinowitz et al. | | 2008/0306285 A1 | 12/2008 | Hale et al. |
| 2003/0017118 A1 | 1/2003 | Rabinowitz et al. | | 2008/0311176 A1 | 12/2008 | Hale et al. |
| 2003/0017119 A1 | 1/2003 | Rabinowitz et al. | | | | |
| 2003/0017120 A1 | 1/2003 | Rabinowitz et al. | | | | |
| 2003/0021753 A1 | 1/2003 | Rabinowitz et al. | | | FOREIGN PATENT DOCUMENTS | |
| 2003/0021754 A1 | 1/2003 | Rabinowitz et al. | | | | |
| 2003/0021755 A1 | 1/2003 | Hale et al. | | CN | 1082365 | 2/1994 |

| | | |
|---|---|---|
| CN | 1176075 | 3/1998 |
| DE | 198 54 007 | 5/2000 |
| EP | 0 039 369 | 11/1981 |
| EP | 0 274 431 | 7/1988 |
| EP | 0 277 519 | 8/1988 |
| EP | 0 358 114 | 3/1990 |
| EP | 0 430 559 | 6/1991 |
| EP | 0 492 485 | 7/1992 |
| EP | 0 606 486 | 7/1994 |
| EP | 0 734 719 | 2/1996 |
| EP | 0 967 214 | 12/1999 |
| EP | 1 080 720 | 7/2001 |
| EP | 1 177 793 | 2/2002 |
| EP | 0 808 635 B1 | 7/2003 |
| FR | 921 852 A | 5/1947 |
| FR | 2 428 068 A | 1/1980 |
| GB | 502 761 | 1/1938 |
| GB | 903 866 | 8/1962 |
| GB | 1 366 041 | 9/1974 |
| GB | 2 108 390 | 5/1983 |
| GB | 2 122 903 | 1/1984 |
| HU | 200105 B | 10/1988 |
| HU | 219392 B | 6/1993 |
| WO | WO 85/00520 | 2/1985 |
| WO | WO 88/08304 | 11/1988 |
| WO | WO 90/02737 | 3/1990 |
| WO | WO 90/07333 | 7/1990 |
| WO | WO 91/07947 | 6/1991 |
| WO | WO 91/18525 | 12/1991 |
| WO | WO 92/05781 | 4/1992 |
| WO | WO 92/15353 | 9/1992 |
| WO | WO 92/19303 | 11/1992 |
| WO | WO 93/12823 | 7/1993 |
| WO | WO 94/09842 | 5/1994 |
| WO | WO 94/16717 | 8/1994 |
| WO | WO 94/16757 | 8/1994 |
| WO | WO 94/16759 | 8/1994 |
| WO | WO 94/17369 | 8/1994 |
| WO | WO 94/17370 | 8/1994 |
| WO | WO 94/27576 | 12/1994 |
| WO | WO 94/27653 | 12/1994 |
| WO | WO 95/31182 | 11/1995 |
| WO | WO 96/00069 | 1/1996 |
| WO | WO 96/00070 | 1/1996 |
| WO | WO 96/00071 | 1/1996 |
| WO | WO 96/09846 | 4/1996 |
| WO | WO 96/10663 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 96/31198 | 10/1996 |
| WO | WO 96/37198 | 11/1996 |
| WO | WO 97/16181 | 5/1997 |
| WO | WO 97/17948 | 5/1997 |
| WO | WO 97/23221 | 7/1997 |
| WO | WO 97/27804 | 8/1997 |
| WO | WO 97/31691 | 9/1997 |
| WO | WO 97/35562 | 10/1997 |
| WO | WO 97/36574 | 10/1997 |
| WO | WO 97/40819 | 11/1997 |
| WO | WO 97/49690 | 12/1997 |
| WO | WO 98/02186 | 1/1998 |
| WO | WO 98/16205 | 4/1998 |
| WO | WO 98/22170 | 5/1998 |
| WO | WO 98/29110 | 7/1998 |
| WO | WO 98/31346 | 7/1998 |
| WO | WO 98/34595 | 8/1998 |
| WO | WO 98/36651 | 8/1998 |
| WO | WO 98/37896 | 8/1998 |
| WO | WO 99/04797 | 2/1999 |
| WO | WO 99/16419 | 4/1999 |
| WO | WO 99/24433 | 5/1999 |
| WO | WO 99/37347 | 7/1999 |
| WO | WO 99/37625 | 7/1999 |
| WO | WO 99/44664 | 9/1999 |
| WO | WO 99/55362 | 11/1999 |
| WO | WO 99/59710 | 11/1999 |
| WO | WO 99/64094 | 12/1999 |
| WO | WO 00/00176 | 1/2000 |
| WO | WO 00/00215 | 1/2000 |
| WO | WO 00/00244 | 1/2000 |
| WO | WO 00/19991 | 4/2000 |
| WO | WO 00/27359 | 5/2000 |
| WO | WO 00/27363 | 5/2000 |
| WO | WO 00/28979 | 5/2000 |
| WO | WO 00/29053 | 5/2000 |
| WO | WO 00/29167 | 5/2000 |
| WO | WO 00/35417 | 6/2000 |
| WO | WO 00/38618 | 7/2000 |
| WO | WO 00/44350 | 8/2000 |
| WO | WO 00/44730 | 8/2000 |
| WO | WO 00/47203 | 9/2000 |
| WO | WO 00/51491 | 9/2000 |
| WO | WO 00/64940 | 11/2000 |
| WO | WO 00/66084 | 11/2000 |
| WO | WO 00/66106 | 11/2000 |
| WO | WO 00/66206 | 11/2000 |
| WO | WO 00/72827 | 12/2000 |
| WO | WO 00/76673 | 12/2000 |
| WO | WO 01/05459 | 1/2001 |
| WO | WO 01/13957 | 3/2001 |
| WO | WO 01/17568 | 3/2001 |
| WO | WO 01/19528 | 3/2001 |
| WO | WO 01/29011 | 4/2001 |
| WO | WO 01/32144 | 5/2001 |
| WO | WO 01/41732 | 6/2001 |
| WO | WO 01/043801 | 6/2001 |
| WO | WO 01/95903 | 12/2001 |
| WO | WO 02/00198 | 1/2002 |
| WO | WO 02/24158 | 3/2002 |
| WO | WO 02/51466 | 7/2002 |
| WO | WO 02/056866 | 7/2002 |
| WO | WO 02/094234 | 11/2002 |
| WO | WO 02/098389 | 12/2002 |
| WO | WO 03/37412 | 5/2003 |

OTHER PUBLICATIONS

U.S. Appl. No. 10/749,537, filed Dec. 30, 2003, Rabinowitz et al.
U.S. Appl. No. 10/749,539, filed Dec. 30, 2003, Rabinowitz et al.
U.S. Appl. No. 10/766,149, filed Jan. 27, 2004, Rabinowitz et al.
U.S. Appl. No. 10/766,279, filed Jan. 27, 2004, Rabinowitz et al.
U.S. Appl. No. 10/766,566, filed Jan. 27, 2004, Rabinowitz et al.
U.S. Appl. No. 10/766,574, filed Jan. 27, 2004, Rabinowitz et al.
U.S. Appl. No. 10/766,634, filed Jan. 27, 2004, Rabinowitz et al.
U.S. Appl. No. 10/766,647, filed Jan. 27, 2004, Rabinowitz et al.
U.S. Appl. No. 10/767,115, filed Jan. 28, 2004, Rabinowitz et al.
U.S. Appl. No. 10/768,205, filed Jan. 29, 2004, Rabinowitz et al.
U.S. Appl. No. 10/768,220, filed Jan. 29, 2004, Rabinowitz et al.
U.S. Appl. No. 10/768,281, filed Jan. 29, 2004, Rabinowitz et al.
U.S. Appl. No. 10/768,293, filed Jan. 29, 2004, Rabinowitz et al.
U.S. Appl. No. 10/769,046, filed Jan. 30, 2004, Rabinowitz et al.
U.S. Appl. No. 10/769,051, filed Jan. 30, 2004, Rabinowitz et al.
U.S. Appl. No. 10/769,157, filed Jan. 29, 2004, Rabinowitz et al.
U.S. Appl. No. 10/769,197, filed Jan. 29, 2004, Rabinowitz et al.
U.S. Appl. No. 10/775,583, filed Feb. 9, 2004, Rabinowitz et al.
U.S. Appl. No. 10/775,586, filed Feb. 9, 2004, Rabinowitz et al.
U.S. Appl. No. 10/791,915, filed Mar. 3, 2004, Hale et al.
U.S. Appl. No. 10/792,001, filed Mar. 3, 2004, Rabinowitz et al.
U.S. Appl. No. 10/792,012, filed Mar. 3, 2004, Hale et al.
U.S. Appl. No. 10/792,013, filed Mar. 3, 2004, Rabinowitz et al.
U.S. Appl. No. 10/792,096, filed Mar. 3, 2004, Hale et al.
U.S. Appl. No. 10/792,239, filed Mar. 3, 2004, Hale et al.
U.S. Appl. No. 10/813,721, filed Mar. 31, 2004, Rabinowitz et al.

U.S. Appl. No. 10/813,722, filed Mar. 31, 2004, Rabinowitz et al.
U.S. Appl. No. 10/814,690, filed Mar. 31, 2004, Rabinowitz et al.
U.S. Appl. No. 10/814,998, filed Mar. 31, 2004, Rabinowitz et al.
U.S. Appl. No. 10/815,527, filed Apr. 1, 2004, Rabinowitz et al.
U.S. Appl. No. 10/816,407, filed Apr. 1, 2004, Rabinowitz et al.
U.S. Appl. No. 10/816,492, filed Apr. 1, 2004, Rabinowitz et al.
U.S. Appl. No. 10/816,567, filed Apr. 1, 2004, Rabinowitz et al.
U.S. Appl. No. 10/912,462, filed Aug. 4, 2004, Hale et al.
Anderson, M.E. (1982). "Recent Advances in Methodology and Concepts for Characterizing Inhalation Pharmacokinetic Parameters in Animals and Man," *Drug Metabolism Reviews*. 13(5):799-826.
Bennett, R. L. et al. (1981). "Patient-Controlled Analgesia: A New Concept of Postoperative Pain Relief," *Annual Surg*. 195(6):700-705.
Benowitz (1994). "Individual Differences in Nicotine Kinetics and Metabolism in Humans," NIDA Research Monography, 2 pages.
BP: Chemicals Products-Barrier Resins (1999). located at <http://www.bp.com/chemicals/products/product.asp> (visited on Aug. 2, 2001), 8 pages.
Brand, P. et al. (Jun. 2000). "Total Deposition of Therapeutic Particles During Spontaneous and Controlled Inhalations," *Journal of Pharmaceutical Sciences*. 89(6):724-731.
Campbell, Fiona A. et al. (2001). "Are cannabinoids an effective and safe treatment options in the management of pain? A qualitative systemic review." vol. 323 (7303): 13-16.
Carroll, M.E. et al. (1990), "Cocaine-Base Smoking in Rhesus Monkey: Reinforcing and Physiological Effects," Psychopharmacology (Berl) 102:443-450.
Cichewicz, Diana L. et al. (May 1999) "Enhancement of mu opioid antinociception by oral DELTA 9—tetrahydrocannabinol: Dose response analysis and receptor indentification" Journal of Pharmacology and Experimental Therapeutics vol. 289 (2): 859-867.
Clark, A. and Byron, P. (1986). "Dependence of Pulmonary Absorption Kinetics on Aerosol Particle Size," *Z. Erkrank*. 166:13-24.
Dallas, C. et al. (1983). "A Small Animal Model for Direct Respiratory and Hemodynamic Measurements in Toxicokinetic Studies of Volatile Chemicals," *Devlopments in the Science and Practice of Toxicology*. Hayes, A. W. et al. eds., Elsevier Science Publishers, New York. pp. 419-422.
Darquenne, C. et al. (1997). "Aerosol Dispersion in Human Lung: Comparison Between Numerical Simulations and Experiments for Bolus Tests," *American Physiological Society*. 966-974.
Database Biosis "Online!" Biosciences Information Service, Philadelphia, PA 1979, Knight, V. et al., "Amantadine aerosol in humans", database accession No. PREV 198069035552 abstract, &Antimicrobial Agents and Chemotherapy 16(5):572-578.
Database Biosis "Online!" Biosciences Information Service, Philadelphia, PA 1979, Wilson. S.Z. et al., "Amatadine Aerosol Particle Aerosol Generation and Delivery to Man" Database accession No. PREV198069008137, abstract & Proceedings of the Society for Experimental Biology and Medicine 161(3):350-354.
Database WPI, Section CH, Week 198941, Derwent Publications Ltd., London, GB; Class B07, AN 1989-297792 AP002230849 & JP 01 221313 (Nippon Create 1(K), Sep. 4, 1989, abstract.
Davies, C. N. et al. (May 1972). "Breathing of Half-Micron Aerosols," *Journal of Applied Physiology*. 32(5):591-600.
Dershwitz, M., M.D., et al. (Sep. 2000). "Pharmacokinetics and Pharmacodynamics of Inhaled versus Intravenous Morphine in Healthy Volunteers," *Anesthesiology*. 93(3): 619-628.
Drugs Approved by the FDA -Drug Name: Nicotrol Inhaler (2000) located at <http://www.centerwatch.com/patient/drugs/dru202.html> (Visited on Aug. 2, 2001), 2 pages.
Feynman, R.P. et al. (1964). "Chapter 32: Refractive Index of Dense Materials" *The Feyman Lectures on Physics: Mainly Electromagnetism and Matter*. Addison-Wesley: Publishing Company, Inc., Reading, Massachusetts: pp. 32-1-32-13.
Finlay, W. H. (2001). "The Mechanics of Inhaled Pharmaceutical Aerosols", Academic Press: San Diego Formula 2.39. pp. 3-14 (Table of Contents). pp. v-viii.
Gonda, I. (1991). "Particle Deposition in the Human Respiratory Tract,"Chapter 176, *The Lung: Scientific Foundations*. Crystal R.G. and West, J.B. (eds.), Raven Publishers, New York. pp. 2289-2294.
Graves, D. A. et al. (1983). "Patient-Controlled Analgesia," *Annals of Internal Medicine*. 99:360-366.

Anonymous, (Jun. 1998) *Guidance for Industry: Stability testing of drug substances and products*, U.S. Department of Health and Human Services, FDA, CDER, CBER, pp. 1-110.
Hatsukami D., et al. (May 1990) "A Method for Delivery of Precise Doses of Smoked Cocaine-Base to Human." *Pharmacology Biochemistry & Behavior*. 36(1):1-7.
Heyder, J. et al. (1986). "Deposition of Particles in the Human Respiratory Tract in the Size Range 0.005-15 µm," *J. Aerosol Sci.* 17(5):811-822.
Huizer, H. (1987). "Analytical Studies on Illicit Heron. V. Efficacy of Volitization During Heroin Smoking." *Pharmaceutisch Weekblad Scientific Edition*. 9(4):203-211.
Hurt, R. D., MD and Robertson, C. R., PhD, (Oct. 1998). "Prying Open the Door to the Tobacco Industry's Secrets About Nicotine: The Minnesota Tobacco Trial," *JAMA* 280(13):1173-1181.
Hwang, S. L. (Jun. 1999). "Artificial Nicotine Studied: R. J. Reynolds Seeks to Develop Drugs that Mimic Tobacco's Potent Effects on Brain," *Wall Street Journal*, 3 pages.
James, A.C. et al., (1991). "The Respiratory Tract Deposition Model Proposed by the ICRP Task Group," *Radiation Protection Dosimetry*, 38(1/3):159-165.
Kim, M. H. and Patel, D.V. (1994). "'BOP' As a Reagent for Mild and Efficient Preparation of Esters," *Tet. Letters* 35:5603-5606.
Lichtman, A. H. et al. (1996). "Inhalation Exposure to Volatilized Opioids Produces Antinociception in Mice," *Journal of Pharmacology and Experimental Therapeutics*. 279(1):69-76 XP-001118649.
Lichtman, A. H. et al. (2000). "Pharmacological Evaluation of Aerosolized Cannabinoids in Mice" European Journal of Pharmacology, vol. 399, No. 2-3: 141-149.
Lopez, K. (Jul. 1999). "UK Researcher Develops Nicotinic Drugs with R. J. Reynolds," located at <http://www.eurekalert.org/pub_releases/1999-07/UoKM-Urdn-260799.php> (visited on Oct. 1, 2002), 1 page.
Martin, B. R. and Lue, L. P. (May/Jun. 1989). "Pyrolysis and Volatilization of Cocaine," *Journal of Analytical Toxicology* 13:158-162.
Mattox, A.J. and Carroll, M.E. (1996). "Smoked Heroin Self-Administration in Rhesus Monkeys," *Psychopharmacology* 125:195-201.
McCormick, A.S.M., et al., "Bronchospasm During Inhalation of Nebulized Midazolam," *British Journal of Anesthesia*, vol. 80 (4), Apr. 1988, pp. 564-565 XP001119488.
Meng, Y. et al. (1997). "Inhalation Studies with Drugs of Abuse", *NIDA Research Monogragh* 173:201-224.
Meng, Y., et al. (1999). "Pharmacological effects of methamphetamine and other stimulants via inhalation exposure," *Drug and Alcohol Dependence*. 53:111-120.
Office Action mailed Aug. 13, 2003 for U.S. Appl. No. 10/153,313, filed May 21, 2002 "Delivery of Benzodiazepines Through an Inhalation Route".
Office Action mailed Dec. 4, 2003 for U.S. Appl. No. 10/057,198, filed Oct. 26, 2001 "Method and Device for Delivering a Physiologically Active Compound."
Office Action mailed Dec. 15, 2003 for U.S. Appl. No. 10/057,197, filed Oct. 26, 2001 "Aerosol Generating Device and Method".
Pankow, J. F. et al. (1997). "Conversion of Nicotine in Tobacco Smoke to Its Volatile and Available Free-Base Form through the Action of Gaseous Ammonia," *Environ. Sci. Technol*. 31:2428-2433.
Pankow, J. (Mar. 2000). ACS Conference-San Francisco-Mar. 26, 2000. Chemistry of Tobacco Smoke. pp. 1-8.
Poochikian, G. and Bertha, C.M. (2000). "Inhalation Drug Product Excipient Controls: Significance and Pitfalls," *Resp. Drug Deliv.* VII: 109-115.
ScienceDaily Magazine, (Jul. 1999). "University of Kentucky Researcher Develops Nicotinic Drugs with R. J. Reynolds," located at <http://www.sciencedaily.com/releases/1999/07/990728073542.htm.> (visited on Sep. 23, 2002), 2 pages.
Seeman, J. et al. (1999). "The Form of Nicotine in Tobacco. Thermal Transfer of Nicotine and Nicotine Acid Salts to Nicotine in the Gas Phase," *J. Agric. Food Chem*. 47(12):5133-5145.
Sekine, H. and Nakahara, Y. (1987). "Abuse of Smoking Methamphetamine Mixed with Tobacco: 1. Inhalation Efficiency and Pyrolysis Products of Methamphetamine," *Journal of Forensic Science* 32(5):1271-1280.

Streitwieser, A. and Heathcock, C. H. eds., (1981). *Introduction to Organic Chemistry*. Second edition, Macmillan Publishing Co., Inc., New York, pp. ix-xvi. (Table of Contents).

Tsantilis, S. et al. (2001). "Sintering Time for Silica Particle Growth," *Aerosol Science and Technology* 34:237-246.

Vapotronics, Inc. (1998) located at <http://www.vapotronics.com.au/banner.htm.>, 11 pages, (visited on Jun. 5, 2000).

Vaughan, N.P. (1990). "The Generation of Monodisperse Fibres of Caffeine" *J. Aerosol Sci.* 21(3): 453-462.

Ward, M. E. MD, et al. (Dec. 1997). "Morphine Pharmacokinetics after Pulmonary Administration from a Novel Aerosol Delivery System," *Clinical Pharmocology & Therapeutics* 62(6):596-609.

Williams, S. (Feb. 1999). "Rhone-Poulenc Rorer Inc. and Targacept Inc. Announce Alliance to Develop New Drugs to Treat Alzheimer's and Parkinson's Diseases" located at http://www.rpr.rpna.com/ABOUT_RPR/pressrels/1999/990209-targa.html (last visited on Jan. 28, 2000) 1 page.

Wood, R.W. et al. (1996). "Generation of Stable Test Atmospheres of Cocaine Base and Its Pyrolyzate, Methylecgonidine, and Demonstration of Their Biological Activity." *Pharmacology Biochemistry & Behavior*. 55(2):237-248.

Office Action mailed Jan. 26, 2007 with respect to U.S. Appl. No. 10/057,198.

Office Action mailed Jul. 3, 2006 with respect to U.S. Appl. No. 10/057,198.

Office Action mailed Sep. 20, 2005 with respect to U.S. Appl. No. 10/057,198.

Office Action mailed Jan. 12, 2005 with respect to U.S. Appl. No. 10/057,197.

Office Action mailed Jun. 3, 2004 with respect to U.S. Appl. No. 10/057,197.

Office Action mailed Jun. 5, 2007 with respect to U.S. Appl. No. 10/057,197.

Office Action mailed Sep. 21, 2006 with respect to U.S. Appl. No. 10/057,197.

Office Action mailed Feb. 27, 2004 with respect to U.S. Appl. No. 10/146,080.

Office Action mailed Mar. 20, 2007 with respect to U.S. Appl. No. 10/146,080.

Office Action mailed Jun. 5, 2006 with respect to U.S. Appl. No. 10/146,080.

Office Action mailed Aug. 25, 2005 with respect to U.S. Appl. No. 10/146,080.

Office Action mailed Dec. 28, 2007 with respect to U.S. Appl. No. 10/146,080.

Office Action mailed Feb. 12, 2007 with respect to U.S. Appl. No. 10/146,086.

Office Action mailed Oct. 30, 2007 with respect to U.S. Appl. No. 10/146,086.

Office Action mailed Dec. 13, 2005 with respect to U.S. Appl. No. 10/146,086.

Office Action mailed Feb. 16, 2007 with respect to U.S. Appl. No. 10/146,088.

Office Action mailed Sep. 28, 2007 with respect to U.S. Appl. No. 10/146,088.

Office Action mailed Nov. 21, 2007 with respect to U.S. Appl. No. 10/146,088.

Office Action mailed Mar. 8, 2005 with respect to U.S. Appl. No. 10/718,982.

Wood, R.W. et al. (1996). "Methylecgonidine Coats the Crack Particle." Pharmacology Biochemistry & Behavior. 53(1):57-66.

U.S. Appl. No. 12/245,184, filed Oct. 3, 2008, Hale et al.
U.S. Appl. No. 12/211,554, filed Sep. 16, 2008, Sharma et al.
U.S. Appl. No. 12/211,247, filed Sep. 16, 2008, Sharma et al.
U.S. Appl. No. 12/211,628, filed Sep. 16, 2008, Lei et al.
U.S. Appl. No. 11/687,466, filed Mar. 16, 2007, Zaffaroni et al.
U.S. Appl. No. 12/275,836, filed Nov. 21, 2008, Hale et al.
U.S. Appl. No. 12/352,582, filed Jan. 12, 2009, Hale et al.

* cited by examiner

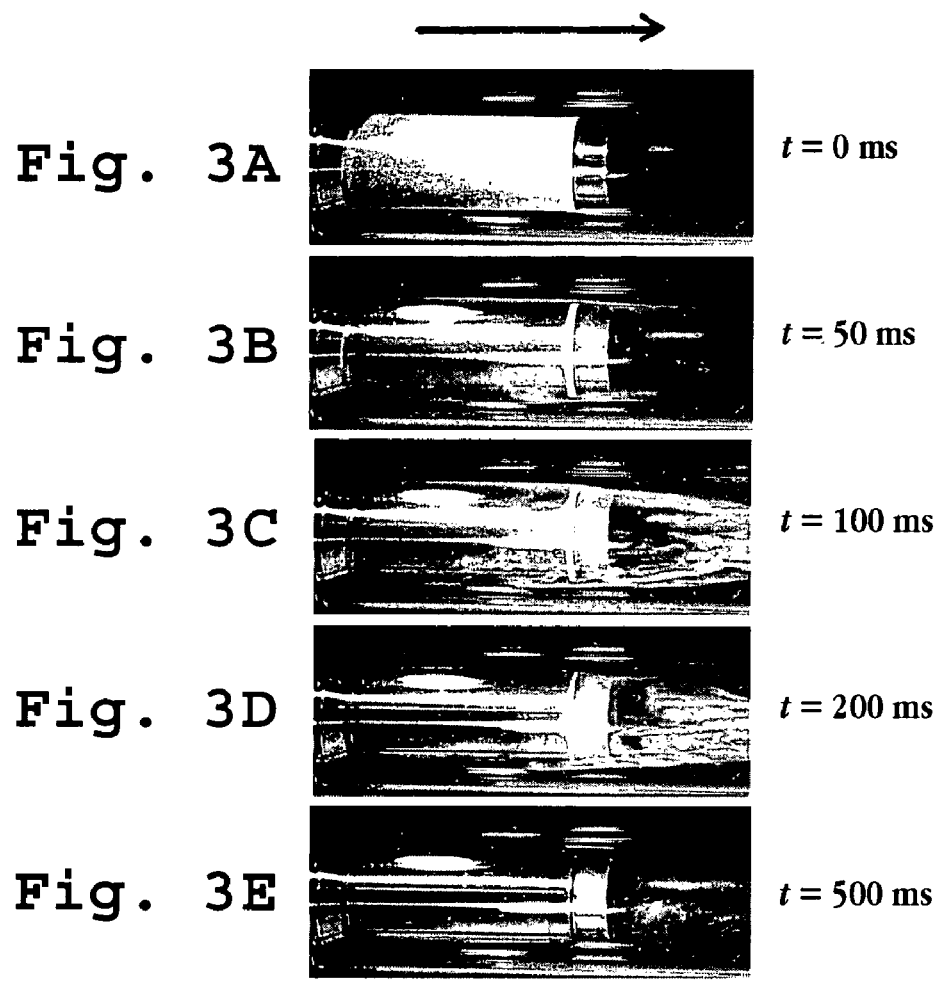
Fig. 3A  t = 0 ms
Fig. 3B  t = 50 ms
Fig. 3C  t = 100 ms
Fig. 3D  t = 200 ms
Fig. 3E  t = 500 ms
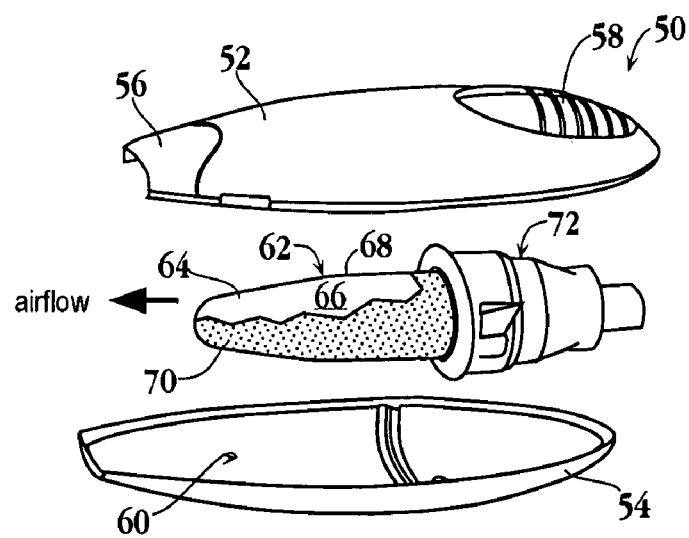
Fig. 2B atropine

Fig. 6 donepezil

Fig. 7

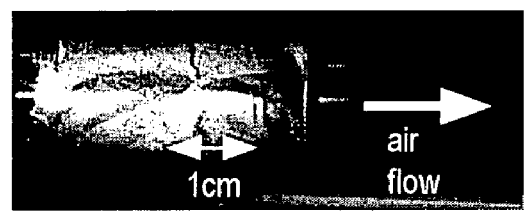
Fig. 24A  t=0 msec
Fig. 24B  t=50 msec
Fig. 24C  t=100 msec
Fig. 24D  t=200 msec t=0 msec t=50 msec t=100 msec t=200 msec t=0 msec t=50 msec t=100 msec t=200 msec t=300 msec

THIN-FILM DRUG DELIVERY ARTICLE AND METHOD OF USE

The present application is a continuation-in-part of application Ser. No. 10/057,197, filed Oct. 26, 2001, which claims benefit of Provisional Application No. 60/296,225, filed Jun. 5, 2001.

This application is also a continuation-in-part of application Ser. No. 10/057,198, filed Oct. 26, 2001, which claims benefit of Provisional Application No. 60/296,225, filed Jun. 5, 2001.

This application is also a continuation-in-part of application Ser. No. 10/146,080, filed May 13, 2002, which is a continuation-in-part of application Ser. No. 10/057,198, filed Oct. 26, 2001, which claims the benefit of Provisional Application No. 60/296,225, filed Jun. 5, 2001. This Application is also a continuation-in-part of application Ser. No. 10/057,197, filed Oct. 26, 2001, which claims the benefit of Provisional Application No. 60/296,225, filed Jun. 5, 2001.

This application is also a continuation-in-part of application Ser. No. 10/146,086, filed May 13, 2002.

This application is also a continuation-in-part of application Ser. No. 10/146,088, filed May 13, 2002, which is a continuation-in-part of patent application Ser. No. 10/057,198, filed Oct. 26, 2001, which claims the benefit of Provisional Application No. 60/296,225, filed Jun. 5, 2001. This application is also a continuation-in-part of patent application Ser. No. 10/057,197, filed Oct. 26, 2001, which claims the benefit of Provisional Application No. 60/296,225, filed Jun. 5, 2001.

This application is also a continuation-in-part of application Ser. No. 10/146,515, filed May 13, 2002, now U.S. Pat. No. 6,682,716, which is a continuation-in-part of patent application Ser. No. 10/057,198, filed Oct. 26, 2001, which claims the benefit of Provisional Application No. 60/296,225, filed Jun. 5, 2001. This application is also a continuation-in-part of patent application Ser. No. 10/057,197, filed Oct. 26, 2001, which claims the benefit of Provisional Application No. 60/296,225, filed Jun. 5, 2001.

This application is also a continuation-in-part of application Ser. No. 10/146,516, filed May 13, 2002, now U.S. Pat. No. 6,737,042, which claims the benefit of Provisional Application No. 60/294,203, filed May 24, 2001, and also claims the benefit of Provisional Application No. 60/317,479, file Sep. 5, 2001.

This application is also a continuation-in-part of application Ser. No. 10/150,056, filed May 15, 2002, now U.S. Pat. No. 6,805,853, which claims the benefit of Provisional Application No. 60/345,882, filed Nov. 9, 2001.

This application is also a continuation-in-part of application Ser. No. 10/150,267, filed May 15, 2002, now U.S. Pat. No. 6,797,259, which claims the benefit of Provisional Application No. 60/294,203, filed May 24, 2001, and of Provisional Application No. 60/317,479, filed Sep. 5, 2001.

This application is also a continuation-in-part of application Ser. No. 10/150,268, filed May 15, 2002, now U.S. Pat. No. 6,780,399, which claims the benefit of Provisional Application No. 60/294,203, filed May 24, 2001, and of Provisional Application No. 60/317,479, filed Sep. 5, 2001.

This application is also a continuation-in-part of application Ser. No. 10/150,591, filed May 17, 2002, now U.S. Pat. No. 6,780,400, which claims the benefit of Provisional Application No. 60/294,203, filed May 24, 2001, and of Provisional Application No. 60/317,479, filed Sep. 5, 2001.

This application is also a continuation-in-part of application Ser. No. 10/150,857, filed May 17, 2002, now U.S. Pat. No. 6,716,415, which claims the benefit of Provisional Application No. 60/294,203, filed May 24, 2001, and of Provisional Application No. 60/317,479, filed Sep. 5, 2001.

This application is also a continuation-in-part of application Ser. No. 10/151,596, filed May 16, 2002, now U.S. Pat. No. 6,855,310, which claims the benefit of Provisional Application. No. 60/294,203, filed May 24, 2001, and of Provisional Application No. 60/317,479, filed Sep. 5, 2001.

This application is also a continuation-in-part of application Ser. No. 10/151,626, filed May 16, 2002, now U.S. Pat. No. 6,783,753, which claims the benefit of Provisional Application No. 60/294,203, filed May 24, 2001, and of Provisional Application No. 60/317,479, filed Sep. 5, 2001.

This application is also a continuation-in-part of application Ser. No. 10/152,639, filed May 20, 2002, now U.S. Pat. No. 6,716,416, which claims the benefit of Provisional Application No. 60/294,203, filed May 24, 2001, and of Provisional Application No. 60/317,479, filed Sep. 5, 2001.

This application is also a continuation-in-part of application Ser. No. 10/152,640, filed May 20, 2002, now U.S. Pat. No. 6,743,415, which claims the benefit of Provisional Application No. 60/294,203, filed May 24, 2001, and pr Provisional Application No. 60/317,479, filed Sep. 5, 2001.

This application is also a continuation-in-part of application Ser. No. 10/152,652, filed May 20, 2002, now U.S. Pat. No. 6,740,307, which claims the benefit of Provisional Application No. 60/294,203, filed May 24, 2001, and of Provisional Application No. 60/317,479, filed Sep. 5, 2001.

This application is also a continuation-in-part of application Ser. No. 10/153,139, filed May 20, 2002, now U.S. Pat. No. 6,814,954, which claims the benefit of Provisional Application No. 60/294,203, filed May 24, 2001, and of Provisional Application No. 60/317,479, filed Sep. 5, 2001.

This application is also a continuation-in-part of application Ser. No. 10/153,311, filed May 21, 2002, now U.S. Pat. No. 6,884,408, which claims the benefit of Provisional Application No. 60/294,203, filed May 24, 2001, and of Provisional Application No. 60/317,479, filed Sep. 5, 2001.

This application is also a continuation-in-part of application Ser. No. 10/153,313, filed May 20, 2002, now abandoned which claims the benefit of Provisional Application No. 60/294,203, filed May 24, 2001, and of Provisional Application No. 60/317,479, filed Sep. 5, 2001, and of Provisional Application No. 60/345,145, filed Nov. 9, 2001.

This application is also a continuation-in-part of application Ser. No. 10/153,831, filed May 21, 2002, now U.S. Pat. No. 6,740,308, which claims the benefit of Provisional Application No. 60/294,203, filed May 24, 2001, and of Provisional Application No. 60/317,479, filed Sep. 5, 2001.

This application is also a continuation-in-part of application Ser. No. 10/153,839, filed May 21, 2002, now U.S. Pat. No. 6,776,978, which claims the benefit of Provisional Application No. 60/294,203, filed May 24, 2001, and of Provisional Application No. 60/317,479, filed Sep. 5, 2001.

This application is also a continuation-in-part of application Ser. No. 10/154,594, filed May 23, 2002, now U.S. Pat. No. 6,740,309, which claims the benefit of Provisional Application No. 60/294,203, filed May 24, 2001, and of Provisional Application No. 60/317,479, filed Sep. 5, 2001.

This application is also a continuation-in-part of application Ser. No. 10/154,765, filed May 23, 2002, now U.S. Pat. No. 6,814,955, which claims the benefit of Provisional Application No. 60/294,203, filed May 24, 2001, and of Provisional Application No. 60/317,479, filed Sep. 5, 2001.

This application is also a continuation-in-part of application Ser. No. 10/155,097, filed May 23, 2002, now U.S. Pat. No. 6,716,417, which claims the benefit of Provisional Application No. 60/294,203, filed May 24, 2001, and of Provisional Application No. 60/317,479, filed Sep. 5, 2001.

This application is also a continuation-in-part of application Ser. No. 10/155,373, filed May 22, 2002, now U.S. Pat. No. 6,737,043, which claims the benefit of Provisional Application No. 60/294,203, filed May 24, 2001, and of Provisional Application No. 60/317,479, filed Sep. 5, 2001, and of Provisional Application No. 60/345,876, filed Nov. 9, 2001.

This application is also a continuation-in-part of application Ser. No. 10/155,621, filed May 22, 2002, now U.S. Pat. No. 6,759,029, which claims the benefit of Provisional Application No. 60/294,203, filed May 24, 2001, and of Provisional Application No. 60/317,479, filed Sep. 5, 2001, and of Provisional Application No. 60/332,280, filed Nov. 21, 2001, and of Provisional Application No. 60/336,218, filed Oct. 30, 2001.

This application is also a continuation-in-part of application Ser. No. 10/155,703, filed May 22, 2002, now U.S. Pat. No. 6,803,031, which claims the benefit of Provisional Application No. 60/294,203, filed May 24, 2001, and of Provisional Application No. 60/317,479, filed Sep. 5, 2001.

This application is also a continuation-in-part of application Ser. No. 10/155,705, filed May 22, 2002, now U.S. Pat. No. 6,805,854, which claims the benefit of Provisional Application No. 60/294,203, filed May 24, 2001, and of Provisional Application No. 60/317,479, filed Sep. 5, 2001.

This application is also a continuation-in-part of application Ser. No. 10/280,315, filed Oct. 25, 2002, now abandoned which claims the benefit of Provisional Application No. 60/335,049, filed Oct. 30, 2001, and of Provisional Application No. 60/371,457, filed Apr. 9, 2002.

This application is also a continuation-in-part of application Ser. No. 10/302,010, filed Nov. 21, 2002, now U.S. Pat. No. 7,078,016, which claims the benefit of Provisional Application No. 60/332,279, filed Nov. 21, 2001.

This application is also a continuation-in-part of application Ser. No. 10/302,614, filed Nov. 21, 2002, which claims the benefit of Provisional Application No. 60/332,165, filed Nov. 21, 2001.

This application is also a continuation-in-part of application Ser. No. 10/322,227, filed Dec. 17, 2002, now abandoned which claims the benefit of Provisional Application No. 60/342,066, filed Dec. 18, 2001, and of Provisional Application No. 60/412,068, filed Sep. 18, 2002.

All of the applications cited above are incorporated by reference in their entirety. This invention was made with Government support under Grant No. R44 NS044800, awarded by the National Institutes of Health. The Government has certain rights in the invention.

FIELD OF THE INVENTION

The present invention relates generally to the field of devices and methods for administration of pharmaceutically-active drugs. More specifically, the invention relates to a drug-supply device for use in production of drug-aerosol particles.

BACKGROUND OF THE INVENTION

Traditionally, inhalation therapy has played a relatively minor role in the administration of therapeutic agents when compared to more traditional drug administration routes of oral delivery and delivery via injection. Due to drawbacks associated with traditional routes of administration, including slow onset, poor patient compliance, inconvenience, and/or discomfort, alternative administration routes have been sought. Pulmonary delivery is one such alternative administration route which can offer several advantages over the more traditional routes. These advantages include rapid onset, the convenience of patient self-administration, the potential for reduced drug side-effects, ease of delivery by inhalation, the elimination of needles, and the like. Many preclinical and clinical studies with inhaled compounds have demonstrated that efficacy can be achieved both within the lungs and systemically.

However, despite such results, the role of inhalation therapy in the health care field has remained limited mainly to treatment of asthma, in part due to a set of problems unique to the development of inhalable drug formulations, especially formulations for systemic delivery by inhalation. Dry powder formulations, while offering advantages over cumbersome liquid dosage forms and propellant-driven formulations, are prone to aggregation and low flowability phenomena which considerably diminish the efficiency of dry powder-based inhalation therapies.

Thus, there remains a need in the art for devices capable of producing a drug aerosol for delivery by, for example, inhalation or topical application.

SUMMARY OF THE INVENTION

In one aspect, the invention includes an article for use in an aerosol device, for producing an aerosol of a compound, comprising (a) a heat-conductive substrate having an exterior surface expanse with a selected surface area, and (b) formed over the surface expanse, a film containing the compound and having a selected film thickness of between 0.05 μm and 20 μm. The film thickness is such that an aerosol formed by vaporizing the compound by heating the substrate and condensing the vaporized compound contains 10% by weight or less drug-degradation product and at least 50% of the total amount of compound contained in the film. The selected area of the substrate surface expanse is such as to yield an effective human therapeutic dose of the drug aerosol.

The film thickness may be selected such that the compound can be volatilized from the substrate with less than about 5% by weight compound degradation.

In a preferred embodiment, the selected substrate surface area is between about 0.05-100 $cm^2$. The substrate may have an impermeable surface expanse on which film of the compound is formed. Exemplary substrates are formed of metals, such as stainless steel or aluminum, polymers, ceramics, and/or glass. Alternatively, or in addition, the substrate surface expanse is characterized by a contiguous surface area of greater than 1 $mm^2$, preferably 10 $mm^2$, more preferable 50 $mm^2$ and still more preferably 100 $mm^2$, and a material density of greater than 0.5 g/cc.

The compound may be one that, when vaporized from a compound film formed on an impermeable surface expanse of a heat conductive substrate and condensed to form aerosol particles, under selected vaporization conditions that lead to at least 50% recovery of compound in the aerosol particles, exhibits (i) less than about 5% degradation product in aerosol particles when the compound is vaporized from a film having a selected film thickness between 0.05 and 20 microns, and (ii) increasing levels of compound degradation in the aerosol particles, with increasing film thickness above the selected film thickness.

Exemplary compounds for use in the invention, and corresponding film thickness ranges are:

alprazolam, film thickness between 0.1 and 10 μm;
amoxapine, film thickness between 2 and 20 μm;
atropine, film thickness between 0.1 and 10 μm;

bumetanide film thickness between 0.1 and 5 μm;
buprenorphine, film thickness between 0.05 and 10 μm;
butorphanol, film thickness between 0.1 and 10 μm;
clomipramine, film thickness between 1 and 8 μm;
donepezil, film thickness between 1 and 10 μm;
hydromorphone, film thickness between 0.05 and 10 μm;
loxapine, film thickness between 1 and 20 μm;
midazolam, film thickness between 0.05 and 20 μm;
morphine, film thickness between 0.2 and 10 μm;
nalbuphine, film thickness between 0.2 and 5 μm;
naratriptan, film thickness between 0.2 and 5 μm;
olanzapine, film thickness between 1 and 20 μm;
paroxetine, film thickness between 1 and 20 μm;
prochlorperazine, film thickness between 0.1 and 20 μm;
quetiapine, film thickness between 1 and 20 μm;
sertraline, film thickness between 1 and 20 μm;
sibutramine, film thickness between 0.5 and 2 μm;
sildenafil, film thickness between 0.2 and 3 μm;
sumatriptan, film thickness between 0.2 and 6 μm;
tadalafil, film thickness between 0.2 and 5 μm;
vardenafil, film thickness between 0.1 and 2 μm;
venlafaxine, film thickness between 2 and 20 μm;
zolpidem, film thickness between 0.1 and 10 μm;
apomorphine HCl, film thickness between 0.1 and 5 μm;
celecoxib, film thickness between 2 and 20 μm;
ciclesonide, film thickness between 0.05 and 5 μm;
eletriptan, film thickness between 0.2 and 20 μm;
parecoxib, film thickness between 0.5 and 2 μm;
valdecoxib, film thickness between 0.5 and 10 μm; and
fentanyl, film thickness between 0.05 and 5 μm.

The article may be formed, in accordance with another aspect of the invention, by first determining, for a selected compound, a film thickness between 0.05 nd 20 microns such that an aerosol formed by (i) vaporizing the compound by heating a heat-conductive substrate having an exterior surface expanse and a film of the compound formed on the surface expanse to vaporize the compound and (ii) condensing the vaporized compound contains 10% by weight or less drug-degradation product and at least 50% of the total amount of drug composition contained in the film. There is then determined an area of surface expanse, when a film of the drug composition of the determined thickness is applied to the area, accommodating an effective human therapeutic inhalation dose of the drug. A film of the selected drug of the identified thickness is then formed over the determined substrate area. Certain embodiments of the method are as described above.

In a related aspect, the invention includes a method of forming an effective human therapeutic inhalation dose of a drug composition in aerosol form having 10% or less drug-degradation products and a selected aerosol particle mass median aerodynamic diameter (MMAD) between about 0.01 and 3 μm. The method involves the steps of heating the substrate in the article of claim 1 to a temperature between 300° C. and 500° C., thereby to vaporize the film of drug composition formed on the substrate, and during this heating, flowing a gas across the substrate at a gas flow rate effective to produce the desired size aerosol particles by condensation of the vaporized drug composition.

The heating step may be effective to vaporize the film of drug composition on the substrate within a time period of 2 seconds or less, e.g., 0.5 sec. The flowing step may be carried out at a gas flow rate of between about 4 and 50 L/minutes. Rapid heating in combination with the air flow helps reduce the amount of decomposition. Rapid generation of the aerosol is also necessary to ensure consistent delivery of an amount of drug to the deep lung. To deliver a drug in a single bolus requires that the drug be delivered in a single inhalation breath and preferably at the earliest stages of the breath, particularly as the time period for a breath can vary from individual to individual. The use of thin films allows a more rapid rate of vaporization. Thus, rapid heating and generation of the aerosol provides a means to deliver a consistent dose to the deep lung in a single breath. Other embodiments of the method are as described above.

In still another aspect of the invention, a method of forming an article for use in an aerosol device, for producing aerosol particles of a drug composition, is provided. The method includes (a) preparing on a heat-conductive impermeable substrate a film containing a drug composition and having a first film thickness; (b) heating said substrate to vaporize said film, thereby producing aerosol particles containing said drug composition; (c) determining (i) the drug purity of said aerosol particles and (ii) the fraction of film vaporized, and (d) repeating steps (a)-(c) one or more times but at a film thickness different from the first film thickness to achieve an aerosol particle purity of at least about 90% and a fraction of drug film vaporized of at least about 50%.

In one embodiment of this method, the step of determining further comprises selecting drug compositions having an aerosol particle purity of equal to or greater than 60% but less than 90% and a fraction of film vaporized of greater than 30% for the step of repeating (step (d)).

In another embodiment, the step of preparing includes preparing a film of the therapeutic drug composition on a selected surface area of the substrate sufficient to provide a therapeutic dose of drug composition in the form of aerosol particles.

In one embodiment, the step of repeating includes heating the substrate in an inert atmosphere, such as an argon or nitrogen atmosphere.

In another embodiment, the step of preparing comprises preparing a film having a first film thickness of between about 1-20 μm. The step of repeating comprises preparing a film having a different film thickness of between about 0.05-10 μm.

These and other objects and features of the invention will be more fully appreciated when the following detailed description of the invention is read in conjunction with the accompanying drawings.

BRIEF DESCRIPTION OF THE DRAWINGS

FIG. 2B shows another drug-delivery device that incorporates a drug-supply article, where the device components are shown in unassembled form;

FIGS. 3A-3E are high speed photographs showing the generation of aerosol particles from a drug-supply unit;

FIG. 5A shows the temperature profile over a 4 second time period and FIG. 5B is a detail showing the temperature profile over the first second of heating;

FIG. 6 is plot showing purity of thermal vapor as a function of drug film thickness, in micrometers, for the drug atropine free base;

FIG. 7 is plot showing purity of thermal vapor as a function of drug film thickness, in micrometers, for donepezil free base;

FIGS. 24A-24D are high speed photographs showing the generation of a thermal vapor of phenytoin from a film of drug coated on a substrate drug-supply unit, where the photographs are taken prior to substrate heating (t=0 ms, FIG. 24A) and during substrate heating at times of 50 milliseconds (FIG. 24B), 100 milliseconds (FIG. 24C), and 200 milliseconds (FIG. 24D);

DETAILED DESCRIPTION OF THE INVENTION

I. Definitions

Figure 1A:
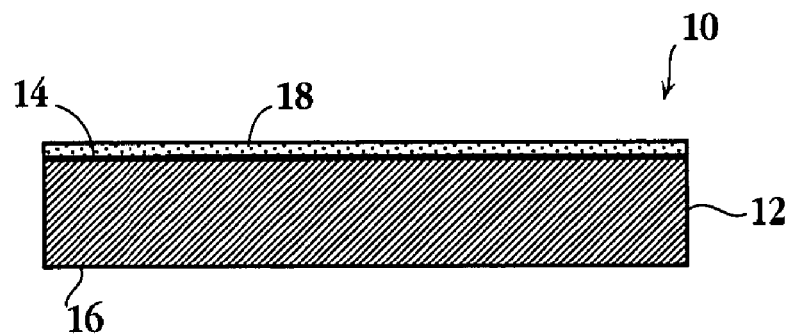
FIGS. 1A-1B are cross-sectional views of general embodiments of a drug-supply article in accordance with the invention.

The term "drug" as used herein means any substance that is used in the prevention, diagnosis, alleviation, treatment or cure of a condition. The drug is preferably in a form suitable for thermal vapor delivery, such as an ester, free acid, or free base form. The drugs are preferably other than recreational drugs. More specifically, the drugs are preferably other than recreational drugs used for non-medicinal recreational purposes, e.g., habitual use to solely alter one's mood, affect, state of consciousness, or to affect a body function unnecessarily, for recreational purposes. The terms "drug", "compound", and "medication" are herein used interchangeably.

The drugs of use in the invention typically have a molecular weight in the range of about 150-700, preferably in the range of about 200-650, more preferably in the range of 250-600, still more preferably in the range of about 250-500, and most preferably in the range of about 300-450.

Specific drugs that can be used include, for example but not limitation, drugs of one of the following classes: anesthetics, anticonvulsants, antidepressants, antidiabetic agents, antidotes, antiemetics, antihistamines, anti-infective agents, antineoplastics, antiparkisonian drugs, antirheumatic agents, antipsychotics, anxiolytics, appetite stimulants and suppressants, blood modifiers, cardiovascular agents, central nervous system stimulants, drugs for Alzheimer's disease management, drugs for cystic fibrosis management, diagnostics, dietary supplements, drugs for erectile dysfunction, gastrointestinal agents, hormones, drugs for the treatment of alcoholism, drugs for the treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, opthalmic preparations, osteoporosis preparations, prostaglandins, respiratory agents, sedatives and hypnotics, skin and mucous membrane agents, smoking cessation aids, Tourette's syndrome agents, urinary tract agents, and vertigo agents.

Typically, where the drug is an anesthetic, it is selected from one of the following compounds: ketamine and lidocaine.

Typically, where the drug is an anticonvulsant, it is selected from one of the following classes: GABA analogs, tiagabine, vigabatrin; barbiturates such as pentobarbital; benzodiazepines such as clonazepam; hydantoins such as phenytoin; phenyltriazines such as lamotrigine; miscellaneous anticonvulsants such as carbamazepine, topiramate, valproic acid, and zonisamide.

Typically, where the drug is an antidepressant, it is selected from one of the following compounds: amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, venlafaxine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, tofenacin, trazodone, tryptophan, and zalospirone.

Typically, where the drug is an antidiabetic agent, it is selected from one of the following compounds: pioglitazone, rosiglitazone, and troglitazone.

Typically, where the drug is an antidote, it is selected from one of the following compounds: edrophonium chloride, flumazenil, deferoxamine, nalmefene, naloxone, and naltrexone.

Typically, where the drug is an antiemetic, it is selected from one of the following compounds: alizapride, azasetron, benzquinamide, bromopride, buclizine, chlorpromazine, cinnarizine, clebopride, cyclizine, diphenhydramine, diphenidol, dolasetron, droperidol, granisetron, hyoscine, lorazepam, dronabinol, metoclopramide, metopimazine, ondansetron, perphenazine, promethazine, prochlorperazine, scopolamine, triethylperazine, trifluoperazine, triflupromazine, trimethobenzamide, tropisetron, domperidone, and palonosetron.

Typically, where the drug is an antihistamine, it is selected from one of the following compounds: astemizole, azatadine, brompheniramine, carbinoxamine, cetrizine, chlorpheniramine, cinnarizine, clemastine, cyproheptadine, dexmedetomidine, diphenhydramine, doxylamine, fexofenadine, hydroxyzine, loratidine, promethazine, pyrilamine and terfenidine.

Typically, where the drug is an anti-infective agent, it is selected from one of the following classes: antivirals such as efavirenz; AIDS adjunct agents such as dapsone; aminoglycosides such as tobramycin; antifungals such as fluconazole; antimalarial agents such as quinine; antituberculosis agents such as ethambutol; β-lactams such as cefinetazole, cefazolin, cephalexin, cefoperazone, cefoxitin, cephacetrile, cephaloglycin, cephaloridine; cephalosporins, such as cephalosporin C, cephalothin; cephamycins such as cephamycin A, cephamycin B, and cephamycin C, cephapirin, cephradine; leprostatics such as clofazimine; penicillins such as ampicillin, amoxicillin, hetacillin, carfecillin, carindacillin, carbenicillin, amylpenicillin, azidocillin, benzylpenicillin, clometocillin, cloxacillin, cyclacillin, methicillin, nafcillin, 2-pentenylpenicillin, penicillin N, penicillin O, penicillin S, penicillin V, dicloxacillin; diphenicillin; heptylpenicillin; and metampicillin; quinolones such as ciprofloxacin, clinafloxacin, difloxacin, grepafloxacin, norfloxacin, ofloxacine, temafloxacin; tetracyclines such as doxycycline and oxytetracycline; miscellaneous anti-infectives such as linezolide, trimethoprim and sulfamethoxazole.

Typically, where the drug is an anti-neoplastic agent, it is selected from one of the following compounds: droloxifene, tamoxifen, and toremifene.

Typically, where the drug is an antiparkisonian drug, it is selected from one of the following compounds: amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinerole, selegiline, spheramine, terguride, entacapone, and tolcapone.

Typically, where the drug is an antirheumatic agent, it is selected from one of the following compounds: diclofenac, hydroxychloroquine and methotrexate.

Typically, where the drug is an antipsychotic, it is selected from one of the following compounds: acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine, and zuclopenthixol.

Typically, where the drug is an anxiolytic, it is selected from one of the following compounds: alprazolam, bromazepam, oxazepam, buspirone, hydroxyzine, mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, captodiamine, capuride, carbcloral, carbromal, chloral betaine, encirpazine, flesinoxan, ipsapiraone, lesopitron, loxapine, methaqualone, methprylon, propanolol, tandospirone, trazadone, zopiclone, and zolpidem.

Typically, where the drug is an appetite stimulant, it is dronabinol.

Typically, where the drug is an appetite suppressant, it is selected from one of the following compounds: fenfluramine, phentermine and sibutramine.

Typically, where the drug is a blood modifier, it is selected from one of the following compounds: cilostazol and dipyridamol.

Typically, where the drug is a cardiovascular agent, it is selected from one of the following compounds: benazepril, captopril, enalapril, quinapril, ramipril, doxazosin, prazosin, clonidine, labetolol, candesartan, irbesartan, losartan, telmisartan, valsartan, disopyramide, flecanide, mexiletine, procainamide, propafenone, quinidine, tocainide, amiodarone, dofetilide, ibutilide, adenosine, gemfibrozil, lovastatin, acebutalol, atenolol, bisoprolol, esmolol, metoprolol, nadolol, pindolol, propranolol, sotalol, diltiazem, nifedipine, verapamil, spironolactone, burnetanide, ethacrynic acid, furosemide, torsemide, amiloride, triamterene, and metolazone.

Typically, where the drug is a central nervous system stimulant, it is selected from one of the following compounds: amphetamine, brucine, caffeine, dexfenfluramine, dextroamphetamine, ephedrine, fenfluramine, mazindol, methyphenidate, pemoline, phentermine, sibutramine, and modafinil.

Typically, where the drug is a drug for Alzheimer's disease management, it is selected from one of the following compounds: donepezil, galanthamine and tacrin.

Typically, where the drug is a drug for cystic fibrosis management, it is selected from one of the following compounds: tobramycin and cefadroxil.

Typically, where the drug is a diagnostic agent, it is selected from one of the following compounds: adenosine and aminohippuric acid.

Typically, where the drug is a dietary supplement, it is selected from one of the following compounds: melatonin and vitamin-E.

Typically, where the drug is a drug for erectile dysfunction, it is selected from one of the following compounds: tadalafil, sildenafil, vardenafil, apomorphine, apomorphine diacetate, phentolamine, and yohimbine.

Typically, where the drug is a gastrointestinal agent, it is selected from one of the following compounds: loperamide, atropine, hyoscyamine, famotidine, lansoprazole, omeprazole, and rebeprazole.

Typically, where the drug is a hormone, it is selected from one of the following compounds: testosterone, estradiol, and cortisone.

Typically, where the drug is a drug for the treatment of alcoholism, it is selected from one of the following compounds: naloxone, naltrexone, and disulfiram.

Typically, where the drug is a drug for the treatment of addiction it is buprenorphine.

Typically, where the drug is an immunosupressive, it is selected from one of the following compounds: mycophenolic acid, cyclosporin, azathioprine, tacrolimus, and rapamycin.

Typically, where the drug is a mast cell stabilizer, it is selected from one of the following compounds: cromolyn, pemirolast, and nedocromil.

Typically, where the drug is a drug for migraine headache, it is selected from one of the following compounds: almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Typically, where the drug is a motion sickness product, it is selected from one of the following compounds: diphenhydramine, promethazine, and scopolamine.

Typically, where the drug is a drug for multiple sclerosis management, it is selected from one of the following compounds: bencyclane, methylprednisolone, mitoxantrone, and prednisolone.

Typically, where the drug is a muscle relaxant, it is selected from one of the following compounds: baclofen, chlorzoxazone, cyclobenzaprine, methocarbamol, orphenadrine, quinine, and tizanidine.

Typically, where the drug is a nonsteroidal anti-inflammatory, it is selected from one of the following compounds: aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib.

Typically, where the drug is an opioid, it is selected from one of the following compounds: alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Typically, where the drug is an other analgesic it is selected from one of the following compounds: apazone, benzpiperylon, benzydramine, caffeine, clonixin, ethoheptazine, flupirtine, nefopam, orphenadrine, propacetamol, and propoxyphene.

Typically, where the drug is an opthalmic preparation, it is selected from one of the following compounds: ketotifen and betaxolol.

Typically, where the drug is an osteoporosis preparation, it is selected from one of the following compounds: alendronate, estradiol, estropitate, risedronate and raloxifene.

Typically, where the drug is a prostaglandin, it is selected from one of the following compounds: epoprostanol, dinoprostone, misoprostol, and alprostadil.

Typically, where the drug is a respiratory agent, it is selected from one of the following compounds: albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, and zafirlukast.

Typically, where the drug is a sedative and hypnotic, it is selected from one of the following compounds: butalbital, chlordiazepoxide, diazepam, estazolam, flunitrazepam, flurazepam, lorazepam, midazolam, temazepam, triazolam, zaleplon, zolpidem, and zopiclone.

Typically, where the drug is a skin and mucous membrane agent, it is selected from one of the following compounds: isotretinoin, bergapten and methoxsalen.

Typically, where the drug is a smoking cessation aid, it is selected from one of the following compounds: nicotine and varenicline.

Typically, where the drug is a Tourette's syndrome agent, it is pimozide.

Typically, where the drug is a urinary tract agent, it is selected from one of the following compounds: tolteridine, darifenicin, propantheline bromide, and oxybutynin.

Typically, where the drug is a vertigo agent, it is selected from one of the following compounds: betahistine and meclizine.

The term "drug composition" as used herein refers to a composition that comprises only pure drug, two or more drugs in combination, or one or more drugs in combination with additional components. Additional components can include, for example, pharmaceutically acceptable excipients, carriers, and surfactants.

The term "thermal vapor" as used herein refers to a vapor phase, aerosol, or mixture of aerosol-vapor phases, formed preferably by heating. The thermal vapor may comprise a drug and optionally a carrier, and may be formed by heating the drug and optionally a carrier. The term "vapor phase" refers to a gaseous phase. The term "aerosol phase" refers to solid and/or liquid particles suspended in a gaseous phase.

The term "drug degradation product" as used herein refers to a compound resulting from a chemical modification of the drug compound during the drug vaporization-condensation process. The modification, for example, can be the result of a thermally or photochemically induced reaction. Such reactions include, without limitation, oxidation and hydrolysis.

The term "fraction drug degradation product" as used herein refers to the quantity of drug degradation products present in the aerosol particles divided by the quantity of drug plus drug degradation product present in the aerosol, i.e. (sum of quantities of all drug degradation products present in the aerosol)/((quantity of drug composition present in the aerosol)+(sum of quantities of all drug degradation products present in the aerosol)). The term "percent drug degradation product" as used herein refers to the fraction drug degradation product multiplied by 100%, whereas "purity" of the aerosol refers to 100% minus the percent drug degradation products. To determine the percent or fraction drug degradation product, typically, the aerosol is collected in a trap, such as a filter, glass wool, an impinger, a solvent trap, or a cold trap, with collection in a filter particularly preferred. The trap is then typically extracted with a solvent, e.g. acetonitrile, and the extract subjected to analysis by any of a variety of analytical methods known in the art, with gas and liquid chromatography preferred methods, and high performance liquid chromatography particularly preferred. The gas or liquid chromatography method includes a detector system, such as a mass spectrometry detector or ultraviolet absorption detector. Ideally, the detector system allows determination of the quantity of the components of the drug composition and drug degradation product by weight. This is achieved in practice by measuring the signal obtained upon analysis of one or more known mass(es) of components of the drug composition or drug degradation product (standards) and comparing the signal obtained upon analysis of the aerosol to that obtained upon analysis of the standard(s), an approach well known in the art. In many cases, the structure of a drug degradation product may not be known or a standard of the drug degradation product may not be available. In such cases, it is acceptable to calculate the weight fraction of the drug degradation product by assuming that the drug degradation product has an identical response coefficient (e.g. for ultraviolet absorption detection, identical extinction coefficient) to the drug component or components in the drug composition. When conducting such analysis, for practicality drug degradation products present at less than a very small fraction of the drug compound, e.g. less than 0.2% or 0.1% or 0.03% of the drug compound, are generally excluded from analysis. Because of the frequent necessity to assume an identical response coefficient between drug and drug degradation product in calculating a weight percentage of drug degradation product, it is preferred to use an analytical approach in which such an assumption has a high probability of validity. In this respect, high performance liquid chromatography with detection by absorption of ultraviolet light at 225 nm is a preferred approach. UV absorption at other than 225 nm, most commonly 250 nm, was used for detection of compounds in limited cases where the compound absorbed substantially more strongly at 250 nm or for other reasons one skilled in the art would consider detection at 250 nm the most appropriate means of estimating purity by weight using HPLC analysis. In certain cases where analysis of the drug by UV was not viable, other analytical tools such as GC/MS or LC/MS were used to determine purity.

The term "effective human therapeutic dose" means the amount required to achieve the desired effect or efficacy, e.g., abatement of symptoms or cessation of the episode, in a human. The dose of a drug delivered in the thermal vapor refers to a unit dose amount that is generated by heating of the drug under defined delivery conditions. A "unit dose amount" is the total amount of drug in a given volume of inhaled thermal vapor. The unit dose amount may be determined by collecting the thermal vapor and analyzing its composition as described herein, and comparing the results of analysis of the thermal vapor to those of a series of reference standards containing known amounts of the drug. The amount of drug or drugs required in the starting composition for delivery as a thermal vapor depends on the amount of drug or drugs entering the thermal vapor phase when heated (i.e., the dose produced by the starting drug or drugs), the bioavailability of the thermal vapor phase drug or drugs, the volume of patient inhalation, and the potency of the thermal vapor drug or drugs as a function of plasma drug concentration.

Typically, the bioavailability of thermal vapors ranges from 20-100% and is preferably in the range of 50-100% relative to the bioavailability of drugs infused intravenously. The potency of the thermal vapor drug or drugs per unit plasma drug concentration is preferably equal to or greater than that of the drug or drugs delivered by other routes of administration. It may substantially exceed that of oral, intramuscular, or other routes of administration in cases where the clinical effect is related to the rate of rise in plasma drug concentration more strongly than the absolute plasma drug concentration. In some instances, thermal vapor delivery results in increased drug concentration in a target organ such as the brain, relative to the plasma drug concentration (Lichtman et al., *The Journal of Pharmacology and Experimental Therapeutics* 279:69-76 (1996)). Thus, for medications currently given orally, the human dose or effective therapeutic amount of that drug in thermal vapor form is generally less than the standard oral dose. Preferably it will be less than 80%, more preferably less than 40%, and most preferably less than 20% of the standard oral dose. For medications currently given intravenously, the drug dose in a thermal vapor will generally be similar to or less than the standard intravenous dose. Preferably it will be less than 200%, more preferably less than 100%, and most preferably less than 50% of the standard intravenous dose.

Determination of the appropriate dose of thermal vapor to be used to treat a particular condition can be performed via animal experiments and a dose-finding (Phase I/II) clinical trial. Preferred animal experiments involve measuring plasma drug concentrations after exposure of the test animal to the drug thermal vapor. These experiments may also be used to evaluate possible pulmonary toxicity of the thermal vapor. Because accurate extrapolation of these results to humans is facilitated if the test animal has a respiratory system similar to humans, mammals such as dogs or primates are a preferred group of test animals. Conducting such experiments in mammals also allows for monitoring of behavioral or physiological responses in mammals. Initial dose levels for testing in humans will generally be less than or equal to the least of the following: current standard intravenous dose, current standard oral dose, dose at which a physiological or behavioral response was obtained in the mammal experiments, and dose in the mammal model which resulted in plasma drug levels associated with a therapeutic effect of drug in humans. Dose escalation may then be performed in humans, until either an optimal therapeutic response is obtained or dose-limiting toxicity is encountered.

The actual effective amount of drug for a particular patient can vary according to the specific drug or combination thereof being utilized, the particular composition formulated, the mode of administration and the age, weight, and condition of the patient and severity of the episode being treated.

II. Drug-Supply Article

In one aspect, the invention provides a drug-supply article for production of drug-aerosol particles. The article is particularly suited for use in a device for inhalation therapy for delivery of a therapeutic agent to the lungs of a patient, for local or systemic treatment. The article is also suited for use in a device that generates an air stream, for application of drug-aerosol particles to a target site. For example, a stream of air carrying drug-aerosol particles can be applied to treat an acute or chronic skin condition, can be applied during surgery at the incision site, or can be applied to an open wound. In Section A below, the drug-supply article and use of the drug-supply article in an inhalation device are described. In Section B, the relationship between drug-film thickness, substrate area, and purity of drug-aerosol particles are discussed.

The term "purity" as used herein, with respect to the aerosol purity, means the fraction of drug composition in the aerosol/the fraction of drug composition in the aerosol plus drug degradation products. Thus purity is relative with regard to the purity of the starting material. For example, when the starting drug or drug composition used for substrate coating contained detectable impurities, the reported purity of the aerosol does not include those impurities present in the starting material that were also found in the aerosol, e.g., in certain cases if the starting material contained a 1% impurity and the aerosol was found to contain the identical 1% impurity, the aerosol purity may nevertheless be reported as >99% pure, reflecting the fact that the detectable 1% purity was not produced during the vaporization-condensation aerosol generation process.

A. Thin-Film Coated Substrate

A drug-supply article according to one embodiment of the invention is shown in cross-sectional view in FIG. 1A. Drug-supply article 10 is comprised of a heat-conductive substrate 12. Heat-conductive materials for use in forming the substrate are well known, and typically include metals, such as aluminum, iron, copper, stainless steel, and the like, alloys, ceramics, and filled polymers. The substrate can be of virtually any geometry, the square or rectangular configuration shown in FIG. 1A merely exemplary. Heat-conductive substrate 12 has an upper surface 14 and a lower surface 16.

Preferred substrates are those substrates that have surfaces with relatively few or substantially no surface irregularities so that a molecule of a compound vaporized from a film of the compound on the surface is unlikely to acquire sufficient energy through contact with either other hot vapor molecules, hot gases surrounding the area, or the substrate surface to result in cleavage of chemical bonds and hence compound decomposition. To avoid such decomposition, the vaporized compound should transition rapidly from the heated surface or surrounding heated gas to a cooler environment. While a vaporized compound from a surface may transition through Brownian motion or diffusion, the temporal duration of this transition may be impacted by the extent of the region of elevated temperature at the surface which is established by the velocity gradient of gases over the surface and the physical shape of surface. A high velocity gradient (a rapid increase in velocity gradient near the surface) results in minimization of the hot gas region above the heated surface and decreases the time of transition of the vaporized compound to a cooler environment. Likewise, a smoother surface facilitates this transition, as the hot gases and compound vapor are not precluded from rapid transition by being trapped in, for example, depressions, pockets or pores. Although a variety of substrates can be used, specifically preferred substrates are those that have impermeable surfaces or have an impermeable surface coating, such as, for example, metal foils, smooth metal surfaces, non-porous ceramics, etc. For the reasons stated above, non-preferred substrates for producing a therapeutic amount of a compound with less than 10% compound degradation via vaporization are those that have a substrate density of less than 0.5 g/cc, such as, for example, yarn, felts and foams, or those that have a surface area of less than 1 $mm^2$/particle such as, for example small alumina particles, and other inorganic particles.

With continuing reference to FIG. 1A, deposited on all or a portion of the upper surface 14 of the substrate is a film 18 of drug. Preferably the film has a thickness of between about 0.05 μm and 20 μm. Film deposition is achieved by a variety of methods, depending in part on the physical properties of the drug and on the desired drug film thickness. Exemplary methods include, but are not limited to, preparing a solution of drug in solvent, applying the solution to the exterior surface and removing the solvent to leave a film of drug. The drug solution can be applied by dipping the substrate into the solution, spraying, brushing or otherwise applying the solution to the substrate. Alternatively, a melt of the drug can be prepared and applied to the substrate. For drugs that are liquids at room temperature, thickening agents can be admixed with the drug to permit application of a solid drug film. Examples of drug film deposition on a variety of substrates are given below.

Figure 1B:
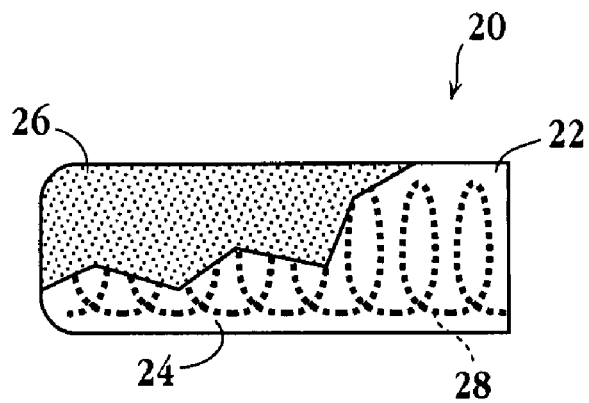

FIG. 1B is a perspective, cut-away view of an alternative geometry of the drug-supply article. Article 20 is comprised of a cylindrically-shaped substrate 22 formed from a heat-conductive material. Substrate 22 has an exterior surface 24 that is preferably impermeable by virtue of material selection, surface treatment, or the like. Deposited on the exterior surface of the substrate is a film 26 of the drug composition. As will be described in more detail below, in use the substrate of the drug-supply article is heated to vaporize all or a portion of the drug film. Control of air flow across the substrate surface during vaporization produces the desired size of drug-aerosol particles. In FIG. 1B, the drug film and substrate surface is partially cut-away in the figure to expose a heating element 28 disposed in the substrate. The substrate can be hollow with a heating element inserted into the hollow space or solid with a heating element incorporated into the substrate. The heating element in the embodiment shown takes the form of an electrical resistive wire that produces heat when a current flows through the wire. Other heating elements are suitable, including but not limited to a solid chemical fuel, chemical components that undergo an exothermic reaction, inductive heat, etc. Heating of the substrate by conductive heating is also suitable. One exemplary heating source is described in U.S. patent application for SELF-CONTAINED HEATING UNIT AND DRUG-SUPPLY UNIT EMPLOYING SAME, U.S. Ser. No. 60/472,697 filed May 21, 2003 which is incorporated herein by reference.

Figure 2A:
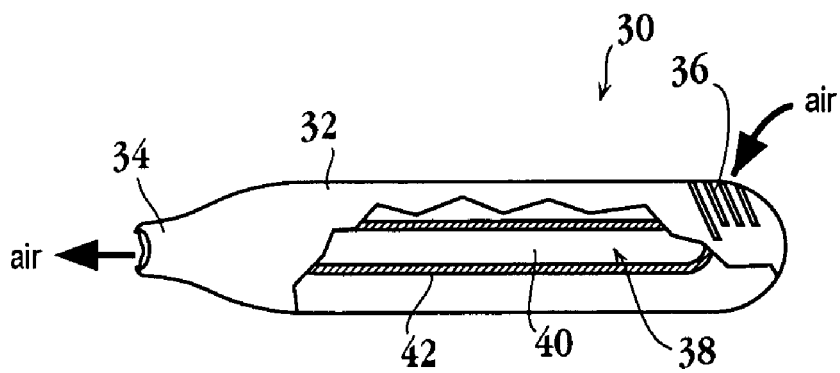
FIG. 2A is a perspective view of a drug-delivery device that incorporates a drug-supply article.

FIG. 2A is a perspective view of a drug-delivery device that incorporates a drug-supply article similar to that shown in FIG. 1B. Device 30 includes a housing 32 with a tapered end 34 for insertion into the mouth of a user. On the end opposite tapered end 34, the housing has one or more openings, such as slot 36, for air intake when a user places the device in the mouth and inhales a breath. Disposed within housing 32 is a drug-supply article 38, visible in the cut-away portion of the figure. Drug-supply article includes a substrate 40 coated on its external surface with a film 42 of a therapeutic drug to be delivered to the user. The drug-supply article can be rapidly heated to a temperature sufficient to vaporize all or a portion of the film of drug to form a drug vapor that becomes entrained in the stream of air during inhalation, thus forming the drug-aerosol particles. Heating of the drug-supply article is accomplished by, for example, an electrically-resistive wire embedded or inserted into the substrate and connected to a battery disposed in the housing. Substrate heating can be actuated by a user-activated button on the housing or via breath actuation, as is known in the art.

FIG. 2B shows another drug-delivery device that incorporates a drug-supply article, where the device components are shown in unassembled form. Inhalation device 50 is comprised of an upper external housing member 52 and a lower external housing member 54 that fit together. The downstream end of each housing member is gently tapered for insertion into a user's mouth, best seen on upper housing member 52 at downstream end 56. The upstream end of the upper and lower housing members are slotted, as seen best in the figure in the upper housing member at 58, to provide for air intake when a user inhales. The upper and lower housing members when fitted together define a chamber 60. Positioned within chamber 60 is a drug-supply unit 62, shown in a partial cut-away view. The drug supply unit has a tapered, substantially cylindrical substrate 64 coated with a film 66 of drug on its external, smooth, impermeable surface 68. Visible in the cut-away portion of the drug-supply unit is an interior region 70 of the substrate containing a substance suitable to generate heat. The substance can be a solid chemical fuel, chemical reagents that mix exothermically, electrically resistive wire, etc. A power supply source, if needed for heating, and any necessary valving for the inhalation device are contained in end piece 72.

In a typical embodiment, the device includes a gas-flow control valve disposed upstream of the drug-supply unit for limiting gas-flow rate through the condensation region for limiting the selected gas-flow rate, for example, for limiting air flow through the chamber as air is drawn by the user's mouth into and through the chamber. In a specific embodiment, the gas-flow valve includes an inlet port communicating with the chamber, and a deformable flap adapted to divert or restrict air flow away from the port increasingly, with increasing pressure drop across the valve. In another embodiment, the gas-flow valve includes the actuation switch, with valve movement in response to an air pressure differential across the valve acting to close the switch. In still another embodiment, the gas-flow valve includes an orifice designed to limit airflow rate into the chamber.

The device may also include a bypass valve communicating with the chamber downstream of the unit for offsetting the decrease in airflow produced by the gas-flow control valve, as the user draws air into the chamber. The bypass valve cooperates with the gas-control valve to control the flow through the condensation region of the chamber as well as the total amount of air being drawn through the device. Thus the total volumetric airflow through the device, is the sum of the volumetric airflow rate through the gas-control valve, and the volumetric airflow rate through the bypass valve. The gas control valve acts to limit air drawn into the device to a preselected level, e.g., 15 L/minute, corresponding to the selected air-flow rate for producing aerosol particles of a selected size. Once this selected airflow level is reached, additional air drawn into the device creates a pressure drop across the bypass valve which then accommodates airflow through the bypass valve into the downstream end of the device adjacent the user's mouth. Thus, the user senses a full breath being drawn in, with the two valves distributing the total airflow between desired airflow rate and bypass airflow rate.

These valves may be used to control the gas velocity through the condensation region of the chamber and hence to control the particle size of the aerosol particles produced by vapor condensation. More rapid airflow dilutes the vapor such that it condenses into smaller particles. In other words, the particle size distribution of the aerosol is determined by the concentration of the compound vapor during condensation. This vapor concentration is, in turn, determined by the extent to which airflow over the surface of the heating substrate dilutes the evolved vapor. Thus, to achieve smaller or larger particles, the gas velocity through the condensation region of the chamber may be altered by modifying the gas-flow control valve to increase or decrease the volumetric airflow rate. For example, to produce condensation particles in the size range 1-3.5 μm MMAD, the chamber may have substantially smooth-surfaced walls, and the selected gas-flow rate may be in the range of 4-50 L/minute.

Additionally, as will be appreciated by one of skill in the art, particle size may be also altered by modifying the cross-section of the chamber condensation region to increase or decrease linear gas velocity for a given volumetric flow rate, and/or the presence or absence of structures that produce turbulence within the chamber. Thus, for example to produce condensation particles in the size range 20-100 nm MMAD, the chamber may provide gas-flow barriers for creating air turbulence within the condensation chamber. These barriers are typically placed within a few thousands of an inch from the substrate surface.

The heat source in one general embodiment is effective to supply heat to the substrate at a rate that achieves a substrate temperature of at least 200° C., preferably at least 250° C., or more preferably at least 300° C. or 350° C., and produces substantially complete volatilization of the drug composition from the substrate within a period of 2 seconds, preferably, within 1 second, or more preferably within 0.5 seconds. Suitable heat sources include resistive heating devices which are supplied current at a rate sufficient to achieve rapid heating, e.g., to a substrate temperature of at least 200° C., 250° C., 300° C., or 350° C. preferably within 50-500 ms, more preferably in the range of 50-200 ms. Heat sources or devices that contain a chemically reactive material which undergoes an exothermic reaction upon actuation, e.g., by a spark or heat element, such as flashbulb type heaters of the type described in several examples, and the heating source described in the above-cited U.S. patent application for SELF-CONTAINED HEATING UNIT AND DRUG-SUPPLY UNIT EMPLOYING SAME, are also suitable. In particular, heat sources that generate heat by exothermic reaction, where the chemical "load" of the source is consumed in a period of between 50-500 msec or less are generally suitable, assuming good thermal coupling between the heat source and substrate.

FIGS. 3A-3E are high speed photographs showing the generation of aerosol particles from a drug-supply unit. FIG. 3A shows a heat-conductive substrate about 2 cm in length coated with a film of drug. The drug-coated substrate was placed in a chamber through which a stream of air was flowing in an upstream-to-downstream direction (indicated by the arrow in FIG. 3A) at rate of about 15 L/min. The substrate was electrically heated and the progression of drug vaporization monitored by real-time photography. FIGS. 3B-3E show the sequence of drug vaporization and aerosol generation at time intervals of 50 milliseconds (msec), 100 msec, 200 msec, and 500 msec, respectively. The white cloud of drug-aerosol particles formed from the drug vapor entrained in the flowing air is visible in the photographs. Complete vaporization of the drug film was achieved by 500 msec.

The drug-supply unit generates a drug vapor that can readily be mixed with gas to produce an aerosol for inhalation or for delivery, typically by a spray nozzle, to a topical site for a variety of treatment regimens, including acute or chronic treatment of a skin condition, administration of a drug to an incision site during surgery or to an open wound. Rapid vaporization of the drug film occurs with minimal thermal decomposition of the drug, as will be further demonstrated in Section B.

B. Selection of Drug Film Thickness and Substrate Area

As discussed above, the drug supply article includes a film of drug formed on a substrate. In a preferred embodiment, the drug composition consists of two or more drugs. In a more preferred embodiment, the drug composition comprises pure drug. The drug film in one general embodiment of the invention has a thickness of between about 0.05-20 µm, and preferably between 0.1-15 µm, more preferably between 0.2-10 µm and still more preferably 0.5-10 µm, and most preferably 1-10 µm. The film thickness for a given drug composition is such that drug-aerosol particles, formed by vaporizing the drug composition by heating the substrate and entraining the vapor in a gas stream, have (i) 10% by weight or less drug-degradation product, more preferably 5% by weight or less, most preferably 2.5% by weight or less and (ii) at least 50% of the total amount of drug composition contained in the film. The area of the substrate on which the drug composition film is formed is selected to achieve an effective human therapeutic dose of the drug aerosol. Each of these features of the drug article is described below.

1. Aerosol Particle Purity and Yield

In studies conducted in support of the invention, a variety of drugs were deposited on a heat-conductive, impermeable substrate and the substrate was heated to a temperature sufficient to generate a thermal vapor. Purity of drug-aerosol particles in the thermal vapor was determined by a suitable analytical method. Three different substrate materials were used in the studies: stainless steel foil, aluminum foil, and a stainless steel cylinder. Methods B-G below detail the procedures for forming a drug film on each substrate and the method of heating each substrate.

Figure 4A:
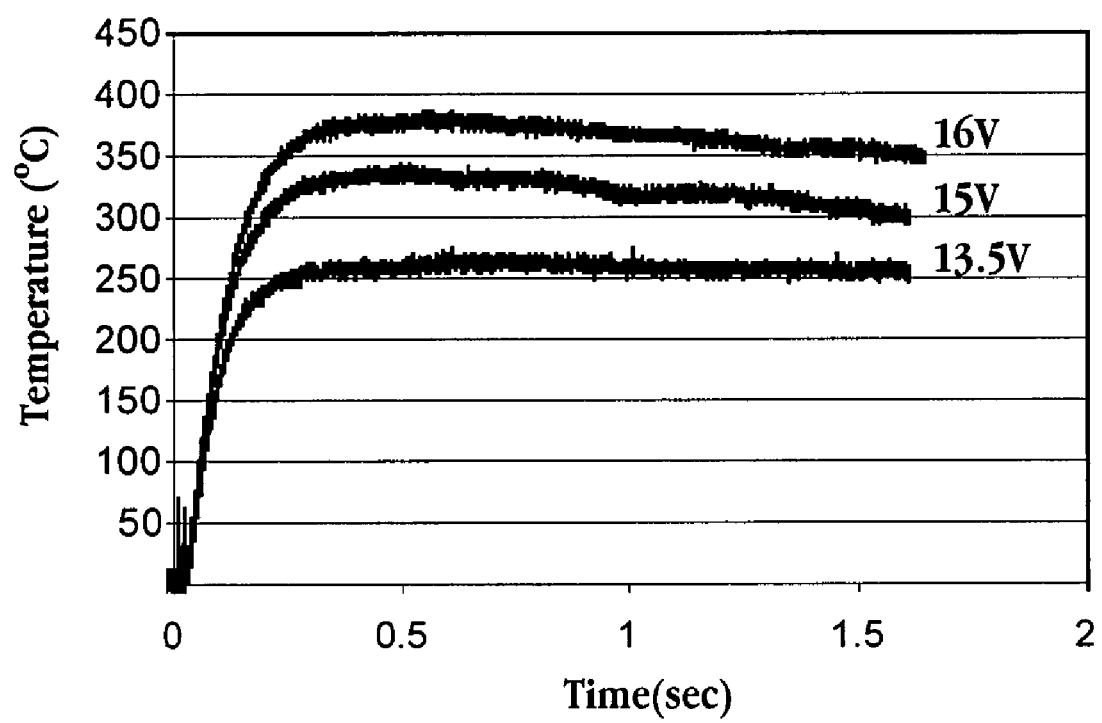
FIGS. 4A-4B are plots of substrate temperature increase, measured in still air with a thin thermocouple (Omega, Model CO2-K), as a function of time. The substrate in FIG. 4A was heated resistively by connection to a capacitor charged to 13.5 Volts (lower line), 15 Volts (middle line), and 16 Volts (upper line); the substrate in FIG. 4B was heated resistively by discharge of a capacitor at 16 Volts.

The stainless steel foil substrate employed for drugs tested according to Method B was resistively heated by placing the substrate between a pair of electrodes connected to a capacitor. The capacitor was charged to between 14-17 Volts to resistively heat the substrate. FIG. 4A is a plot of substrate temperature increase, measured in still air with a thin thermocouple (Omega, Model CO2-K), as a function of time, in seconds, for a stainless steel foil substrate resistively heated by charging the capacitor to 13.5 V (lower line), 15 V (middle line), and 16 V (upper line). When charged with 13.5 V, the substrate temperature increase was about 250° C. within about 200-300 milliseconds. As the capacitor voltage increased, the peak temperature of the substrate also increased. Charging the capacitor to 16V heated the foil substrate temperature about 375° C. in 200-300 milliseconds (to a maximum temperature of about 400° C.).

Figure 4B:
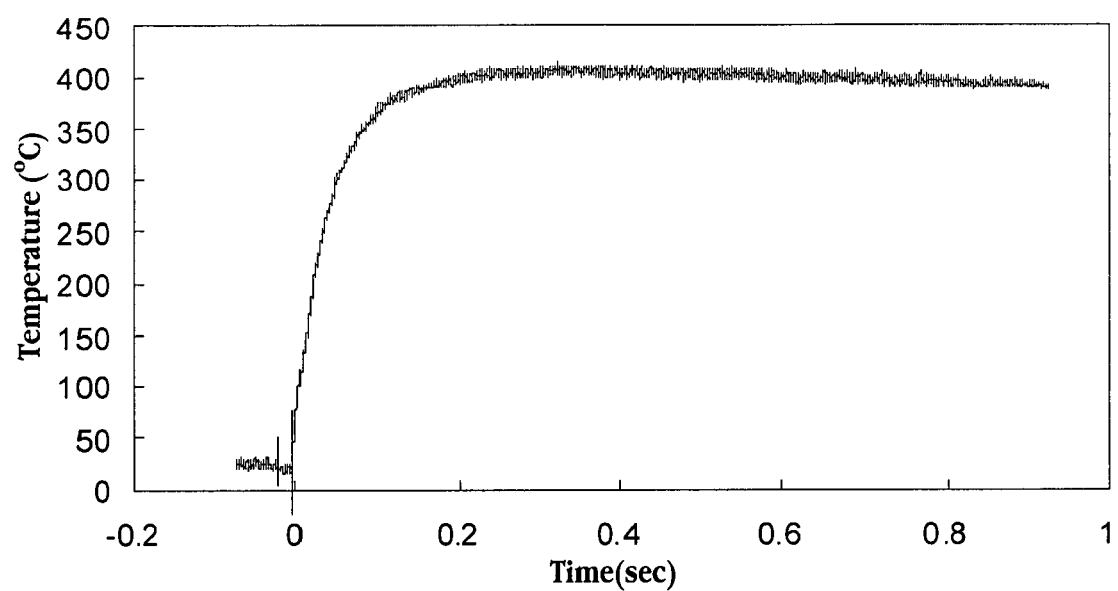

FIG. 4B shows the time-temperature relationship for a stainless steel foil substrate having a thickness of 0.005 inches. The foil substrate was heated by charging a capacitor, connected to the substrate through electrodes, to 16 V. The substrate reached its peak temperature of 400° C. in about 200 milliseconds, and maintained that temperature for the 1 second testing period.

Figure 5A:
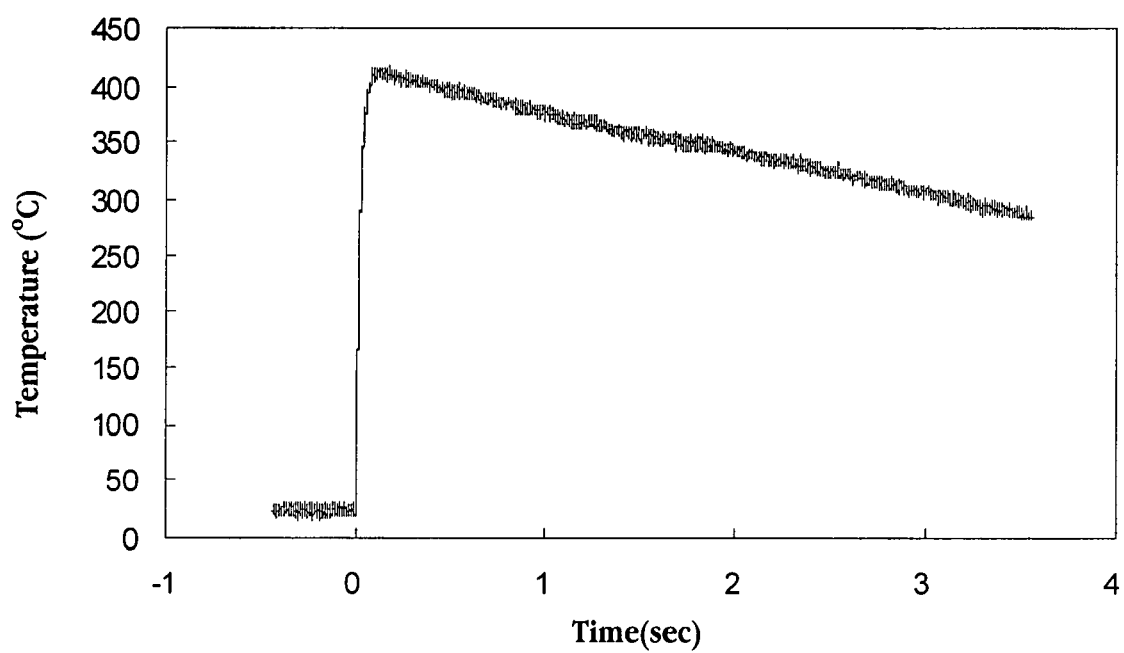
FIGS. 5A-5B are plots of substrate temperature, in ° C., as a function of time, in seconds, for a hollow stainless steel cylindrical substrate heated resistively by connection to a capacitor charged to 21 Volts, where
Figure 5B:
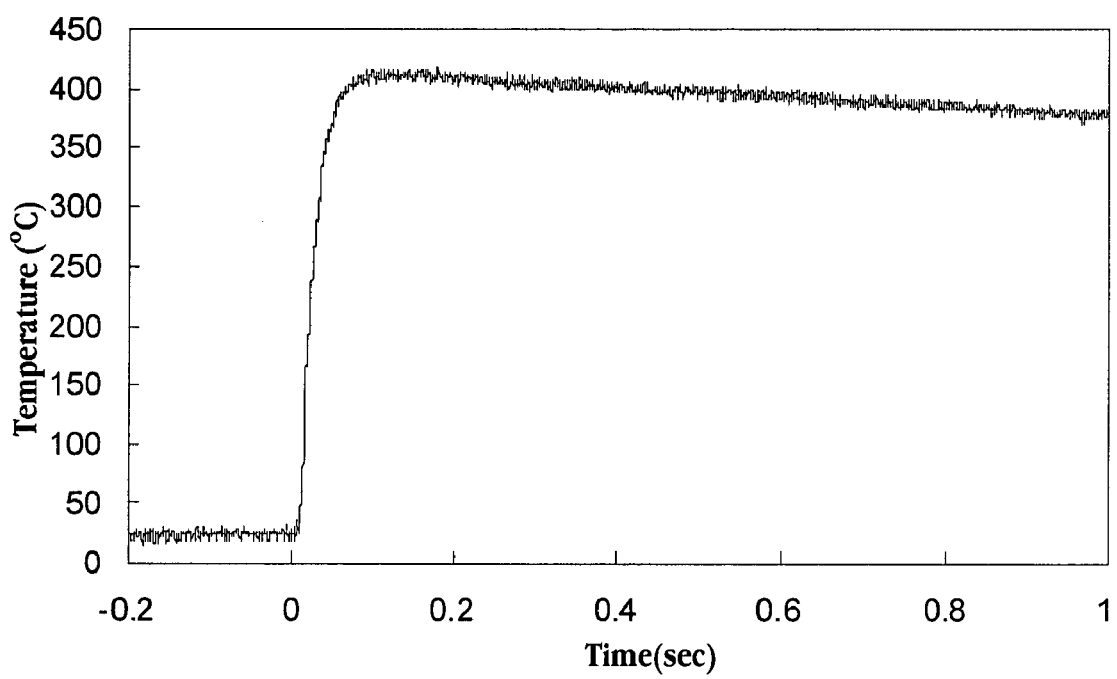

In Methods D and E, a hollow, stainless steel tube was used as the drug-film substrate. The cylindrical tube in Method D had a diameter of 13 mm and a length of 34 mm. The cylindrical tube in Method E had a diameter of 7.6 mm and a length of 51 mm. In Method D, the substrate was connected to two 1 Farad capacitors wired in parallel, whereas in Method E, the substrate was connected to two capacitors (a 1 Farad and a 0.5 Farad) wired in parallel. FIGS. 5A-5B show substrate temperature as a function of time, for the cylindrical substrate of Method D. FIG. 5B shows a detail of the first 1 second of heating.

Aluminum foil was used as a substrate for testing other compounds, as described in Methods C, F, and G. The drug-coated substrate was heated either by wrapping it around a halogen tube and applying 60 V or 90 V alternating current through the bulb or by placing the substrate in a furnace.

For each substrate type, a drug film was formed by applying a solution containing the drug onto the substrate. As described in Method A, a solution of the drug in a solvent was prepared. A variety of solvents can be used and selection is based, in part, on the solubility properties of the drug and the desired solution concentration. Common solvent choices included methanol, chloroform, acetone, dichloromethane, other volatile organic solvents, dimethylformamide, water, and solvent mixtures. The drug solution was applied to the substrate by dip coating, yet other methods such as spray coating are contemplated as well. Alternatively, a melt of the drug can be applied to the substrate.

In Examples 1-236 below, a substrate containing a drug film of a certain thickness was prepared. To determine the thickness of the drug film, one method that can be used is to determine the area of the substrate and calculate drug film thickness using the following relationship:

film thickness (cm)=drug mass (g)/[drug density (g/cm$^3$)×substrate area (cm$^2$)]

The drug mass can be determined by weighing the substrate before and after formation of the drug film or by extracting the drug and measuring the amount analytically. Drug density can be experimentally determined by a variety of techniques, known by those of skill in the art or found in the literature or in reference texts, such as in the CRC. An assumption of unit density is acceptable if an actual drug density is not known.

Figures 6, 7:
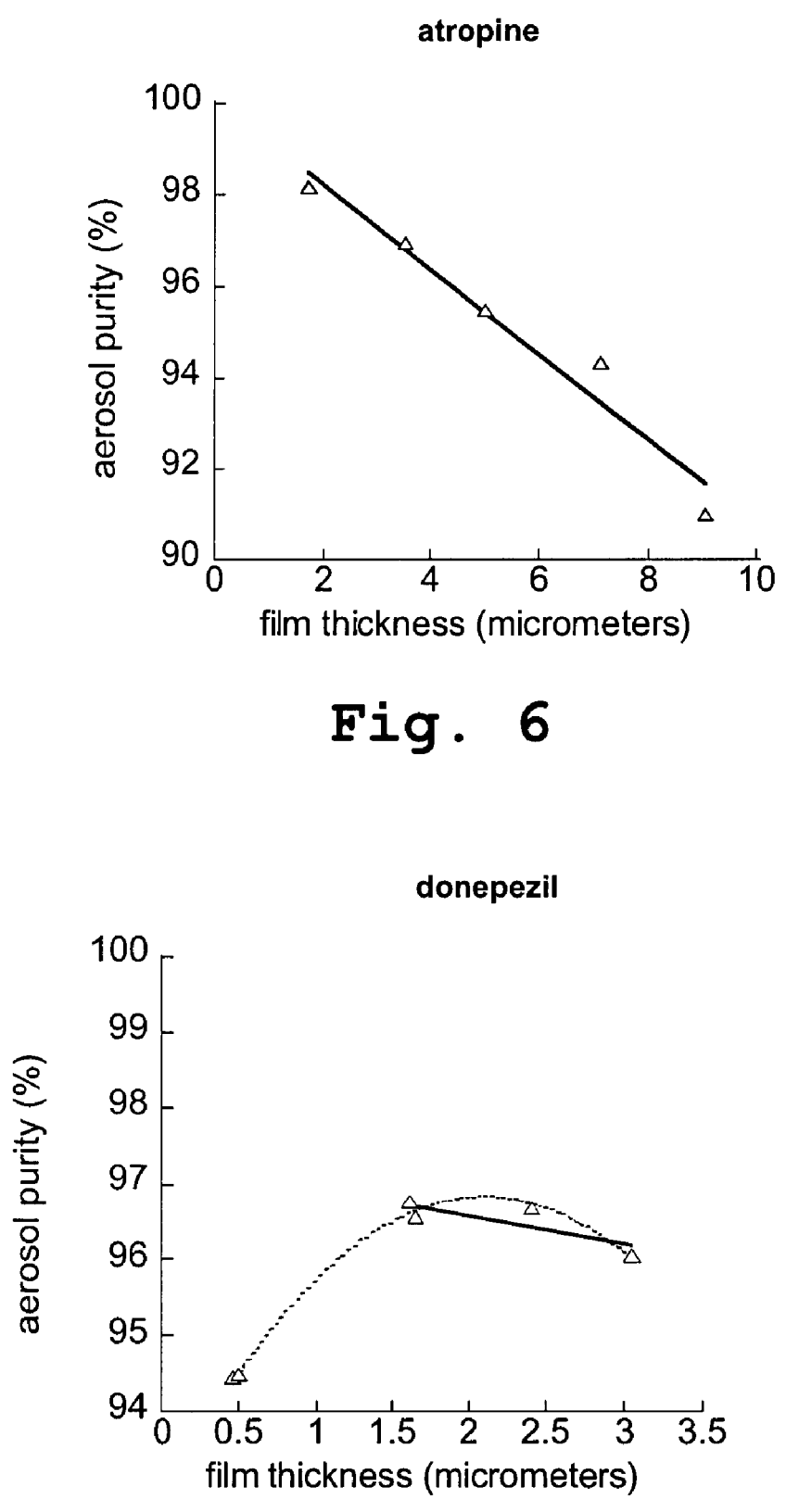

In the studies reported in the Examples, the substrate having a drug film of known thickness was heated to a temperature sufficient to generate a thermal vapor. All or a portion of the thermal vapor was recovered and analyzed for presence of drug-degradation products, to determine purity of the aerosol particles in the thermal vapor. Several drugs are discussed here as merely exemplary of the studies reported in Examples 1-236. Example 10 describes preparation of a drug-supply article containing atropine, a muscarinic antagonist. Substrates containing films of atropine ranging in thickness from between about 1.7 µm to about 9.0 µm were prepared. The stainless steel substrates were heated and the purity of the drug-aerosol particles in the thermal vapor generated from each substrate was determined. FIG. 6 shows the results, where drug aerosol purity as a function of drug film thickness is plotted. There is a clear relationship between film thickness and aerosol particle purity, where as the film thickness decreases, the purity increases. An atropine film having a thickness of 9.0 µm produced a thermal vapor having a purity of 91%; an atropine film having a thickness of 1.7 µm produced a thermal vapor having a purity of 98%.

Hydromorphone, an analgesic, was also tested, as describe in Example 66. Substrates having a drug film thickness of between about 0.7 µm to about 2.7 µm were prepared and heated to generate a thermal vapor. Purity of the aerosol particles improved as the thickness of the drug film on the substrate decreased.

Figure 23:
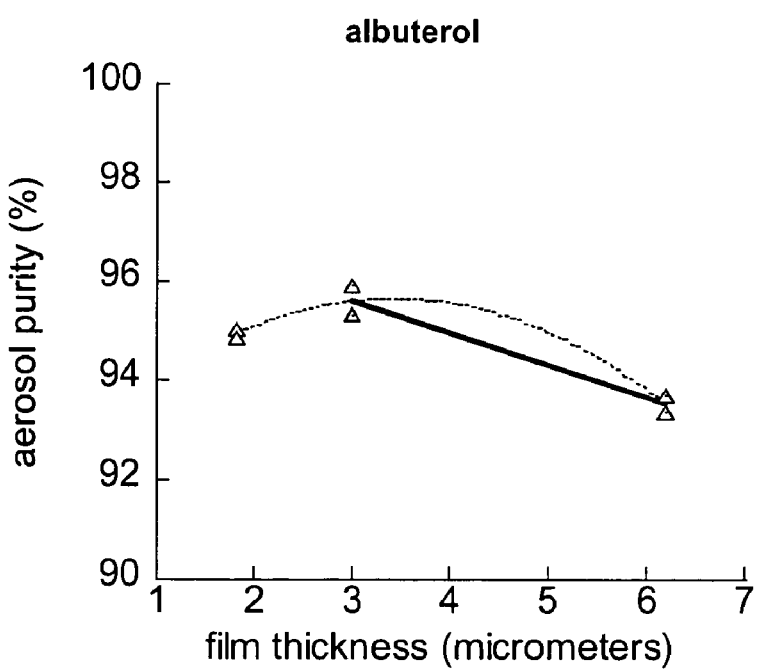
FIG. 23 is plot showing purity of thermal vapor as a function of drug film thickness, in micrometers, for albuterol free base.
Figure 25A:
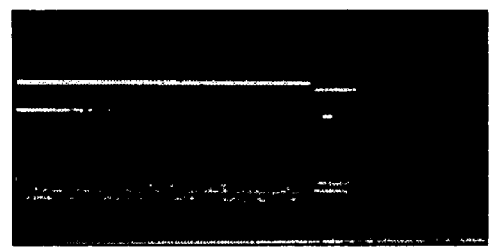
FIGS. 25A-25D are high speed photographs showing the generation of a thermal vapor of disopyramide from a film of drug coated on a substrate drug-supply unit, where the photographs are taken at prior to substrate heating (t=0 ms, FIG. 25A) and during substrate heating at times of 50 milliseconds (FIG. 25B), 100 milliseconds (FIG. 25C), and 200 milliseconds (FIG. 25D)
Figure 25B:
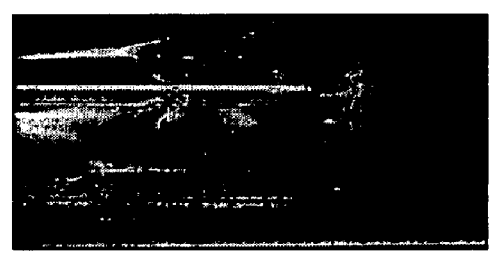
Figure 25C:
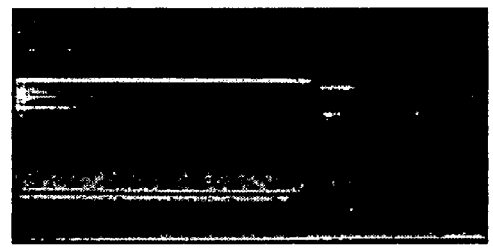
Figure 25D:
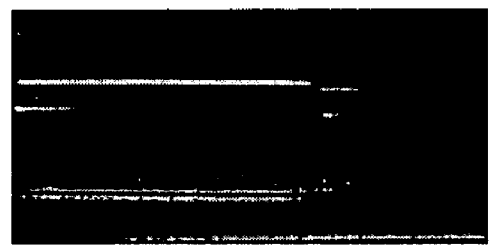
Figure 26A:
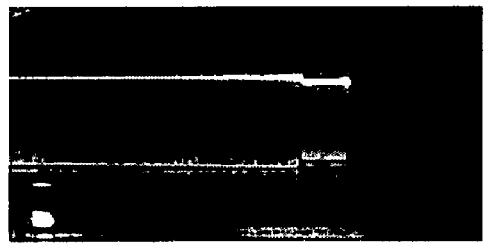
FIGS. 26A-26E are high speed photographs showing the generation of a thermal vapor of buprenorphine from a film of drug coated on a substrate drug-supply unit, where the photographs are taken at prior to substrate heating (t=0 ms, FIG. 26A) and during substrate heating at times of 50 milliseconds (FIG. 26B), 100 milliseconds (FIG. 26C), 200 milliseconds (FIG. 26D), and 300 milliseconds (FIG. 26E).
Figure 26B:
Figure 26C:
Figure 26D:
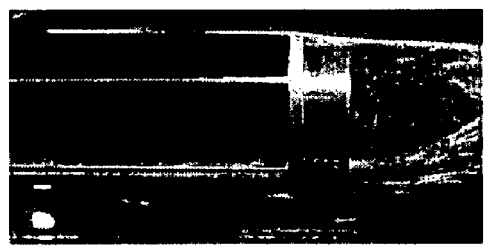
Figure 26E:
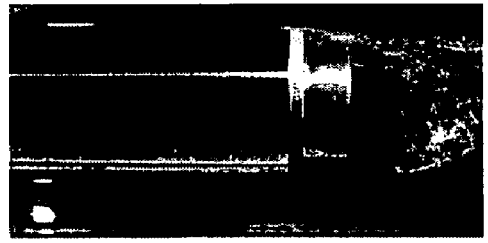

FIG. 7 shows the relationship between drug film thickness and aerosol-purity for donepezil. As described in Example 44, donepezil was coated onto foil substrates to film thicknesses ranging from about 0.5 µm to about 3.2 µm. Purity of the aerosol particles from each of the films on the substrates was analyzed. At drug film thicknesses of 1.5 µm to 3.2 µm, purity of the aerosol particles improved as thickness of the drug film on the substrate decreased, similar to the trend found for atropine and hydromorphone. In contrast, at less than 1.5 µm thickness, purity of the aerosol particles worsened as thickness of the drug film on the substrate decreased. A similar pattern was also observed for albuterol, as described in Example 3, with aerosol particles purity peaking for films of approximately 3 μm, and decreasing for both thinner and thicker films as shown in FIG. 23.

FIGS. 9-23 present data for aerosol purity as a function of film thickness for the following compounds: buprenorphine (Example 16), clomipramine (Example 28), ciclesonide (Example 26), midazolam (Example 100), nalbuphine (Example 103), naratriptan (Example 106), olanzapine (Example 109), quetiapine (Example 127), tadalafil (Example 140), prochlorperazine (Example 122), zolpidem (Example 163), fentanyl (Example 57), alprazolam (Example 4), sildenafil (Example 134), and albuterol (Example 3).

In FIGS. 6-23, the general relationship between increasing aerosol purity with decreasing film thickness is apparent; however the extent to which aerosol purity varies with a change in film thickness varies for each drug composition. For example, aerosol purity of sildenafil (FIG. 22) exhibited a strong dependence on film thickness, where films about 0.5 μm in thickness had a purity of greater than 99% and films of about 1.6 μm in thickness had a purity of between 94-95%. In contrast, for midazolam (FIG. 12), increasing the film thickness from approximately 1.2 μm to approximately 5.8 μm resulted in a decrease in aerosol particle purity from greater than 99.9% to approximately 99.5%, a smaller change in particle purity despite a larger increase in film thickness compared with the sildenafil example. Moreover, as was discussed above, the inverse relationship between film thickness and purity of aerosolized drug observed for many compounds in the thickness range less than about 20 μm does not necessarily apply at the thinnest film thicknesses that were tested. Some compounds, such as illustrated by donepezil (FIG. 7) show a rather pronounced decrease in purity at film thicknesses both below and above an optimal film thickness, in this case, above and below about 2 μm film thicknesses.

One way to express the dependence of aerosol purity on film thickness is by the slope of the line from a plot of aerosol purity against film thickness. For compounds such as donepezil (FIG. 7), the slope of the line is taken from the maximum point in the curve towards the higher film thickness. Table 1, discussed below, shows the slope of the line for the curves shown in FIGS. 6-23. Particularly preferred compounds for delivery by the various embodiments of the present invention are compounds with a substantial (i.e., highly negative) slope of the line on the aerosol purity versus thickness plot, e.g., a slope more negative than −0.1% purity per micron and more preferably −0.5% purity per micron.

In addition to selection of a drug film thickness that provides aerosol particles containing 10% or less drug-degradation product (i.e., an aerosol particle purity of 90% or more), the film thickness is selected such that at least about 50% of the total amount of drug composition contained in the film is vaporized when the substrate is heated to a temperature sufficient to vaporize the film. In the studies described herein, the percentage of drug film vaporized was determined by quantifying (primarily by HPLC or weight) the mass of drug composition collected upon vaporization or alternatively by the amount of substrate mass decrease. The mass of drug composition collected after vaporization and condensation was compared with the starting mass of the drug composition film that was determined prior to vaporization to determine a percent yield, also referred to herein as a percent emitted. This value is indicated in many of the Examples set forth below. For example, in Example 1 a film having a thickness of 1.1 μm was formed from the drug acebutolol, a beta adrenergic blocking agent. The mass coated on the substrate was 0.89 mg and the mass of drug collected in the thermal vapor was 0.53 mg, to give a 59.6 percent yield. After vaporization, the substrate and the testing chamber were washed to recover any remaining drug. The total drug recovered from the test apparatus, including the emitted thermal vapor, was 0.8 mg, to give a 91% total recovery. In another example, midazolam was coated onto a impermeable substrate, as described in Example 100. A drug film having a thickness of 9 μm was formed. Heating of the substrate generated a thermal vapor containing drug aerosol particles having a purity of 99.5%. The fraction of drug film collected on the filter, i.e., the percent yield, was 57.9%. After vaporization, the substrate and the testing chamber were washed to recover any remaining drug. The total drug recovered from the test apparatus and the filter was 5.06 mg, to give a 94.2% total recovery.

2. Substrate Area

Another feature of the drug-supply article is that the selected substrate surface area is sufficient to yield a therapeutic dose of the drug aerosol when used by a subject. The amount of drug to provide a therapeutic dose is generally known in the art or can be determined as discussed above. The required dosage and selected film thickness, discussed above, dictate the minimum required substrate area in accord with the following relationship:

$$\text{film thickness (cm)} \times \text{drug density (g/cm}^3\text{)} \times \text{substrate area (cm}^2\text{)} = \text{dose (g)}$$

As noted above, drug density can be determined experimentally or from the literature, or if unknown, can be assumed to be 1 g/cc. To prepare a drug supply article comprised of a drug film on a heat-conductive substrate that is capable of administering an effective human therapeutic dose, the minimum substrate surface area is determined using the relationships described above to determine a substrate area for a selected film thickness that will yield a therapeutic dose of drug aerosol. Table 1 shows a calculated substrate surface area for a variety of drugs on which an aerosol purity—film thickness profile was constructed.

TABLE 1

| Drug | Typical Dose (mg) | Preferred Film Thickness (μm) | Calculated Substrate Surface Area (cm$^2$) | Slope of Line on aerosol purity vs. thickness plot (% purity/micron) |
| --- | --- | --- | --- | --- |
| Albuterol | 0.2 | 0.1-10 | 0.2-20 | −0.64 (FIG. 23) |
| Alprazolam | 0.25 | 0.1-10 | 0.25-25 | −0.44 (FIG. 21) |
| Amoxapine | 25 | 2-20 | 12.5-125 | |
| Atropine | 0.4 | 0.1-10 | 0.4-40 | −0.93 (FIG. 6) |
| Bumetanide | 0.5 | 0.1-5 | 1-50 | |
| Buprenorphine | 0.3 | 0.05-10 | 0.3-60 | −0.63 (FIG. 9) |
| Butorphanol | 1 | 0.1-10 | 1-100 | |
| Clomipramine | 50 | 1-8 | 62-500 | −1.0 (FIG. 10) |

TABLE 1-continued

| Drug | Typical Dose (mg) | Preferred Film Thickness (μm) | Calculated Substrate Surface Area ($cm^2$) | Slope of Line on aerosol purity vs. thickness plot (% purity/micron) |
|---|---|---|---|---|
| Donepezil | 5 | 1-10 | 5-50 | −0.38 (FIG. 7) |
| Hydromorphone | 2 | 0.05-10 | 2-400 | −0.55 (FIG. 8) |
| Loxapine | 10 | 1-20 | 5-100 | |
| Midazolam | 1 | 0.05-20 | 0.5-200 | −0.083 (FIG. 12) |
| Morphine | 5 | 0.2-10 | 5-250 | |
| Nalbuphine | 5 | 0.2-5 | 10-250 | −1.12 (FIG. 13) |
| Naratriptan | 1 | 0.2-5 | 2-50 | −1.42 (FIG. 14) |
| Olanzapine | 10 | 1-20 | 5-100 | −0.16 (FIG. 15) |
| Paroxetine | 20 | 1-20 | 10-200 | |
| Prochlorperazine | 5 | 0.1-20 | 2.5-500 | −0.11 (FIG. 18) |
| Quetiapine | 50 | 1-20 | 25-500 | −0.18 (FIG. 16) |
| Rizatriptan | 3 | 0.2-20 | 1.5-150 | |
| Sertraline | 25 | 1-20 | 12.5-250 | |
| Sibutramine | 10 | 0.5-2 | 50-200 | |
| Sildenafil | 6 | 0.2-3 | 20-300 | −3.76 (FIG. 22) |
| Sumatriptan | 3 | 0.2-6 | 5-150 | |
| Tadalafil | 3 | 0.2-5 | 6-150 | −1.52 (FIG. 17) |
| Testosterone | 3 | 0.2-20 | 1.5-150 | |
| Vardenafil | 3 | 0.1-2 | 15-300 | |
| Venlafaxine | 50 | 2-20 | 25-250 | |
| Zolpidem | 5 | 0.1-10 | 5-500 | −0.88 (FIG. 19) |
| Apomorphine HCl | 2 | 0.1-5 | 4-200 | |
| Celecoxib | 50 | 2-20 | 25-250 | |
| Ciclesonide | 0.2 | 0.05-5 | 0.4-40 | −1.70 (FIG. 11) |
| Fentanyl | 0.05 | 0.05-5 | 0.1-10 | |
| Eletriptan | 3 | 0.2-20 | 1.5-150 | |
| Parecoxib | 10 | 0.5-2 | 50-200 | |
| Valdecoxib | 10 | 0.5-10 | 10-200 | |

The actual dose of drug delivered, i.e., the percent yield or percent emitted, from the drug-supply article will depend on, along with other factors, the percent of drug film that is vaporized upon heating the substrate. Thus, for drug films that yield upon heating 100% of the drug film and aerosol particles that have a 100% drug purity, the relationship between dose, thickness, and area given above correlates directly to the dose provided to the user. As the percent yield and/or particle purity decrease, adjustments in the substrate area can be made as needed to provide the desired dose. Also, as one of skill in the art will recognize, larger substrate areas other than the minimum calculated area for a particular film thickness can be used to deliver a therapeutically effective dose of the drug. Moreover as can be appreciated by one of skill in art, the film need not coat the complete surface area if a selected surface area exceeds the minimum required for delivering a therapeutic dose from a selected film thickness.

3. Characteristics of the Drug-Supply Article

The drug-supply article of the invention is heated to generate a thermal vapor containing drug aerosol particles for therapeutic administration to a patient. In studies performed in support of the invention, high speed photography was used to monitor visually production of the thermal vapor. FIGS. 24A-24D are high speed photographs showing the generation of a thermal vapor of phenytoin from a film coated on a substrate, prepared as described in Example 116. FIG. 24A is a photograph showing the drug-coated substrate prior to heating (t=0 milliseconds (ms)). The photographs in FIGS. 24B-24D show formation of a thermal vapor as a function of time after initiation of substrate heating. The photograph in FIG. 24B, taken 50 milliseconds after initiation of substrate heating, shows formation of a thermal vapor over the substrate surface. The subsequent photographs show that the majority of the thermal vapor is formed prior to 100 milliseconds after initiation of substrate heating (FIG. 24C), with formation substantially completed by about 200 milliseconds after initiation of substrate heating (FIG. 24D).

FIGS. 25A-25D are high speed photographs showing the generation of a thermal vapor of disopyramide from a film of drug coated on a substrate, prepared as described in Example 42. FIG. 25A shows the drug-coated substrate prior to heating (t=0 milliseconds (ms)). The photographs in FIGS. 25B-25D show formation of a thermal vapor as a function of time after initiation of substrate heating. As seen, 50 milliseconds after initiation of substrate heating (FIG. 25B), a thermal vapor is present over the substrate surface. The subsequent photographs show that the majority of the thermal vapor is formed prior to 100 milliseconds after initiation of substrate heating (FIG. 25C), with formation substantially completed by about 200 milliseconds after initiation of substrate heating (FIG. 25D).

Similar photographs are shown for buprenorphine in FIGS. 26A-26E. Upon heating of a buprenorphine substrate, prepared as described in Example 16, presence of a thermal vapor is evident in the photograph taken 50 milliseconds after heating was initiated (FIG. 26B). At 100 milliseconds (FIG. 26C) and 200 milliseconds (FIG. 26D) after initiation of substrate heating the thermal vapor was still observed in the photographs. Generation of the thermal vapor was complete by 300 milliseconds (FIG. 26E).

4. Modifications to Optimize Aerosol Purity and/or Yield

As discussed above, purity of aerosol particles for many drugs correlates directly with film thickness, where thinner films typically produce aerosol particles with greater purity. Thus, one method to optimize purity disclosed in this invention is the use of thinner films. Likewise, the aerosol yield may also be optimized in this manner: The invention, however, further contemplates strategies in addition to, or in combination with, adjusting film thickness to increase either aerosol purity or yield or both. These strategies include modifying the structure or form of the drug, and/or producing the thermal vapor in an inert atmosphere.

Thus, in one embodiment, the invention contemplates generation of and/or use of an altered form of the drug, such as, for example but not limitation, use of a pro-drug, or a free base, free acid or salt form of the drug. As demonstrated in various Examples below, modifying the form of the drug can impact the purity and or yield of the aerosol obtained. Although not always the case, the free base or free acid form of the drug as opposed to the salt, generally results in either a higher purity or yield of the resultant aerosol. Thus, in a preferred embodiment of the invention, the free base and free acid forms of the drugs are used.

Another approach contemplates generation of drug-aerosol particles having a desired level of drug composition purity by forming the thermal vapor under a controlled atmosphere of an inert gas, such as argon, nitrogen, helium, and the like. Various Examples below show that a change in purity can be observed upon changing the gas under which vaporization occurs.

More generally, and in another aspect, the invention contemplates a method of forming an article for use in an aerosol device, for producing aerosol particles of a drug composition that have the desired purity and a film that provides a desired percent yield. In the method, a drug film with a known film thickness is prepared on a heat-conductive, impermeable substrate. The substrate is heated to vaporize the film, thereby producing aerosol particles containing the drug compound. The drug composition purity of the aerosol particles in the thermal vapor is determined, as well as the percent yield, i.e., the fraction of drug composition film vaporized and delivered by the method. If the drug composition purity of the particles is less than about 90%, but greater than about 60%, more preferably greater than about 70%, or if the percent yield is less than about 50%, the thickness of the drug film is adjusted to a thickness different from the initial film thickness for testing. That is, a substrate having an adjusted film thickness is heated and the percent purity and percent yield are determined. The film thickness is continually adjusted until the desired drug composition aerosol purity and yield are achieved. For example, the initial film thickness can be between about 1-20 µm. A second, different film thickness would be between about 0.05-10 µm. This method is particularly suited for drug compositions that exhibit a percent yield of greater than about 30% and a drug composition aerosol purity of between about 60%-90%, more preferably between about 70%-90%.

Examples 166-233 correspond to studies conducted on drugs that when deposited as a thin film on a substrate produced a thermal vapor having a drug purity of less than about 90% but greater than about 60% or where the percent yield was less than about 50%. Purity of the thermal vapor of many of these drugs would be improved by using one or more of the approaches discussed above. More specifically, for some drugs a simple adjustment in film thickness, typically to a thinner film, improves purity of the aerosol particles. For other drugs, heating the substrate in an inert atmosphere, such as an argon or nitrogen atmosphere, alone or in combination with an adjustment in film thickness, achieves aerosol particles with the requisite purity of 90% or more and volatilization of a fraction of the drug film that is greater than about 50%.

Based on the studies conducted, the following drugs are particularly suited to the method and approaches to optimizing purity or yield: adenosine, amoxapine, apomorphine, aripiprazole, aspirin, astemizole, atenolol, benazepril, benztropine, bromazepam, budesonide, buspirone, caffeine, captopril, carbamazepine, cinnarizine, clemastine, clemastine fumarate, clofazimine, desipramine, dipyridamole, dolasetron, doxylamine, droperidol, enlapril maleate, fluphenazine, flurazepam, flurbiprofen, fluvoxamine, frovatriptan, hydrozyzine, ibutilide, indomethacine norcholine ester, ketorolac, ketorolac norcholine ester, levodopa, melatonin, methotrexate, methysergide, metoclopramide, nabumetone, naltrexone, nalmefene, perphenazine, pimozide, piroxicam, pregnanolone, prochlorperazine 2HCl, protriptyline HCl, protriptyline, pyrilamine, pyrilamine maleate, quinine, ramipril, risperidone, scopolamine, sotalol, sulindac, terfenadine, triamcinolone acetonide, trihexyphenidyl, thiothixene, telmisartan, temazepam, triamterene, trimipramine, ziprasidone, and zonisamide.

Examples 234-235 correspond to studies conducted on combinations of drugs that when deposited as a thin film of produced a thermal vapor (aerosol) having a drug purity of greater than 90% and a recovered yield of each drug in the aerosol of greater than 50%.

Example 236 corresponds to studies conducted on drugs that when deposited as a thin film on a substrate produce a thermal vapor having a drug purity of less than about 60%.

It will be appreciated that to provide a therapeutic dose the substrate surface area is adjusted according to the film thickness that yields the desired particle purity and percent yield, as discussed above.

III. Utility: Thin-Film Article, Device, and Methods

As can be appreciated from the above examples showing generation of a pure drug thermal vapor, from thin films (i.e. 0.02-20 µm) of the drug, the invention finds use in the medical field in compositions and articles for delivery of a therapeutic of a drug. Thus, the invention includes, in one aspect, a drug-supply article for production of a thermal vapor that contains drug-aerosol particles. The drug-supply article includes a substrate coated with a film of a drug composition to be delivered to a subject, preferably a human subject. The thickness of the drug composition film is selected such that upon vaporizing the film by heating the substrate to a temperature sufficient to vaporize at least 50% of the drug composition film, typically to a temperature of at least about 200° C., preferably at least about 250° C., more preferably at least about 300° C. or 350° C., a thermal vapor is generated that has 10% or less drug-degradation product. The area of the substrate is selected to provide a therapeutic dose, and is readily determined based on the equations discussed above.

In another aspect the invention relates to a method of forming a drug-supply article comprised of a substrate and a film of a drug composition. The method includes identifying a thickness of drug composition film that yields after vaporization of the film the drug composition in a substantially non-pyrolyzed form, as evidenced, for example, by the purity of the vapor. This may be done by an iterative process where one first prepares on a heat-conductive substrate, a drug composition having a given film thickness, e.g., 1-10 microns. The substrate is then heated, e.g., to a selected temperature between 200° C.-600° C., preferably 250° C. to 550° C., more preferably, 300° C.-500° C., or 350° C. to 500° C., to produce an aerosol of particles containing the compound. As seen in the examples below, the aerosol may be collected in particle form or simply collected on the walls of a surrounding container. The purity of the drug composition is then determined, e.g., expressed as a weight percent or analytical percent degradation product. If the percent degradation product is above a selected threshold, e.g., 1, 2.5, 5, or 10 percent, the steps above are repeated with different compound thicknesses, typically with successively lower thicknesses, until the aerosolized compound is within the desired limit of degradation, e.g., 1, 2.5, 5, or 10%. Similarly, if the initial volatilization study shows very low levels of degradation, e.g., less than 0.1, 1, 2, or 5%, it may be desirable in subsequent tests to increase film thickness, to obtain a greatest film thickness at which an acceptable level of drug degradation is observed.

After identification of the film thickness that generates a highly pure thermal drug composition vapor (e.g., drug composition purity greater than about 90%), the area of substrate required to accommodate a therapeutic dose, when inhaled by a human, is determined. For example, the required oral dose for atropine is 0.4 mg (Example 10). Using the data shown in FIG. 6, a thermal vapor comprised of substantially non-pyrolyzed drug, e.g., a vapor having greater than about 90% drug purity, is produced from film thicknesses of less than about 10 μm. Assuming unit density for atropine, a substrate area of about 0.8 cm$^2$ coated with a 5 μm thick drug film is required to accommodate the oral dose of 0.4 mg if a drug of 95% purity is desired. Selection of an atropine film thickness of about 1.7 μm generated a thermal vapor having drug-aerosol particles with less than 2% pyrolysis (i.e., greater than 98% drug purity). Selection of a film having a thickness of 1.7 μm requires a substrate area of at least about 2.4 cm$^2$ to accommodate a dose of 0.4 mg.

The drug-delivery article comprised of a substrate coated with a thin drug film is particularly suited, in another aspect of the invention, for forming a therapeutic inhalation dose of drug-aerosol particles. The inhalation route of drug administration offers several advantages for many drugs, including rapid uptake into the bloodstream, and avoidance of the first pass effect allowing for an inhalation dose of a drug that can be substantially less, e.g., one half, that required for oral dosing. Efficient aerosol delivery to the lungs requires that the particles have certain penetration and settling or diffusional characteristics. For larger particles, deposition in the deep lungs occurs by gravitational settling and requires particles to have an effective settling size, defined as mass median aerodynamic diameter (MMAD), of between 1-3.5 μm. For smaller particles, deposition to the deep lung occurs by a diffusional process that requires having a particle size in the 10-100 nm, typically 20-100 nm range. Particle sizes that fall in the range between 100 nm and 1 μm tend to have poor deposition and those above 3.5 μm tend to have poor penetration. Therefore, an inhalation drug-delivery device for deep lung delivery should produce an aerosol having particles in one of these two size ranges, preferably between about 1-3 μm MMAD.

Accordingly, a drug-supply article comprised of a substrate and having a drug composition film thickness selected to generate a thermal vapor having drug composition-aerosol particles with less than about 10% drug degradation product is provided, more preferably less than about 5% drug degradation product, and most preferably less than about 2.5% drug degradation product. A gas, air or an inert fluid, is passed over the substrate at a flow rate effective to produce the particles having a desired MMAD. The more rapid the airflow, the more diluted the vapor and hence the smaller the particles that are formed. In other words the particle size distribution of the aerosol is determined by the concentration of the compound vapor during condensation. This vapor concentration is, in turn, determined by the extent to which airflow over the surface of the heating substrate dilutes the evolved vapor. Thus, to achieve smaller or larger particles, the gas velocity through the condensation region of the chamber may be altered by modifying the gas-flow control valve to increase or decrease the volumetric airflow rate. For example, to produce condensation particles in the size range 1-3.5 μm MMAD, the chamber may have substantially smooth-surfaced walls, and the selected gas-flow rate may be in the range of 4-50 L/minute.

Additionally, as will be appreciated by one of skill in the art, particle size may be also altered by modifying the cross-section of the chamber condensation region to increase or decrease linear gas velocity for a given volumetric flow rate, and/or the presence or absence of structures that produce turbulence within the chamber. Thus, for example to produce condensation particles in the size range 20-100 nm MMAD, the chamber may provide gas-flow barriers for creating air turbulence within the condensation chamber. These barriers are typically placed within a few thousands of an inch from the substrate surface.

Typically, the flow rate of gas over the substrate ranges from about 4-50 L/min, preferably from about 5-30 L/min.

Prior to, simultaneous with, or subsequent to passing a gas over the substrate, heat is applied to the substrate to vaporize the drug composition film. It will be appreciated that the temperature to which the substrate is heated will vary according to the drug's vaporization properties, but is typically heated to a temperature of at least about 200° C., preferably of at least about 250° C., more preferably at least about 300° C. or 350° C. Heating the substrate produces a drug composition vapor that in the presence of the flowing gas generates aerosol particles in the desired size range. In one embodiment, the substrate is heated for a period of less than about 1 second, and more preferably for less than about 500 milliseconds, still more preferably for less than about 200 milliseconds. The drug-aerosol particles are inhaled by a subject for delivery to the lung.

IV. Utility: Rapid-heating Device and Method

In another general embodiment, there is provided a device for producing an aerosol of compound condensation particles, e.g., for use in inhalation therapy. The device has the elements described above with respect to FIGS. 2A and 2B, where the heat source is designed to supply heat to the substrate in the device at a rate effective to produce a substrate temperature greater than 200° C. or in other embodiments greater than 250° C., 300° C. or 350° C., and to substantially volatilize the drug composition film from the substrate in a period of 2 seconds or less. The thickness of the film of drug composition on the substrate is such that the device produces an aerosol containing less than 10% by weight drug degradation and at least 50% of the drug composition on the film.

The device includes a drug composition delivery assembly composed of the substrate, a film of the selected drug composition on the substrate surface, and a heat source for supplying heat to the substrate at a rate effective to heat the substrate to a temperature greater than 200° C. or in other embodiments to a temperature greater than 250° C., 300° C. or 350° C., and to produce substantially complete volatilization of the drug composition within a period of 2 seconds or less.

The drug composition in the assembly and device may be one that, when vaporized from a film on an impermeable surface of a heat conductive substrate, the aerosol exhibits an increasing level of drug degradation products with increasing film thicknesses, particularly at a thickness of greater than 0.05-20 microns. For this general group of drug compositions, the film thickness on the substrate will typically be between 0.05 and 20 microns, e.g., the maximum or near-maximum thickness within this range that allows formation of a particle aerosol with drug degradation less than 5%.

Alternatively, the drug may show less than 5-10% degradation even at film thicknesses greater than 20 microns. For these compounds, a film thickness greater than 20 microns, e.g., 20-50 microns, may be selected, particularly where a relatively large drug dose is desired.

The device is useful in a method for producing a condensation aerosol by the steps of heating the device substrate at a rate that heats the substrate to a temperature greater than 200° C., or in other embodiments to a temperature greater than 250° C., 300° C., or 350° C., and produces substantially complete volatilization of the compounds within a period of 2 seconds or less.

V. EXAMPLES

The following examples further illustrate the invention described herein and are in no way intended to limit the scope of the invention.

Materials

Solvents were of reagent grade or better and purchased commercially.

Unless stated otherwise, the drug free base or free acid form was used in the Examples.

Methods

A. Preparation of Drug-Coating Solution

Drug was dissolved in an appropriate solvent. Common solvent choices included methanol, dichloromethane, methyl ethyl ketone, diethyl ether, 3:1 chloroform:methanol mixture, 1:1 dichloromethane:methyl ethyl ketone mixture, dimethylformamide, and deionized water. Sonication and/or heat were used as necessary to dissolve the compound. The drug concentration was typically between 50-200 mg/mL.

B. Preparation of Drug-Coated Stainless Steel Foil Substrate

Strips of clean 304 stainless steel foil (0.0125 cm thick, Thin Metal Sales) having dimensions 1.3 cm by 7.0 cm were dip-coated with a drug solution. The foil was then partially dipped three times into solvent to rinse drug off of the last 2-3 cm of the dipped end of the foil. Alternatively, the drug coating from this area was carefully scraped off with a razor blade. The final coated area was between 2.0-2.5 cm by 1.3 cm on both sides of the foil, for a total area of between 5.2-6.5 $cm^2$ Foils were prepared as stated above and then some were extracted with methanol or acetonitrile as standards. The amount of drug was determined from quantitative HPLC analysis. Using the known drug-coated surface area, the thickness was then obtained by:

$$\text{film thickness (cm)}=\text{drug mass (g)}/[\text{drug density (g/cm}^3)\times\text{substrate area (cm}^2).$$

If the drug density is not known, a value of 1 $g/cm^3$ is assumed. The film thickness in microns is obtained by multiplying the film thickness in cm by 10,000.

After drying, the drug-coated foil was placed into a volatilization chamber constructed of a Delrin® block (the airway) and brass bars, which served as electrodes. The dimensions of the airway were 1.3 cm high by 2.6 cm wide by 8.9 cm long. The drug-coated foil was placed into the volatilization chamber such that the drug-coated section was between the two sets of electrodes. After securing the top of the volatilization chamber, the electrodes were connected to a 1 Farad capacitor (Phoenix Gold). The back of the volatilization chamber was connected to a two micron Teflon® filter (Savillex) and filter housing, which were in turn connected to the house vacuum. Sufficient airflow was initiated (typically 30 L/min=1.5 m/sec), at which point the capacitor was charged with a power supply, typically to between 14-17 Volts. The circuit was closed with a switch, causing the drug-coated foil to resistively heat to temperatures of about 280-430° C. (as measured with an infrared camera (FLIR Thermacam SC3000)), in about 200 milliseconds. (For comparison purposes, see FIG. 4A, thermocouple measurement in still air.) After the drug had vaporized, airflow was stopped and the Teflon® filter was extracted with acetonitrile. Drug extracted from the filter was analyzed generally by HPLC UV absorbance generally at 225 nm using a gradient method aimed at detection of impurities to determine percent purity. Also, the extracted drug was quantified to determine a percent yield, based on the mass of drug initially coated onto the substrate. A percent recovery was determined by quantifying any drug remaining on the substrate and chamber walls, adding this to the quantity of drug recovered in the filter and comparing it to the mass of drug initially coated onto the substrate.

C. Preparation of Drug-Coated Aluminum Foil Substrate

A substrate of aluminum foil (10 cm×5.5 cm; 0.0005 inches thick) was precleaned with acetone. A solution of drug in a minimal amount of solvent was coated onto the foil substrate to cover an area of approximately 7-8 cm×2.5 cm. The solvent was allowed to evaporate. The coated foil was wrapped around a 300 watt halogen tube (Feit Electric Company, Pico Rivera, Calif.), which was inserted into a glass tube sealed at one end with a rubber stopper. Sixty volts of alternating current (driven by line power controlled by a Variac) were run through the bulb for 5-15 seconds, or in some studies 90 V for 3.5-6 seconds, to generate a thermal vapor (including aerosol) which was collected on the glass tube walls. In some studies, the system was flushed through with argon prior to volatilization. The material collected on the glass tube walls was recovered and the following determinations were made: (1) the amount emitted, (2) the percent emitted, and (3) the purity of the aerosol by reverse-phase HPLC analysis with detection typically by absorption of 225 nm light. The initial drug mass was found by weighing the aluminum foil substrate prior to and after drug coating. The drug coating thickness was calculated in the same manner as described in Method B.

D. Preparation of Drug-Coated Stainless Steel Cylindrical Substrate

A hollow stainless steel cylinder with thin walls, typically 0.12 mm wall thickness, a diameter of 13 mm, and a length of 34 mm was cleaned in dichloromethane, methanol, and acetone, then dried, and fired at least once to remove any residual volatile material and to thermally passivate the stainless steel surface. The substrate was then dip-coated with a drug coating solution (prepared as disclosed in Method A). The dip-coating was done using a computerized dip-coating machine to produce a thin layer of drug on the outside of the substrate surface. The substrate was lowered into the drug solution and then removed from the solvent at a rate of typically 5-25 cm/sec. (To coat larger amounts of material on the substrate, the substrate was removed more rapidly from the solvent or the solution used was more concentrated.) The substrate was then allowed to dry for 30 minutes inside a fume hood. If either dimethylformamide (DMF) or a water mixture was used as a dip-coating solvent, the substrate was vacuum dried inside a desiccator for a minimum of one hour. The drug-coated portion of the cylinder generally has a surface area of 8 $cm^2$. By assuming a unit density for the drug, the initial drug coating thickness was calculated. The amount of drug coated onto the substrates was determined in the same manner as that described in Method B: the substrates were coated, then extracted with methanol or acetonitrile and analyzed with quantitative HPLC methods, to determine the mass of drug coated onto the substrate.

The drug-coated substrate was placed in a surrounding glass tube connected at the exit end via Tygon® tubing to a filter holder fitted with a Teflon® filter (Savillex). The junction of the tubing and the filter was sealed with paraffin film. The substrate was placed in a fitting for connection to two 1 Farad capacitors wired in parallel and controlled by a high current relay. The capacitors were charged by a separate power source to about 18-22 Volts and most of the power was channeled to the substrate by closing a switch and allowing the capacitors to discharge into the substrate. The substrate was heated to a temperature of between about 300-500° C. (see FIGS. 5A & 5B) in about 100 milliseconds. The heating process was done under an airflow of 15 L/min, which swept the vaporized drug aerosol into a 2 micron Teflon® filter.

After volatilization, the aerosol captured on the filter was recovered for quantification and analysis. The quantity of material recovered in the filter was used to determine a percent yield, based on the mass of drug coated onto the substrate. The material recovered in the filter was also analyzed generally by HPLC UV absorbance at typically 225 nm using a gradient method aimed at detection of impurities, to determine purity of the thermal vapor. Any material deposited on the glass sleeve or remaining on the substrate was also recovered and quantified to determine a percent total recovery ((mass of drug in filter+mass of drug remaining on substrate and glass sleeve)/mass of drug coated onto substrate). For compounds without UV absorption GC/MS or LC/MS was used to determine purity and to quantify the recovery. Some samples were further analyzed by LC/MS to confirm the molecular weight of the drug and any degradants.

E. Preparation of Drug-Coated Stainless Steel Cylindrical Substrate

A hollow stainless steel cylinder like that described in Example D was prepared, except the cylinder diameter was 7.6 mm and the length was 51 mm. A film of a selected drug was applied as described in Example D.

Energy for substrate heating and drug vaporization was supplied by two capacitors (1 Farad and 0.5 Farad) connected in parallel, charged to 20.5 Volts. The airway, airflow, and other parts of the electrical set up were as described in Example D. The substrate was heated to a temperature of about 420° C. in about 50 milliseconds. After drug film vaporization, percent yield, percent recovery, and purity analysis were done as described in Example D.

F. Preparation of Drug-Coated Aluminum Foil Substrate

A solution of drug was coated onto a substrate of aluminum foil (5 cm²-150 cm²; 0.0005 inches thick). In some studies, the drug was in a minimal amount of solvent, which was allowed to evaporate. The coated foil was inserted into a glass tube in a furnace (tube furnace). A glass wool plug was placed in the tube adjacent to the foil sheet and an air flow of 2 L/min was applied. The furnace was heated to 200-550° C. for 30, 60, or 120 seconds. The material collected on the glass wool plug was recovered and analyzed by reverse-phase HPLC analysis with detection typically by absorption of 225 nm light or GC/MS to determine the purity of the aerosol.

G. Preparation of Drug-Coated Aluminum Foil Substrate

A substrate of aluminum foil (3.5 cm×7 cm; 0.0005 inches thick) was precleaned with acetone. A solution of drug in a minimal amount of solvent was coated onto the foil substrate. The solvent was allowed to evaporate. The coated foil was wrapped around a 300 watt halogen tube (Feit Electric Company, Pico Rivera, Calif.), which was inserted into a T-shaped glass tube sealed at two ends with parafilm. The parafilm was punctured with ten to fifteen needles for air flow. The third opening was connected to a 1 liter, 3-neck glass flask. The glass flask was further connected to a piston capable of drawing 1.1 liters of air through the flask. Ninety volts of alternating current (driven by line power controlled by a Variac) was run through the bulb for 6-7 seconds to generate a thermal vapor (including aerosol) which was drawn into the 1 liter flask. The aerosol was allowed to sediment onto the walls of the 1 liter flask for 30 minutes. The material collected on the flask walls was recovered and the following determinations were made: (1) the amount emitted, (2) the percent emitted, and (3) the purity of the aerosol by reverse-phase HPLC analysis with detection by typically by absorption of 225 nm light. Additionally, any material remaining on the substrate was collected and quantified.

Example 1

Acebutolol (MW 336, melting point 123° C., oral dose 400 mg), a beta adrenergic blocker (cardiovascular agent), was coated on a stainless steel cylinder (8 cm²) according to Method D. 0.89 mg of drug was applied to the substrate, for a calculated drug film thickness of 1.1 μm. The substrate was heated as described in Method D at 20.5 V and purity of the drug-aerosol particles were determined to be 98.9%. 0.53 mg was recovered from the filter after vaporization, for a percent yield of 59.6%. A total mass of 0.81 mg was recovered from the test apparatus and substrate, for a total recovery of 91%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 130 milliseconds. Generation of the thermal vapor was complete by 500 milliseconds.

Example 2

Acetaminophen (MW 151, melting point 171° C., oral dose 650 mg), an analgesic agent, was coated on an aluminum foil substrate (20 cm²) according to Method C. 2.90 mg of drug was applied to the substrate, for a calculated thickness of the drug film of 1.5 μm. The substrate was heated under argon as described in Method C at 60 V for 6 seconds. The purity of the drug-aerosol particles were determined to be >99.5%. 1.9 mg was recovered from the glass tube walls after vaporization, for a percent yield of 65.5%.

Example 3

Albuterol (MW 239, melting point 158° C., oral dose 0.18 mg), a bronchodilator, was coated onto six stainless steel foil substrates (5 cm²) according to Method B. The calculated thickness of the drug film on each substrate ranged from about 1.5 μm to about 6.1 μm. The substrates were heated as described in Method B by charging the capacitors to 15 V. Purity of the drug-aerosol particles from each substrate was determined and the results are shown in FIG. 23.

Albuterol was also coated on a stainless steel cylinder (8 cm²) according to Method D. 1.20 mg of drug was applied to the substrate, for a calculated drug film thickness of 2.4 μm. The substrate was heated as described in Method D by charging the capacitors to 20.5 V. The purity of the drug-aerosol particles was determined to be 94.4%. 0.69 mg was recovered from the filter after vaporization, for a percent yield of 57.2%. A total mass of 0.9 mg was recovered from the test apparatus and substrate, for a total recovery of 73.5%.

Example 4

Figure 21:
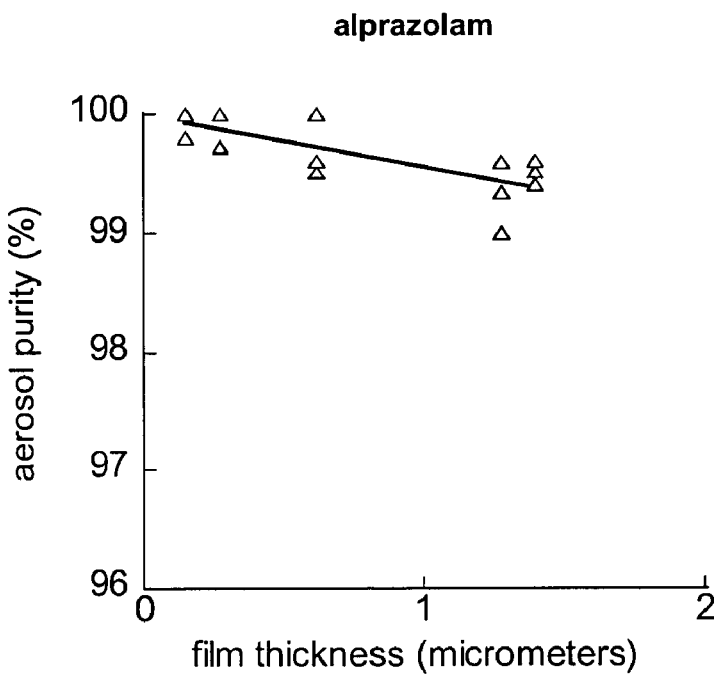
FIG. 21 is plot showing purity of thermal vapor as a function of drug film thickness, in micrometers, for alprazolam free base.
Figure 22:
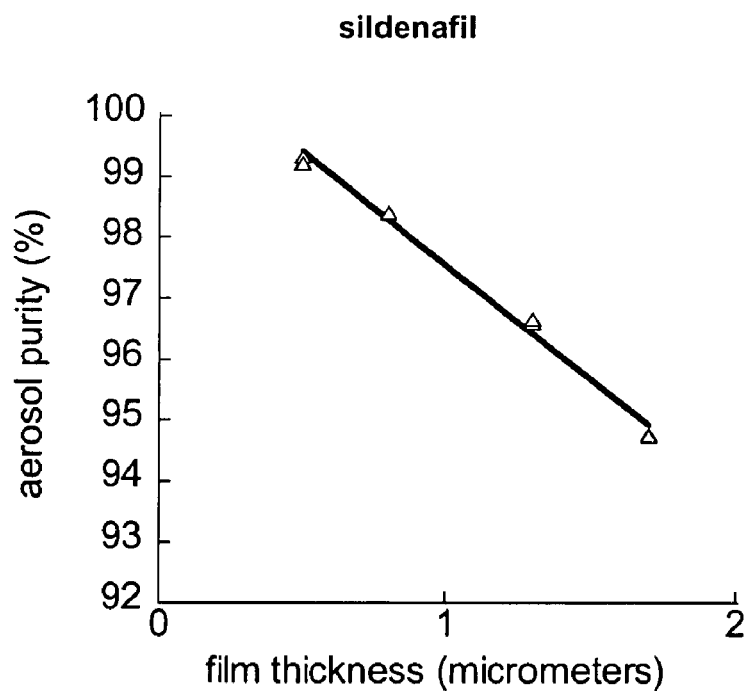
FIG. 22 is plot showing purity of thermal vapor as a function of drug film thickness, in micrometers, for sildenafil free base.

Alprazolam (MW 309, melting point 229° C., oral dose 0.25 mg), an anti-anxiety agent (Xanax®), was coated onto 13 stainless steel cylinder substrates (8 cm$^2$) according to Method D. The calculated thickness of the drug film on each substrate ranged from about 0.1 µm to about 1.4 µm. The substrates were heated as described in Method D by charging the capacitors to 20.5 V. Purity of the drug-aerosol particles from each substrate was determined and the results are shown in FIG. 21.

Another substrate (stainless steel cylinder, 8 cm$^2$) was coated with 0.92 mg of drug, for a calculated drug film thickness of 1.2 µm. The substrate was heated as described in Method D by charging the capacitors to 22.5 V. Purity of the drug-aerosol particles was 99.8%. 0.61 mg was recovered from the filter after vaporization, for a percent yield of 66.2%. A total mass of 0.92 mg was recovered from the test apparatus and substrate, for a total recovery of 100%.

Alprazolam was also coated on an aluminum foil substrate (28.8 cm$^2$) according to Method C. 2.6 mg of the drug was coated on the substrate for a calculated thickness of the drug film of 0.9 µm. The substrate was heated substantially as described in Method C at 75 V for 6 seconds. The purity of the drug-aerosol particles was determined to be 99.9%.

High speed photographs were taken as the drug-coated substrate according to Method D was heated to monitor visually formation of a thermal vapor. The photographs showed that a thermal vapor was initially visible ~35 milliseconds after heating was initiated, with the majority of the thermal vapor formed by 100 milliseconds. Generation of the thermal vapor was complete by 400 milliseconds.

Example 5

Amantadine (MW 151, melting point 192° C., oral dose 100 mg), a dopaminergic agent and an anti-infective agent, was coated on an aluminum foil substrate (20 $cm^2$) according to Method C. A mass of 1.6 mg was coated onto the substrate and the calculated thickness of the drug film was 0.8 μm. The substrate was heated as described in Method C at 90 V for 4 seconds. The purity of the drug-aerosol particles was determined to be 100%. 1.5 mg was recovered from the glass tube walls after vaporization, for a percent yield of 93.8%.

Example 6

Amitriptyline (MW 277, oral dose 50 mg), a tricyclic antidepressant, was coated on a piece of aluminum foil (20 $cm^2$) according to Method C. The calculated thickness of the drug film was 5.2 μm. The substrate was heated as described in Method C at 90 V for 5 seconds. The purity of the drug-aerosol particles was determined to be 98.4%. 5.3 mg was recovered from the glass tube walls after vaporization, for a percent yield of 51.5%.

Amitriptyline was also coated on an identical substrate to a thickness of 1.1 μm. The substrate was heated as described in Method C under an argon atmosphere at 90 V for 3.5 seconds. The purity of the drug-aerosol particles was determined to be 99.3%. 1.4 mg was recovered from the glass tube walls after vaporization, for a percent yield of 63.6%.

Example 7

Apomorphine diacetate (MW 351), a dopaminergic agent used as an anti-Parkinsonian drug, was coated on a piece of aluminum foil (20 $cm^2$) according to Method C. The calculated thickness of the drug film was 1.1 μm. The substrate was heated as described in Method C at 90 V for 3 seconds. The purity of the drug-aerosol particles was determined to be 96.9%. 2 mg was recovered from the glass tube walls after vaporization, for a percent yield of 90.9%.

Example 8

The hydrochloride salt form of apomorphine was also tested. Apomorphine hydrochloride (MW 304) was coated on a stainless steel foil (6 $cm^2$) according to Method B. 0.68 mg of drug was applied to the substrate, for a calculated drug film thickness of 1.1 μm. The substrate was heated as described in Method B by charging the capacitor to 15 V. The purity of the drug-aerosol particles was determined to be 98.1%. 0.6 mg was recovered from the filter after vaporization, for a percent yield of 88.2%. A total mass of 0.68 mg was recovered from the test apparatus and substrate, for a total recovery of 100%.

Example 9

The hydrochloride diacetate salt of apomorphine was also tested (MW 388). Apomorphine hydrochloride diacetate was coated on a piece of aluminum foil (20 $cm^2$) according to Method C. The calculated thickness of the drug film was 1.0 μm. The substrate was heated as described in Method C at 90 V for 3 second purity of the drug-aerosol particles was determined to be 94.0%. 1.65 mg was recovered from the glass tube walls after vaporization, for a percent yield of 86.8%.

Example 10

Atropine (MW 289, melting point 116° C., oral dose 0.4 mg), an muscarinic antagonist, was coated on five stainless steel cylinder substrates (8 $cm^2$) according to Method D. The calculated thickness of the drug films ranged from about 1.7 μm to 9.0 μm. The substrate was heated as described in Method D by charging the capacitors to 19 or 22 V. Purity of the drug-aerosol particles from each substrate was determined. The results are shown in FIG. 6. For the substrate having a drug film thickness of 1.7 μm, 1.43 mg of drug was applied to the substrate. After volatilization of drug from this substrate with a capacitor charged to 22 V, 0.95 mg was recovered from the filter, for a percent yield of 66.6%. The purity of the drug aerosol recovered from the filter was found to be 98.5%. A total mass of 1.4 mg was recovered from the test apparatus and substrate, for a total recovery of 98.2%.

High speed photographs were taken as the drug-coated substrate was heated to monitor visually formation of a thermal vapor. The photographs showed that a thermal vapor was initially visible 28 milliseconds after heating was initiated, with the majority of the thermal vapor formed by 90 milliseconds. Generation of the thermal vapor was complete by 140 milliseconds.

Example 11

Azatadine (MW 290, melting point 126° C., oral dose 1 mg), an antihistamine, was coated on an aluminum foil substrate (20 $cm^2$) according to Method C. 5.70 mg of drug was applied to the substrate, for a calculated thickness of the drug film of 2.9 μm. The substrate was heated as described in Method C at 60 V for 6 seconds. The purity of the drug-aerosol particles was determined to be 99.6%. 2.8 mg was recovered from the glass tube walls after vaporization, for a percent yield of 49.1%.

Another azatadine coated substrate was prepared according to Method G. The substrate was heated as described in Method G at 60 V for 6 seconds under an argon atmosphere. The purity of the drug-aerosol particles was determined to be 99.6%. The percent yield of the aerosol was 62%.

Example 12

Bergapten (MW 216, melting point 188° C., oral dose 35 mg), an anti-psoriatic agent, was coated on a stainless steel cylinder (8 $cm^2$) according to Method D. 1.06 mg of drug was applied to the substrate, for a calculated drug film thickness of 1.3 μm. The substrate was heated as described in Method D by charging the capacitors to 20.5 V. The purity of the drug-aerosol particles was determined to be 97.8%. 0.72 mg was recovered from the filter after vaporization, for a percent yield of 67.9%. A total mass of 1.0 mg was recovered from the test apparatus and substrate, for a total recovery of 98.1%.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 85 milliseconds. Generation of the thermal vapor was complete by 140 milliseconds.

Example 13

Betahistine (MW 136, melting point <25° C., oral dose 8 mg), a vertigo agent, was coated on a metal substrate according to Method F and heated to 300° C. to form drug-aerosol particles. Purity of the drug-aerosol particles was determined to be 99.3%. 17.54 mg was recovered from the glass wool after vaporization, for a percent yield of 58.5%.

Example 14

Brompheniramine (MW 319, melting point <25° C., oral dose 4 mg), an anti-histamine agent, was coated on an aluminum foil substrate (20 $cm^2$) according to Method C. 4.50 mg of drug was applied to the substrate, for a calculated thickness of the drug film of 2.3 μm. The substrate was heated as described in Method C at 60 V for 8 seconds. The purity of the drug-aerosol particles was determined to be 99.8%. 3.12 mg was recovered from the glass tube walls after vaporization, for a percent yield of 69.3%.

An identical substrate with the same thickness of brompheniramine (4.5 mg drug applied to substrate) was heated under an argon atmosphere at 60 V for 8 seconds. The purity of the drug-aerosol particles was determined to be 99.9%. 3.3 mg was recovered from the glass tube walls after vaporization, for a percent yield of 73.3%.

The maleate salt form of the drug was also tested. Brompheniramine maleate (MW 435, melting point 134° C., oral dose 2 mg) was coated onto an aluminum foil substrate (20 $cm^2$) according to Method C. The calculated thickness of the drug film was 2.8 μm. The substrate was heated as described in Method C at 60 V for 7 seconds. The purity of the drug-aerosol particles was determined to be 99.6%. 3.4 mg was recovered from the glass tube walls after vaporization, for a percent yield of 60.7%.

An identical substrate with a 3.2 μm brompheniramine maleate film was heated under an argon atmosphere at 60 V for 7 seconds. The purity of the drug-aerosol particles was determined to be 100%. 3.2 mg was recovered from the glass tube walls after vaporization, for a percent yield of 50%.

Example 15

Bumetanide (MW 364, melting point 231° C., oral dose 0.5 mg), a cardiovascular agent and diuretic, was coated on a stainless steel cylinder (8 $cm^2$) according to Method D. 1.09 mg of drug was applied to the substrate, for a calculated drug film thickness of 1.3 μm. The substrate was heated as described in Method D by charging the capacitors to 20.5 V. The purity of the drug-aerosol particles was determined to be 98.4%. 0.56 mg was recovered from the filter after vaporization, for a percent yield of 51.4%. A total mass of 0.9 mg was recovered from the test apparatus and substrate, for a total recovery of 82.6%.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 300 milliseconds. Generation of the thermal vapor was complete by 1200 milliseconds.

Example 16

Buprenorphine (MW 468, melting point 209° C., oral dose 0.3 mg), an analgesic narcotic, was coated on a piece of aluminum foil (20 $cm^2$) according to Method C. The calculated thickness of the drug film was 0.7 μm. The substrate was heated as described in Method C at 60 V for 5 seconds. The purity of the drug-aerosol particles was determined to be 98%. 1.34 mg was recovered from the glass tube walls after vaporization, for a percent yield of 95.7%.

Buprenorphine was also coated onto five stainless steel cylinder substrates (8 $cm^2$) according to Method D except that a 1.5 Farad capacitor was used as opposed to a 2.0 Farad capacitor. The calculated thickness of the drug film on each substrate ranged from about 0.3 μm to about 1.5 μm. The substrates were heated as described in Method D (with the single exception that the circuit capacitance was 1.5 Farad, not 2.0 Farad) and purity of the drug-aerosol particles determined. The results are shown in FIG. 9. For the substrate having a 1.5 μm drug film, 1.24 mg of drug was applied to the substrate. After volatilization of drug from this substrate by charging the capacitors to 20.5 V, 0.865 mg was recovered from the filter, for a percent yield of 69.5%. A total mass of 1.2 mg was recovered from the test apparatus and substrate, for a total recovery of 92.9%. The purity of the drug aerosol recovered from the filter was determined to be 97.1%.

High speed photographs were taken as one of the drug-coated substrates was heated, to monitor visually formation of a thermal vapor. The photographs, shown in FIGS. 26A-26E, showed that a thermal vapor was initially visible 30 milliseconds after heating was initiated, with the majority of the thermal vapor formed by 120 milliseconds. Generation of the thermal vapor was complete by 300 milliseconds.

The salt form of the drug, buprenorphine hydrochloride (MW 504), was also tested. The drug was coated on a piece of aluminum foil (20 $cm^2$) according to Method C. 2.10 mg of drug was applied to the substrate, for a calculated thickness of the drug film of 1.1 μm. The substrate was heated as described in Method C at 60 V for 15 seconds. The purity of the drug-aerosol particles was determined to be 91.4%. 1.37 mg was recovered from the glass tube walls after vaporization, for a percent yield of 65.2%.

Buprenorphine was further coated on an aluminum foil substrate (24.5 $cm^2$) according to Method G. 1.2 mg of the drug was applied to the substrate, for a calculated thickness of the drug film of 0.49 μm. The substrate was heated substantially as described in Method G at 90 V for 6 seconds, except that two of the openings of the T-shaped tube were left open and the third connected to the 1 L flask. The purity of the drug-aerosol particles was determined to be >99%. 0.7 mg of the drug was found to have aerosolized, for a percent yield of 58%.

Example 17

Bupropion hydrochloride (MW 276, melting point 234° C., oral dose 100 mg), an antidepressant psychotherapeutic agent, was coated on a piece of aluminum foil (20 cm$^2$) according to Method C. The calculated thickness of the drug film was 1.2 µm. The substrate was heated as described in Method C at 90 V for 3.5 seconds. The purity of the drug-aerosol particles was determined to be 98.5%. 2.1 mg was recovered from the glass tube walls after vaporization, for a percent yield of 91.3%. An identical substrate having the same drug film thickness was heated under an argon atmosphere according to Method C at 90 V for 3.5 seconds. 1.8 mg was recovered from the glass tube walls after vaporization, for a percent yield of 78.3%. The recovered vapor had a purity of 99.1%.

Example 18

Butalbital (MW 224, melting point 139° C., oral dose 50 mg), a sedative and hypnotic barbituate, was coated on a piece of aluminum foil (20 cm$^2$) according to Method C. 2.3 mg were coated on the foil, for a calculated thickness of the drug film of 1.2 µm. The substrate was heated as described in Method C at 90 V for 3.5 seconds. The purity of the drug-aerosol particles was determined to be >99.5%. 1.69 mg were collected for a percent yield of 73%.

Example 19

Butorphanol (MW 327, melting point 217° C., oral dose 1 mg), an analgesic narcotic agent, was coated on a piece of aluminum foil (20 cm$^2$) according to Method C. The calculated thickness of the drug film was 1.0 µm. The substrate was heated as described in Method C at 90 V for 3.5 seconds. The purity of the drug-aerosol particles was determined to be 98.7%.

Butorphanol was also coated on a stainless steel cylinder (6 cm$^2$) according to Method E. 1.24 mg of drug was applied to the substrate, for a calculated drug film thickness of 2.1 µm. The substrate was heated as described in Method E and purity of the drug-aerosol particles was determined to be 99.4%. 0.802 mg was recovered from the filter after vaporization, for a percent yield of 64.7%. A total mass of 1.065 mg was recovered from the test apparatus and substrate, for a total recovery of 85.9%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 60 milliseconds. Generation of the thermal vapor was complete by 90 milliseconds.

Example 20

Carbinoxamine (MW 291, melting point <25° C., oral dose 2 mg), an antihistamine, was coated on a piece of aluminum foil (20 cm$^2$) according to Method C. 5.30 mg of drug was applied to the substrate, for a calculated thickness of the drug film of 2.7 µm. The substrate was heated as described in Method C at 60 V for 6 seconds. The purity of the drug-aerosol particles was determined to be 92.5%. 2.8 mg was recovered from the glass tube walls after vaporization, for a percent yield of 52.8%.

A second substrate was coated with carbinoxamine (6.5 mg drug) to a thickness of 3.3 µm. The substrate was heated as described in Method C at 90 V for 6 seconds under an argon atmosphere. The purity of the drug-aerosol particles determined was to be 94.8%. 3.1 mg was recovered from the glass tube walls after vaporization, for a percent yield of 47.7%.

The maleate salt form of the drug was also tested. Carbinoxamine maleate (MW 407, melting point 119° C., oral dose 4 mg) was coated on a piece of aluminum foil (20 cm$^2$) according to Method C. The calculated thickness of the drug film was 3.9 µm. The substrate was heated as described in Method C at 90 V for 6 seconds. The purity of the drug-aerosol particles was determined to be 99%. 4.8 mg was recovered from the glass tube walls after vaporization, for a percent yield of 62.3%.

Example 21

Celecoxib (MW 381, melting point 159° C., oral dose 100 mg), an analgesic non-steroidal anti-inflammatory agent, was coated on a piece of stainless steel foil (5 cm$^2$) according to Method B. 4.6 mg of drug was applied to the substrate, for a calculated drug film thickness of 8.7 µm. The substrate was heated as described in Method B by charging the capacitors to 16 V. The purity of the drug-aerosol particles was determined to be >99.5%. 4.5 mg was recovered from the filter after vaporization, for a percent yield of 97.8%. A total mass of 4.6 mg was recovered from the test apparatus and substrate, for a total recovery of 100%.

Celecoxib was also coated on a piece of aluminum foil (100 cm$^2$) according to Method G. The calculated thickness of the drug film was 3.1 µm. The substrate was heated as described in Method G at 60 V for 15 seconds. The purity of the drug-aerosol particles was determined to be 99%. 24.5 mg was recovered from the glass tube walls after vaporization, for a percent yield of 79%.

Example 22

Chlordiazepoxide (MW 300, melting point 237° C., oral dose 5 mg), a sedative and hypnotic agent, was coated on a piece of aluminum foil (20 cm$^2$) according to Method C. The calculated thickness of the drug film was 2.3 µm. The substrate was heated as described in Method C at 45 V for 15 seconds. The purity of the drug-aerosol particles was determined to be 98.2%. 2.5 mg was recovered from the glass tube walls after vaporization, for a percent yield of 54.3%.

Example 23

Chlorpheniramine (MW 275, melting point <25° C., oral dose 4 mg), an antihistamine, was coated onto an aluminum foil substrate (20 cm$^2$) according to Method C. 5.90 mg of drug was applied to the substrate, for a calculated thickness of the drug film of 3 µm. The substrate was heated as described in Method C at 60 V for 10 seconds. The purity of the drug-aerosol particles was determined to be 99.8%. 4.14 mg was recovered from the glass tube walls after vaporization, for a percent yield of 70.2%.

The maleate salt form (MW 391, melting point 135° C., oral dose 8 mg) was coated on an identical substrate to a thickness of 1.6 µm. The substrate was heated as described in Method C at 60 V for 7 seconds. The purity of the drug-aerosol particles was determined to be 99.6%. 2.1 mg was recovered from the glass tube walls after vaporization, for a percent yield of 65.6%.

Example 24

Chlorpromazine (MW 319, melting point <25° C., oral dose 300 mg), an antipsychotic, psychotherapeutic agent, was coated on an aluminum foil substrate (20 cm$^2$) according to Method C. 9.60 mg of drug was applied to the substrate, for a calculated thickness of the drug film of 4.8 μm. The substrate was heated as described in Method C at 90 V for 5 seconds. The purity of the drug-aerosol particles was determined to be 96.5%. 8.6 mg was recovered from the glass tube walls after vaporization, for a percent yield of 89.6%.

Example 25

Chlorzoxazone (MW 170, melting point 192° C., oral dose 250 mg), a muscle relaxant, was coated on a piece of aluminum foil (20 $cm^2$) according to Method C. The calculated thickness of the drug film was 1.3 μm. The substrate was heated as described in Method C at 90 V for 3.5 seconds. The purity of the drug-aerosol particles was determined to be 99.7%. 1.55 mg was recovered from the glass tube walls after vaporization, for a percent yield of 59.6%.

Example 26

Ciclesonide free base (MW 541, melting point 206.5-207° C., oral dose 0.2 mg) a glucocorticoid, was coated on stainless steel foil substrates (6 $cm^2$) according to Method B. Eight substrates were prepared, with the drug film thickness ranging from about 0.4 μm to about 2.4 μm. The substrates were heated as described in Method B, with the capacitors charged with 15.0 or 15.5 V. Purity of the drug-aerosol particles from each substrate was determined and the results are shown in FIG. 11. The substrate having a thickness of 0.4 μm was prepared by depositing 0.204 mg drug on the substrate surface. After volatilization of drug from this substrate using capacitors charged to 15.0 V, 0.201 mg was recovered from the filter, for a percent yield of 98.5%. The purity of the drug aerosol particles was determined to be 99%. A total mass of 0.204 mg was recovered from the test apparatus and substrate, for a total recovery of 100%.

Example 27

Citalopram (MW 324, melting point <25° C., oral dose 20 mg), a psychotherapeutic agent, was coated onto an aluminum foil substrate (20 $cm^2$) according to Method C. 8.80 mg of drug was applied to the substrate, for a calculated thickness of the drug film of 4.4 μm. The substrate was heated as described in Method C at 90 V for 4 seconds. The purity of the drug-aerosol particles was determined to be 92.3%. 5.5 mg was recovered from the glass tube walls after vaporization, for a percent yield of 62.5%.

Another substrate containing citalopram coated (10.10 mg drug) to a film thickness of 5 μm was prepared by the same method and heated under an argon atmosphere. The purity of the drug-aerosol particles was determined to be 98%. 7.2 mg was recovered from the glass tube walls after vaporization, for a percent yield of 71.3%.

Example 28

Clomipramine (MW 315, melting point <25° C., oral dose 150 mg), a psychotherapeutic agent, was coated onto eight stainless steel cylindrical substrates according to Method E. The calculated thickness of the drug film on each substrate ranged from about 0.8 μm to about 3.9 μm. The substrates were heated as described in Method E and purity of the drug-aerosol particles determined. The results are shown in FIG. 10. For the substrate having a drug film thickness of 0.8 μm, 0.46 mg of drug was applied to the substrate. After volatilization of drug from this substrate, 0.33 mg was recovered from the filter, for a percent yield of 71.7%. Purity of the drug-aerosol particles was determined to be 99.4%. A total mass of 0.406 mg was recovered from the test apparatus and substrate, for a total recovery of 88.3%.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 75 milliseconds. Generation of the thermal vapor was complete by 115 milliseconds.

Example 29

Clonazepam (MW 316, melting point 239° C., oral dose 1 mg), an anticonvulsant, was coated on an aluminum foil substrate (50 $cm^2$) and heated according to Method F to a temperature of 350° C. to form drug-aerosol particles. 46.4 mg of the drug was applied to the substrate, for a calculated thickness of the drug film of 9.3 μm. Purity of the drug-aerosol particles was determined to be 14%.

Clonazepam was further coated on an aluminum foil substrate (24 $cm^2$) according to Method C. 5 mg of the drug was applied to the substrate, for a calculated thickness of the drug film of 2.1 μm. The substrate was heated substantially as described in Method C at 60 V for 8 seconds. The purity of the drug-aerosol particles was determined to be 99.9%.

Example 30

Clonidine (MW 230, melting point 130° C., oral dose 0.1 mg), a cardiovascular agent, was coated on an aluminum foil substrate (50 $cm^2$) and heated according to Method F at 300° C. to form drug-aerosol particles. Purity of the drug-aerosol particles was determined to be 94.9%. The yield of aerosol particles was 90.9%.

Example 31

Clozapine (MW 327, melting point 184° C., oral dose 150 mg), a psychotherapeutic agent, was coated on an aluminum foil substrate (20 $cm^2$) according to Method C. 14.30 mg of drug was applied to the substrate, for a calculated thickness of the drug film of 7.2 μm. The substrate was heated as described in Method C at 90 V for 5 seconds. The purity of the drug-aerosol particles was determined to be 99.1%. 2.7 mg was recovered from the glass tube walls after vaporization, for a percent yield of 18.9%.

Another substrate containing clozapine coated (2.50 mg drug) to a film thickness of 1.3 μm was prepared by the same method and heated under an argon atmosphere at 90 V for 3.5 seconds. The purity of the drug-aerosol particles was determined to be 99.5%. 1.57 mg was recovered from the glass tube walls after vaporization, for a percent yield of 62.8%.

Example 32

Codeine (MW 299, melting point 156° C., oral dose 15 mg), an analgesic, was coated on an aluminum foil substrate (20 cm$^2$) according to Method C. 8.90 mg of drug was applied to the substrate, for a calculated thickness of the drug film of 4.5 μm. The substrate was heated as described in Method C at 90 V for 5 seconds. The purity of the drug-aerosol particles was determined to be 98.1%. 3.46 mg was recovered from the glass tube walls after vaporization, for a percent yield of 38.9%.

Another substrate containing codeine coated (2.0 mg drug) to a film thickness of 1 μm was prepared by the same method and heated under an argon atmosphere at 90 V for 3.5 seconds. The purity of the drug-aerosol particles was determined to be >99.5%. 1 mg was recovered from the glass tube walls after vaporization, for a percent yield of 50%.

Example 33

Colchicine (MW 399, melting point 157° C., oral dose 0.6 mg), a gout preparation, was coated on a stainless steel cylinder (8 cm$^2$) according to Method D. 1.12 mg of drug was applied to the substrate, for a calculated drug film thickness of 1.3 μm. The substrate was heated as described in Method D by charging the capacitors to 20.5 V. The purity of the drug-aerosol particles was determined to be 97.7%. 0.56 mg was recovered from the filter after vaporization, for a percent yield of 50%. A total mass of 1.12 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 140 milliseconds. Generation of the thermal vapor was complete by 700 milliseconds.

Example 34

Cyclobenzaprine (MW 275, melting point <25° C., oral dose 10 mg), a muscle relaxant, was coated on an aluminum foil substrate (20 cm$^2$) according to Method C. 9.0 mg of drug was applied to the substrate, for a calculated thickness of the drug film of 4.5 μm. The substrate was heated as described in Method C at 90 V for 5 seconds. The purity of the drug-aerosol particles was determined to be 99%. 6.33 mg was recovered from the glass tube walls after vaporization, for a percent yield of 70.3%.

Example 35

Cyproheptadine (MW 287, melting point 113° C., oral dose 4 mg), an antihistamine, was coated on an aluminum foil substrate (20 cm$^2$) according to Method C. 4.5 mg of drug was applied to the substrate, for a calculated thickness of the drug film of 2.3 μm. The substrate was heated as described in Method C at 60 V for 8 seconds. The purity of the drug-aerosol particles was determined to be >99.5%. 3.7 mg was recovered from the glass tube walls after vaporization, for a percent yield of 82.2%.

Cyproheptadine HCl salt (MW 324, melting point 216° C., oral dose 4 mg) was coated on an identical substrate to a thickness of 2.2 μm. The substrate was heated at 60V for 8 seconds. The purity of the drug-aerosol particles was determined to be 99.6%. 2.6 mg was recovered from the glass tube walls after vaporization, for a percent yield of 60.5%.

Example 36

Dapsone (MW 248, melting point 176° C., oral dose 50 mg), an anti-infective agent, was coated on a stainless steel cylinder (8 cm$^2$) according to Method D. 0.92 mg of drug was applied to the substrate, for a calculated drug film thickness of 1.1 μm. The substrate was heated as described in Method D by charging the capacitors to 20.5 V. The purity of the drug-aerosol particles was determined to be >99.5%. 0.92 mg was recovered from the filter after vaporization, for a percent yield of 100%. The total mass was recovered from the test apparatus and substrate, for a total recovery of about 100%.

Example 37

Diazepam (MW 285, melting point 126° C., oral dose 2 mg), a sedative and hypnotic, was coated on an aluminum foil substrate (20 cm$^2$) according to Method C. 5.30 mg of drug was applied to the substrate, for a calculated thickness of the drug film of 2.7 μm. The substrate was heated as described in Method C at 40 V for 17 seconds. The purity of the drug-aerosol particles were determined to be 99.9%. 4.2 mg was recovered from the glass tube walls after vaporization, for a percent yield of 79.2%.

Diazepam was also coated on a circular aluminum foil substrate (78.5 cm$^2$). 10.0 mg of drug was applied to the substrate, for a calculated film thickness of the drug of 1.27 μm. The substrate was secured to the open side of a petri dish (100 mm diameter×50 mm height) using parafilm. The glass bottom of the petri dish was cooled with dry ice, and the aluminum side of the apparatus was placed on a hot plate at 240° C. for 10 seconds. The material collected on the beaker walls was recovered and analyzed by HPLC analysis with detection by absorption of 225 nm light used to determine the purity of the aerosol. Purity of the drug-aerosol particles was determined to be 99.9%.

Diazepam was also coated on an aluminum foil substrate (36 cm$^2$) according to Method G. 5.1 mg of drug was applied to the substrate, for a calculated thickness of the drug film of 1.4 μm. The substrate was heated substantially as described in Method G, except that 90V for 6 seconds was used, and purity of the drug-aerosol particles was determined to be 99%. 3.8 mg was recovered from the glass tube walls after vaporization, for a percent yield of 74.5%.

Example 38

Diclofenac ethyl ester (MW 324, oral dose 50 mg), an antirheumatic agent, was coated on a metal substrate (50 cm$^2$) and heated according to Method F at 300° C. to form drug-aerosol particles. 50 mg of drug was applied to the substrate, for a calculated thickness of the drug film of 10 μm. Purity of the drug-aerosol particles was determined to be 100% by GC analysis. The yield of aerosol particles was 80%.

Example 39

Diflunisal (MW 250, melting point 211° C., oral dose 250 mg), an analgesic, was coated on a piece of aluminum foil ($20\ cm^2$) according to Method C. The calculated thickness of the drug film was 5.3 μm. The substrate was heated as described in Method C at 60 V for 6 seconds. The purity of the drug-aerosol particles was determined to be >99.5%. 5.47 mg was recovered from the glass tube walls after vaporization, for a percent yield of 51.6%.

Example 40

Diltiazem (MW 415, oral dose 30 mg), a calcium channel blocker used as a cardiovascular agent, was coated on a stainless steel cylinder ($8\ cm^2$) according to Method D. 0.8 mg of drug was applied to the substrate, for a calculated drug film thickness of 1 µm. The substrate was heated as described in Method D by charging the capacitors to 20.5V. The purity of the drug-aerosol particles was determined to be 94.2%. 0.53 mg was recovered from the filter after vaporization, for a percent yield of 66.3%. A total mass of 0.8 mg was recovered from the test apparatus and substrate, for a total recovery of 100%.

The drug was also coated on a piece of aluminum foil (20 cm$^2$) according to Method C. The calculated thickness of the drug film was 1.0 µm. The substrate was heated as described in Method C at 90 V for 3.5 seconds. The purity of the drug-aerosol particles was determined to be 85.5%. 1.91 mg was recovered from the glass tube walls after vaporization, for a percent yield of 95.5%.

Diltiazam was also coated on a piece of aluminum foil (20 cm$^2$) according to Method C. The calculated thickness of the drug film was 1.1 µm. The substrate was heated as described in Method C at 90 V for 3.5 seconds under an argon atmosphere. The purity of the drug-aerosol particles was determined to be 97.1%. 1.08 mg was recovered from the glass tube walls after vaporization, for a percent yield of 49.1%.

Example 41

Diphenhydramine (MW 255, melting point <25° C., oral dose 25 mg), an antihistamine, was coated on an aluminum foil substrate (20 cm$^2$) according to Method C. 5.50 mg of drug was applied to the substrate, for a calculated thickness of the drug film of 2.8 µm. The substrate was heated as described in Method C at 108 V for 2.25 seconds. The purity of the drug-aerosol particles was determined to be 93.8%. 3.97 mg was recovered from the glass tube walls after vaporization, for a percent yield of 72.2%.

The hydrochloride salt was also tested. 4.90 mg of drug was coated onto an aluminum substrate, for a calculated thickness of the drug film of 2.5 µm. The substrate was heated under an argon atmosphere as described in Method C at 60 V for 10 seconds. The purity of the drug-aerosol particles was determined to be 90.3%. 3.70 mg was recovered from the glass tube walls after vaporization, for a percent yield of 75.5%. Another experiment with the hydrochloride salt was done under an argon atmosphere. 5.20 mg of drug was coated onto an aluminum substrate, for a calculated thickness of the drug film of 2.6 µm. The substrate was heated as described in Method C at 60 V for 10 seconds. The purity of the drug-aerosol particles was determined to be 93.3%. 3.90 mg was recovered from the glass tube walls after vaporization, for a percent yield of 75.0%.

Example 42

Disopyramide (MW 339, melting point 95° C., oral dose 100 mg), a cardiovascular agent, was coated on a stainless steel cylinder (8 cm$^2$) according to Method D. 1.07 mg of drug was applied to the substrate, for a calculated drug film thickness of 1.3 µm. The substrate was heated as described in Method D by charging the capacitors to 20.5 V. The purity of the drug-aerosol particles was determined to be 99%. 0.63 mg was recovered from the filter after vaporization, for a percent yield of 58.9%. A total mass of 0.9 mg was recovered from the test apparatus and substrate, for a total recovery of 84.1%.

High speed photographs were taken as the drug-coated substrate was heated to monitor visually formation of a thermal vapor. The photographs, shown in FIGS. 25A-25D, showed that a thermal vapor was initially visible 50 milliseconds after heating was initiated, with the majority of the thermal vapor formed by 100 milliseconds. Generation of the thermal vapor was complete by 200 milliseconds.

Example 43

Doxepin (MW 279, melting point <25° C. oral dose 75 mg), a psychotherapeutic agent, was coated on an aluminum foil substrate (20 cm$^2$) according to Method C. 2.0 mg of drug was applied to the substrate, for a calculated thickness of the drug film of 1.0 µm. The substrate was heated as described in Method C at 90 V for 3.5 seconds. The purity of the drug-aerosol particles was determined to be 99%. The total mass recovered from the glass tube walls after vaporization ~100%.

Another substrate containing doxepin was also prepared. On an aluminum foil substrate (20 cm$^2$) 8.6 mg of drug was applied to the substrate, for a calculated thickness of the drug film of 4.5 µm. The substrate was heated as described in Method C at 90 V for 5 seconds. The purity of the drug-aerosol particles was determined to be 81.1%. 6.4 mg was recovered from the glass tube walls after vaporization, for a percent yield of 74.4%.

Another substrate containing doxepin was also prepared for testing under argon. On an aluminum foil substrate (20 cm$^2$) 1.8 mg of drug was applied to the substrate, for a calculated thickness of the drug film of 0.9 µm. The substrate was heated as described in Method C at 90 V for 3.5 seconds. The purity of the drug-aerosol particles was determined to be 99.1%. The total mass recovered from the glass tube walls after vaporization ~100%.

Example 44

Donepezil (MW 379, oral dose 5 mg), a drug used in management of Alzheimer's, was coated on a stainless steel cylinder (8 cm$^2$) according to Method D. 5.73 mg of drug was applied to the substrate, for a calculated drug film thickness of 6.9 µm. The substrate was heated as described in Method D by charging the capacitors to 20.5 V. The purity of the drug-aerosol particles was determined to be 96.9%. 3 mg was recovered from the filter after vaporization, for a percent yield of 52.4%. A total mass of 3 mg was recovered from the test apparatus and substrate, for a total recovery of 52.4%.

Donepezil was also tested according to Method B, by coating a solution of the drug onto a piece of stainless steel foil (5 cm$^2$). Six substrates were prepared, with film thicknesses ranging from about 0.5 µm to about 3.2 µm. The substrates were heated as described in Method B by charging the capacitors to 14.5 or 15.5 V. Purity of the drug aerosol particles from each substrate was determined. The results are shown in FIG. 7.

Donepezil was also tested by coating a solution of the drug onto a piece of stainless steel foil (5 cm$^2$). The substrate having a drug film thickness of 2.8 µm was prepared by depositing 1.51 mg of drug. After volatilization of drug from the substrate by charging the capacitors to 14.5 V. 1.37 mg of aerosol particles were recovered from the filter, for a percent yield of 90.9%. The purity of drug compound recovered from the filter was 96.5%. A total mass of 1.51 mg was recovered from the test apparatus and substrate, for a total recovery of 100%.

Example 45

Eletriptan (MW 383, oral dose 3 mg), a serotonin 5-HT receptor agonist used as a migraine preparation, was coated on a piece of stainless steel foil (6 cm$^2$) according to Method B. 1.38 mg of drug was applied to the substrate, for a calculated drug film thickness of 2.2 µm. The substrate was heated as described in Method B by charging the capacitors to 16 V. The purity of the drug-aerosol particles was determined to be 97.8%. 1.28 mg was recovered from the filter after vaporization, for a percent yield of 93%. The total mass was recovered from the test apparatus and substrate, for a total recovery of 100%.

Example 46

Estradiol (MW 272, melting point 179° C., oral dose 2 mg), a hormonal agent, was coated on a piece of aluminum foil (20 cm²) according to Method C. The calculated thickness of the drug film was 1.3 µm. The substrate was heated as described in Method C at 60 V for 9 seconds. The purity of the drug-aerosol particles was determined to be 98.5%. 1.13 mg was recovered from the glass tube walls after vaporization, for a percent yield of 45.2%.

Another substrate containing estradiol was also prepared for testing under argon. On an aluminum foil substrate (20 cm²) 2.6 mg of drug was applied to the substrate, for a calculated thickness of the drug film of 1.3 µm. The substrate was heated as described in Method C at 60 V for 9 seconds. The purity of the drug-aerosol particles was determined to be 98.7%. 1.68 mg was recovered from the glass tube walls after vaporization, for a percent yield of 64.6%.

Example 47

Estradiol-3,17-diacetate (MW 357, oral dose 2 mg), a hormonal prodrug, was coated on a piece of aluminum foil (20 cm²) according to Method C. The calculated thickness of the drug film was 0.9 µm. The substrate was heated as described in Method C at 60 V for 7 seconds. The purity of the drug-aerosol particles was determined to be 96.9%. 1.07 mg was recovered from the glass tube walls after vaporization, for a percent yield of 62.9%.

Example 48

Efavirenz (MW 316, melting point 141° C., oral dose 600 mg), an anti-infective agent, was coated on a stainless steel cylinder (8 cm²) according to Method D. 0.82 mg of drug was applied to the substrate, for a calculated drug film thickness of 1 µm. The substrate was heated as described in Method D by charging the capacitors to 20.5 V. The purity of the drug-aerosol particles was determined to be 97.9%. 0.52 mg was recovered from the filter after vaporization, for a percent yield of 63.4%. A total mass of 0.6 mg was recovered from the test apparatus and substrate, for a total recovery of 73.2%.

Example 49

Ephedrine (MW 165, melting point 40° C., oral dose 10 mg), a respiratory agent, was coated on an aluminum foil substrate (20 cm²) according to Method C. 8.0 mg of drug was applied to the substrate, for a calculated thickness of the drug film of 4.0 µm. The substrate was heated as described in Method C at 90 V for 5 seconds. The purity of the drug-aerosol particles was determined to be 99%. 7.26 mg was recovered from the glass tube walls after vaporization, for a percent yield of 90.8%.

Example 50

Esmolol (MW 295, melting point 50° C., oral dose 35 mg), a cardiovascular agent, was coated on a piece of aluminum foil (20 cm²) according to Method C. The calculated thickness of the drug film was 4.9 µm. The substrate was heated as described in Method C at 90 V for 5 seconds. The purity of the drug-aerosol particles was determined to be 95.8%. 6.4 mg was recovered from the glass tube walls after vaporization, for a percent yield of 65.3%.

Esmolol was coated on a stainless steel cylinder (8 cm²) according to Method D. 0.83 mg of drug was applied to the substrate, for a calculated drug film thickness of 1.4 µm. The substrate was heated as described in Method D by charging the capacitors to 20.5 V. The purity of the drug-aerosol particles was determined to be 93%. 0.63 mg was recovered from the filter after vaporization, for a percent yield of 75.9%. A total mass of 0.81 mg was recovered from the test apparatus and substrate, for a total recovery of 97.6%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 60 milliseconds. Generation of the thermal vapor was complete by 75 milliseconds.

Example 51

Estazolam (MW 295, melting point 229° C., oral dose 2 mg), a sedative and hypnotic, was coated on an aluminum foil substrate (20 cm²) according to Method C. 2.0 mg of drug was applied to the substrate, for a calculated thickness of the drug film of 1.0 µm. The substrate was heated basically as described in Method C at 60 V for 3 seconds then 45 V for 11 seconds. The purity of the drug-aerosol particles was determined to be 99.9%. 1.4 mg was recovered from the glass tube walls after vaporization, for a percent yield of 70%.

Example 52

Ethacrynic acid (MW 303, melting point 122° C., oral dose 25.0 mg), a cardiovascular agent, was coated on a stainless steel cylinder (8 cm²) according to Method E. 1.10 mg of drug was applied to the substrate, for a calculated drug film thickness of 1.3 µm. The substrate was heated as described in Method E and purity of the drug-aerosol particles was determined to be 99.8%. 0.85 mg was recovered from the filter after vaporization, for a percent yield of 77.3%. A total mass of 1.1 mg was recovered from the test apparatus and substrate, for a total recovery of 100%.

Example 53

Ethambutol (MW 204, melting point 89° C., oral dose 1000 mg), a anti-infective agent, was coated on a stainless steel cylinder (8 cm²) according to Method D. 0.85 mg of drug was applied to the substrate, for a calculated drug film thickness of 1 µm. The substrate was heated as described in Method D by charging the capacitors to 20.5 V. The purity of the drug-aerosol particles was determined to be 90%. 0.50 mg was recovered from the filter after vaporization, for a percent yield of 58.8%. A total mass of 0.85 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 50 milliseconds. Generation of the thermal vapor was complete by 90 milliseconds.

Example 54

Fluticasone propionate (MW 501, melting point 272° C., oral dose 0.04 mg), a respiratory agent, was coated on a piece of stainless steel foil (5 cm$^2$) according to Method B. The calculated thickness of the drug film was 0.6 μm. The substrate was heated as described in Method B by charging the capacitors to 15.5 V. The purity of the drug-aerosol particles was determined to be 91.6%. 0.211 mg was recovered from the filter after vaporization, for a percent yield of 70.1%. A total mass of 0.215 mg was recovered from the test apparatus and substrate, for a total recovery of 71.4%.

Example 55

Fenfluramine (MW 231, melting point 112° C., oral dose 20 mg), an obesity management, was coated on a piece of aluminum foil (20 $cm^2$) according to Method C. 9.2 mg were coated. The calculated thickness of the drug film was 4.6 μm. The substrate was heated as described in Method C at 90 V for 5 seconds. The purity of the drug-aerosol particles was determined to be >99.5%. The total mass was recovered from the glass tube walls after vaporization, for a percent yield of ~100%.

Example 56

Fenoprofen (MW 242, melting point <25° C., oral dose 200 mg), an analgesic, was coated on a piece of aluminum foil (20 $cm^2$) according to Method C. The calculated thickness of the drug film was 3.7 μm. The substrate was heated as described in Method C at 60 V for 5 seconds. The purity of the drug-aerosol particles was determined to be 98.7%. 4.98 mg was recovered from the glass tube walls after vaporization, for a percent yield of 67.3%.

Example 57

Fentanyl (MW 336, melting point 84° C., oral dose 0.2 mg), an analgesic, was coated onto ten stainless steel foil substrates (5 $cm^2$) according to Method B. The calculated thickness of the drug film on each substrate ranged from about 0.2 μm to about 3.3 μm. The substrates were heated as described in Method B by charging the capacitors to 14 V. Purity of the drug-aerosol particles from each substrate was determined and the results are shown in FIG. 20.

Fentanyl was also coated on a stainless steel cylinder (8 $cm^2$) according to Method D. 0.29 mg of drug was applied to the substrate, for a calculated drug film thickness of 0.4 μm. The substrate was heated as described in Method D by charging the capacitors to 18 V. The purity of the drug-aerosol particles was determined to be 97.9%. 0.19 mg was recovered from the filter after vaporization, for a percent yield of 64%. A total mass of 0.26 mg was recovered from the test apparatus and substrate, for a total recovery of 89%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 100 milliseconds. Generation of the thermal vapor was complete by 250 milliseconds.

Example 58

Flecainide (MW 414, oral dose 50 mg), a cardiovascular agent, was coated on a stainless steel cylinder (8 $cm^2$) according to Method D. 0.80 mg of drug was applied to the substrate, for a calculated drug film thickness of 1 μm. The substrate was heated as described in Method D by charging the capacitors to 20.5 V. The purity of the drug-aerosol particles was determined to be 99.6%. 0.54 mg was recovered from the filter after vaporization, for a percent yield of 67.5%. A total mass of 0.7 mg was recovered from the test apparatus and substrate, for a total recovery of 90%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 65 milliseconds. Generation of the thermal vapor was complete by 110 milliseconds.

Example 59

Fluconazole (MW 306, melting point 140° C., oral dose 200 mg), an anti-infective agent, was coated on a piece of stainless steel foil (5 $cm^2$) according to Method B. 0.737 mg of drug was applied to the substrate, for a calculated drug film thickness of 1.4 μm. The substrate was heated as described in Method B by charging the capacitors to 15.5 V. The purity of the drug-aerosol particles was determined to be 94.3%. 0.736 mg was recovered from the filter after vaporization, for a percent yield of 99.9%. A total mass of 0.737 mg was recovered from the test apparatus and substrate, for a total recovery of 100%.

Example 60

Flunisolide (MW 435, oral dose 0.25 mg), a respiratory agent, was coated was coated on a stainless steel cylinder (8 $cm^2$) according to Method E. 0.49 mg of drug was applied to the substrate, for a calculated drug film thickness of 0.6 μm. The substrate was heated as described in Method E and purity of the drug-aerosol particles was determined to be 97.6%. 0.3 mg was recovered from the filter after vaporization, for a percent yield of 61.2%. A total mass of 0.49 mg was recovered from the test apparatus and substrate, for a total recovery of 100%.

Another substrate (stainless steel foil, 5 $cm^2$) was prepared by applying 0.302 mg drug to form a film having a thickness of 0.6 μm. The substrate was heated as described in Method B by charging the capacitor to 15.0 V. The purity of the drug-aerosol particles was determined to be 94.9%. 0.296 mg was recovered from the filter after vaporization, for a percent yield of 98%. A total mass of 0.302 mg was recovered from the test apparatus and substrate, for a total recovery of 100%.

Example 61

Flunitrazepam (MW 313, melting point 167° C., oral dose 0.5 mg), a sedative and hypnotic, was coated on a piece of aluminum foil (24.5 $cm^2$) according to Method G. The calculated thickness of the drug film was 0.6 μm. The substrate was heated as described in Method G at 90 V for 6 seconds. The purity of the drug-aerosol particles was determined to be 99.8%. 0.73 mg was recovered from the glass tube walls after vaporization, for a percent yield of 60.8%.

Flunitrazepam was further coated on an aluminum foil substrate (24 $cm^2$) according to Method C. 5 mg of the drug was applied to the substrate, for a calculated thickness of the drug film of 2.08 μm. The substrate was heated substantially as described in Method C at 60 V for 7 seconds. The purity of the drug-aerosol particles was determined to be at least 99.9%.

Example 62

Fluoxetine (MW 309, oral dose 20 mg), a psychotherapeutic agent, was coated on an aluminum foil substrate (20 cm$^2$) according to Method C. 1.90 mg of drug was applied to the substrate, for a calculated thickness of the drug film of 1.0 µm. The substrate was heated as described in Method C at 90 V for 3.5 seconds. The purity of the drug-aerosol particles was determined to be 97.4%. 1.4 mg was recovered from the glass tube walls after vaporization, for a percent yield of 73.7%.

Another substrate containing fluoxetine coated (2.0 mg drug) to a film thickness of 1.0 µm was prepared by the same method and heated under an argon atmosphere at 90 V for 3.5 seconds. The purity of the drug-aerosol particles was determined to be 96.8%. 1.7 mg was recovered from the glass tube walls after vaporization, for a percent yield of 85.0%.

Example 63

Galanthamine (MW 287, oral dose 4 mg) was coated on a stainless steel cylinder (8 cm$^2$) according to Method D. 1.4 mg of drug was applied to the substrate, for a calculated drug film thickness of 1.7 µm. The substrate was heated as described in Method D by charging the capacitors to 20.5 V. The purity of the drug-aerosol particles was determined to be >99.5%. 1.16 mg was recovered from the filter after vaporization, for a percent yield of 82.6%. A total mass of 1.39 mg was recovered from the test apparatus and substrate, for a total recovery of 99.1%.

Example 64

Granisetron (MW 312, oral dose 1 mg), a gastrointestinal agent, was coated on an aluminum foil substrate (20 cm$^2$) according to Method C. 1.50 mg of drug was applied to the substrate, for a calculated thickness of the drug film of 0.8 µm. The substrate was heated as described in Method C at 30 V for 45 seconds. The purity of the drug-aerosol particles was determined to be 99%. 1.3 mg was recovered from the glass tube walls after vaporization, for a percent yield of 86.7%.

mg of granisetron was also coated on an aluminum foil substrate (24.5 cm$^2$) to a calculated drug film thickness of 0.45 µm. The substrate was heated substantially as described in Method G at 90 V for 6 seconds. The purity of the drug-aerosol particles was determined to be 93%. 0.4 mg was recovered from the glass tube walls, for a percent yield of 36%.

Example 65

Haloperidol (MW 376, melting point 149° C., oral dose 2 mg), a psychotherapeutic agent, was coated on an aluminum foil substrate (20 cm$^2$) according to Method C. 2.20 mg of drug was applied to the substrate, for a calculated thickness of the drug film of 1.1 µm. The substrate was heated as described in Method C at 108 V for 2.25 seconds. The purity of the drug-aerosol particles was determined to be 99.8%. 0.6 mg was recovered from the glass tube walls after vaporization, for a percent yield of 27.3%.

Haloperidol was further coated on an aluminum foil substrate according to Method C. The substrate was heated as described in Method C. When 2.1 mg of the drug was heated at 90 V for 3.5 seconds, the purity of the resultant drug-aerosol particles was determined to be 96%. 1.69 mg of aerosol particles were collected for a percent yield of the aerosol of 60%. When 2.1 mg of drug was used and the system was flushed with argon prior to volatilization, the purity of the drug-aerosol particles was determined to be 97%. The percent yield of the aerosol was 29%.

Example 66

Hydromorphone (MW 285, melting point 267° C., oral dose 2 mg), an analgesic, was coated on a stainless steel cylinder (9 cm$^2$) according to Method D. 5.62 mg of drug was applied to the substrate, for a calculated drug film thickness of 6.4 µm. The substrate was heated as described in Method D by charging the capacitors to 19 V. The purity of the drug-aerosol particles was determined to be 99.4%. 2.34 mg was recovered from the filter after vaporization, for a percent yield of 41.6%. A total mass of 5.186 mg was recovered from the test apparatus and substrate, for a total recovery of 92.3%.

Hydromorphone was also coated on a piece of aluminum foil (20 cm$^2$) according to Method C. The calculated thickness of the drug film was 1.1 µm. The substrate was heated as described in Method C at 90 V for 3.5 seconds. The purity of the drug-aerosol particles was determined to be 98.3%. 0.85 mg was recovered from the glass tube walls after vaporization, for a percent yield of 40.5%.

Figure 8:
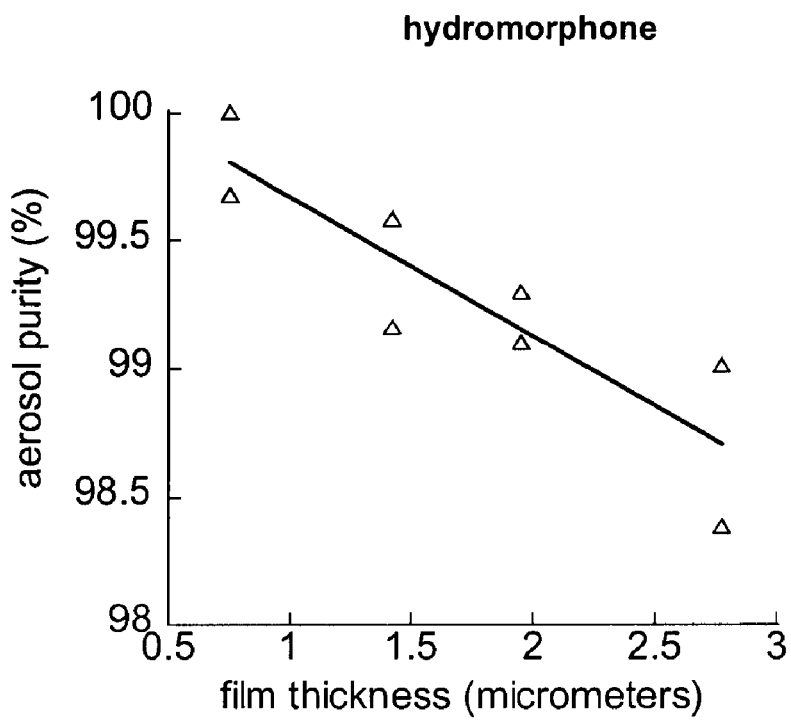
FIG. 8 is plot showing purity of thermal vapor as a function of drug film thickness, in micrometers, for hydromorphone free base.
Figure 9:
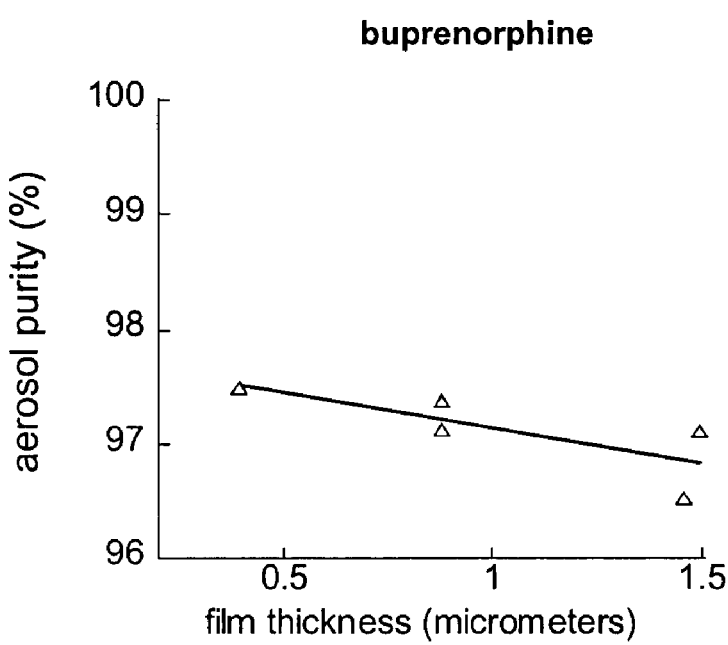
FIG. 9 is plot showing purity of thermal vapor as a function of drug film thickness, in micrometers, for buprenorphine free base.
Figure 10:
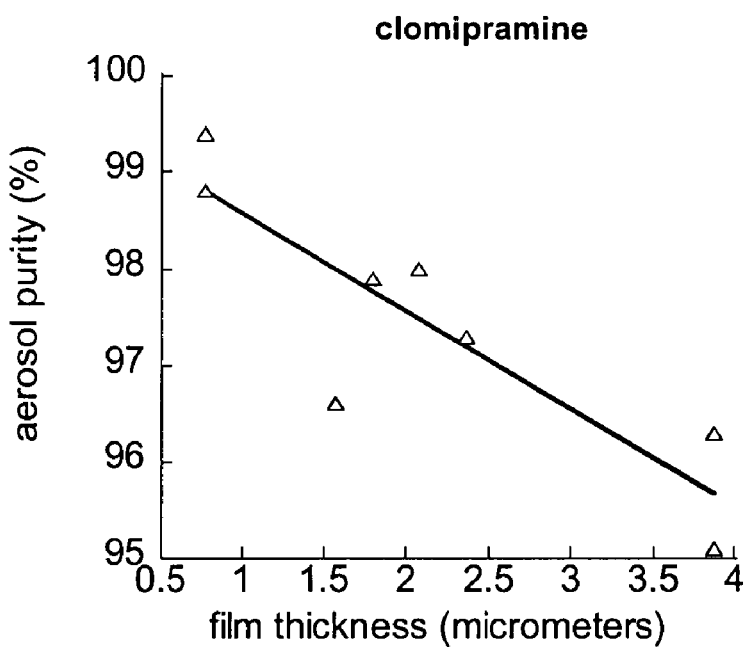
FIG. 10 is plot showing purity of thermal vapor as a function of drug film thickness, in micrometers, for clomipramine free base.
Figure 11:
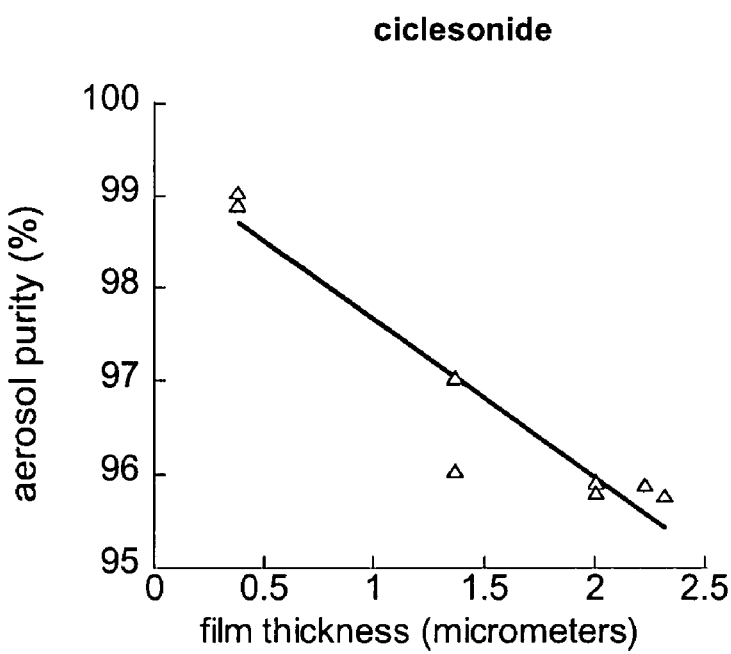
FIG. 11 is plot showing purity of thermal vapor as a function of drug film thickness, in micrometers, for ciclesonide.
Figure 12:
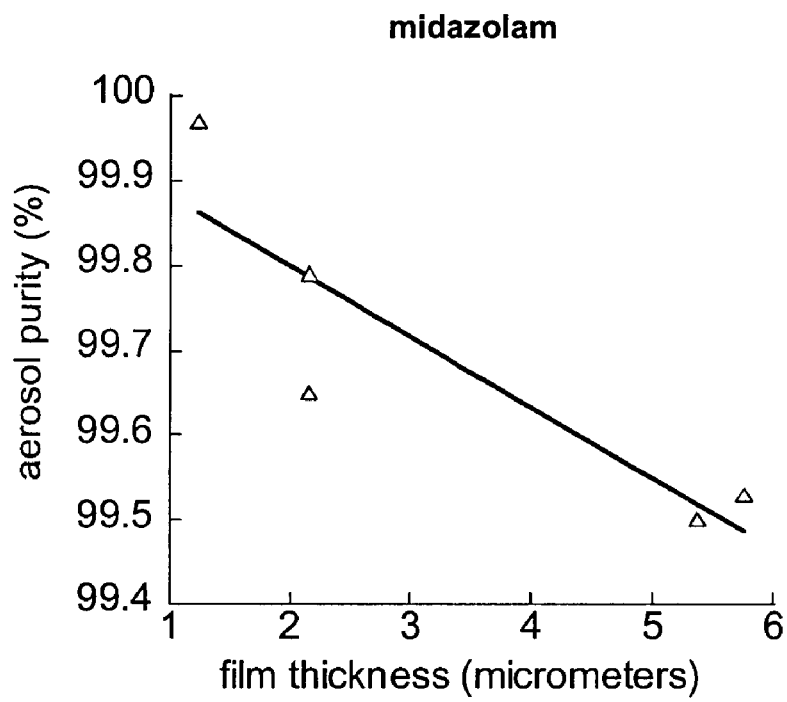
FIG. 12 is plot showing purity of thermal vapor as a function of drug film thickness, in micrometers, for midazolam free base.

Hydromorphone was also coated onto eight stainless steel cylinder substrates (8 cm$^2$) according to Method D. The calculated thickness of the drug film on each substrate ranged from about 0.7 µm to about 2.8 µm. The substrates were heated as described in Method D by charging the capacitors to 20.5 V. The purity of the drug-aerosol particles determined. The results are shown in FIG. 8. For the substrate having a drug film thickness of 1.4 µm, 1.22 mg of drug was applied to the substrate. After vaporization of this substrate, 0.77 mg was recovered from the filter, for a percent yield of 63.21%. The purity of the drug-aerosol particles was determined to be 99.6%. A total mass of 1.05 mg was recovered from the test apparatus and substrate, for a total recovery of 86.1%.

Example 67

Hydroxychloroquine (MW 336, melting point 91° C., oral dose 400 mg), an antirheumatic agent, was coated on a stainless steel cylinder (8 cm$^2$) according to Method D. 6.58 mg of drug was applied to the substrate, for a calculated drug film thickness of 11 µm. The substrate was heated as described in Method D by charging the capacitors to 20.5 V. The purity of the drug-aerosol particles was determined to be 98.9%. 3.48 mg was recovered from the filter after vaporization, for a percent yield of 52.9%. A total mass of 5.1 mg was recovered from the test apparatus and substrate, for a total recovery of 77.8%.

Example 68

Hyoscyamine (MW 289, melting point 109° C., oral dose 0.38 mg), a gastrointestinal agent, was coated on a piece of aluminum foil (20 cm$^2$) according to Method C. The calculated thickness of the drug film was 0.9 µm. The substrate was heated as described in Method C at 60 V for 8 seconds. The purity of the drug-aerosol particles was determined to be 95.9%. 0.86 mg was recovered from the glass tube walls after vaporization, for a percent yield of 50.6%.

Example 69

Ibuprofen (MW 206, melting point 77° C., oral dose 200 mg), an analgesic, was coated on an aluminum foil substrate (20 cm$^2$) according to Method C. 10.20 mg of drug was applied to the substrate, for a calculated thickness of the drug film of 5.1 μm. The substrate was heated as described in Method C at 60 V for 5 seconds. The purity of the drug-aerosol particles was determined to be 99.7%. 5.45 mg was recovered from the glass tube walls after vaporization, for a percent yield of 53.4%.

Example 70

Imipramine (MW 280, melting point <25° C., oral dose 50 mg), a psycho therapeutic agent, was coated on a piece of aluminum foil (20 cm$^2$) according to Method C. 1.8 mg was coated on the aluminum foil. The calculated thickness of the drug film was 0.9 μm. The substrate was heated as described in Method C at 90 V for 3.5 seconds. The purity of the drug-aerosol particles was determined to be 98.3%. The total mass recovered from the glass tube walls after vaporization was ~100%.

Another substrate containing imipramine coated to a film thickness of 0.9 μm was prepared by the same method and heated under an argon atmosphere at 90 V for 3.5 seconds. The purity of the drug-aerosol particles was determined to be 99.1%. 1.5 mg was recovered from the glass tube walls after vaporization, for a percent yield of 83.3%.

Example 71

Indomethacin (MW 358, melting point 155° C., oral dose 25 mg), an analgesic, was coated on a piece of aluminum foil (20 cm$^2$) according to Method C. The calculated thickness of the drug film was 1.2 μm. The substrate was heated as described in Method C at 60 V for 6 seconds. The purity of the drug-aerosol particles was determined to be 96.8%. 1.39 mg was recovered from the glass tube walls after vaporization, for a percent yield of 60.4%.

Another substrate containing indomethacin coated to a film thickness of 1.5 μm was prepared by the same method and heated under an argon atmosphere at 60 V for 6 seconds. The purity of the drug-aerosol particles was determined to be 99%. 0.61 mg was recovered from the glass tube walls after vaporization, for a percent yield of 20.3%.

Example 72

Indomethacin ethyl ester (MW 386, oral dose 25 mg), an analgesic, was coated on a piece of aluminum foil (20 cm$^2$) according to Method C. The calculated thickness of the drug film was 2.6 μm. The substrate was heated as described in Method C at 60 V for 9 seconds. The purity of the drug-aerosol particles was determined to be 99%. 2.23 mg was recovered from the glass tube walls after vaporization, for a percent yield of 42.9%.

Another substrate containing indomethacin ethyl ester coated to a film thickness of 2.6 μm was prepared by the same method and heated under an argon atmosphere at 60 V for 9 seconds. The purity of the drug-aerosol particles was determined to be 99%. 3.09 mg was recovered from the glass tube walls after vaporization, for a percent yield of 59.4%.

Example 73

Indomethacin methyl ester (MW 372, oral dose 25 mg), an analgesic, was coated on a piece of aluminum foil (20 cm$^2$) according to Method C. The calculated thickness of the drug film was 2.1 μm. The substrate was heated as described in Method C at 60 V for 6 seconds. The purity of the drug-aerosol particles was determined to be 99%. 1.14 mg was recovered from the glass tube walls after vaporization, for a percent yield of 27.1%.

Another substrate containing indomethacin methyl ester coated to a film thickness of 1.2 μm was prepared by the same method and heated under an argon atmosphere at 60 V for 6 seconds. The purity of the drug-aerosol particles was determined to be 99%. 1.44 mg was recovered from the glass tube walls after vaporization, for a percent yield of 60%.

Example 74

Isocarboxazid (MW 231, melting point 106° C., oral dose 10 mg), a psychotherapeutic agent, was coated on a stainless steel cylinder (8 cm$^2$) according to Method D. 0.97 mg of drug was applied to the substrate, for a calculated drug film thickness of 1.2 μm. The substrate was heated as described in Method D by charging the capacitors to 20.5 V. The purity of the drug-aerosol particles was determined to be 99.6%. 0.52 mg was recovered from the filter after vaporization, for a percent yield of 53%. A total mass of 0.85 mg was recovered from the test apparatus and substrate, for a total recovery of 87.7%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 70 milliseconds. Generation of the thermal vapor was complete by 200 milliseconds.

Example 75

Isotretinoin (MW 300, melting point 175° C., oral dose 35 mg), a skin and mucous membrane agent, was coated on a stainless steel cylinder (8 cm$^2$) according to Method D. 1.11 mg of drug was applied to the substrate, for a calculated drug film thickness of 1.4 μm. The substrate was heated as described in Method D by charging the capacitors to 20.5 V. The purity of the drug-aerosol particles was determined to be 96.6%. 0.66 mg was recovered from the filter after vaporization, for a percent yield of 59.5%. A total mass of 0.86 mg was recovered from the test apparatus and substrate, for a total recovery of 77.5%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 65 milliseconds. Generation of the thermal vapor was complete by 110 milliseconds.

Example 76

Ketamine (MW 238, melting point 93° C., IV dose 100 mg), an anesthetic, was coated on a stainless steel cylinder (8 cm$^2$) according to Method D. 0.836 mg of drug was applied to the substrate, for a calculated drug film thickness of 1.0 μm. The substrate was heated as described in Method D by charging the capacitors to 20.5 V. The purity of the drug-aerosol particles was determined to be 99.9%. 0.457 mg was recovered from the filter after vaporization, for a percent yield of 54.7%. A total mass of 0.712 mg was recovered from the test apparatus and substrate, for a total recovery of 85.2%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 75 milliseconds. Generation of the thermal vapor was complete by 100 milliseconds.

Example 77

Ketoprofen (MW 254, melting point 94° C., oral dose 25 mg), an analgesic, was coated on an aluminum foil substrate (20 cm$^2$) according to Method C. 10.20 mg of drug was applied to the substrate, for a calculated thickness of the drug film of 5.1 µm. The substrate was heated as described in Method C at 60 V for 16 seconds. The purity of the drug-aerosol particles was determined to be 98%. 7.24 mg was recovered from the glass tube walls after vaporization, for a percent yield of 71%.

Example 78

Ketoprofen ethyl ester (MW 282, oral dose 25 mg), an analgesic, was coated on a piece of aluminum foil (20 cm$^2$) according to Method C. The calculated thickness of the drug film was 2.0 µm. The substrate was heated as described in Method C at 60 V for 8 seconds. The purity of the drug-aerosol particles was determined to be 99%. 3.52 mg was recovered from the glass tube walls after vaporization, for a percent yield of 88%.

Another substrate containing ketroprofen ethyl ester coated to a film thickness of 2.7 µm was prepared by the same method and heated under an argon atmosphere at 60 V for 8 seconds. The purity of the drug-aerosol particles was determined to be 99.6%. 4.1 mg was recovered from the glass tube walls after vaporization, for a percent yield of 77.4%.

Example 79

Ketoprofen Methyl Ester (MW 268, oral dose 25 mg), an analgesic, was coated on a piece of aluminum foil (20 cm$^2$) according to Method C. The calculated thickness of the drug film was 2.0 µm. The substrate was heated as described in Method C at 60 V for 8 seconds purity of the drug-aerosol particles was determined to be 99%. 2.25 mg was recovered from the glass tube walls after vaporization, for a percent yield of 56.3%.

Another substrate containing ketoprofen methyl ester coated to a film thickness of 3.0 µm was prepared by the same method and heated under an argon atmosphere at 60 V for 8 seconds. The purity of the drug-aerosol particles was determined to be 99%. 4.4 mg was recovered from the glass tube walls after vaporization, for a percent yield of 73.3%.

Example 80

Ketorolac ethyl ester (MW 283, oral dose 10 mg), an analgesic, was coated on an aluminum foil substrate (20 cm$^2$) according to Method C. 9.20 mg of drug was applied to the substrate, for a calculated thickness of the drug film of 4.6 µm. The substrate was heated as described in Method C at 60 V for 12 seconds. The purity of the drug-aerosol particles was determined to be 99%. 5.19 mg was recovered from the glass tube walls after vaporization, for a percent yield of 56.4%.

Example 81

Ketorolac methyl ester (MW 269, oral dose 10 mg) was also coated on an aluminum foil substrate (20 cm$^2$) to a drug film thickness of 2.4 µm (4.8 mg drug applied). The substrate was heated as described in Method C at 60 V for 6 seconds. The purity of the drug-aerosol particles was determined to be 98.8%. 3.17 mg was recovered from the glass tube walls after vaporization, for a percent yield of 66.0%.

Example 82

Ketotifen (MW 309, melting point 152° C., used as 0.025% solution in the eye) was coated on a stainless steel cylinder (8 cm$^2$) according to Method D. 0.544 mg of drug was applied to the substrate, for a calculated drug film thickness of 0.7 µm. The substrate was heated as described in Method D by charging the capacitors to 20.5 V. The purity of the drug-aerosol particles was determined to be 99.9%. 0.435 mg was recovered from the filter after vaporization, for a percent yield of 80%. A total mass of 0.544 mg was recovered from the test apparatus and substrate, for a total recovery of 100%.

Example 83

Lamotrigine (MW 256, melting point 218° C., oral dose 150 mg), an anticonvulsant, was coated on a stainless steel cylinder (8 cm$^2$) according to Method D. 0.93 mg of drug was applied to the substrate, for a calculated drug film thickness of 1.1 µm. The substrate was heated as described in Method D by charging the capacitors to 20.5 V. The purity of the drug-aerosol particles was determined to be 99.1%. 0.58 mg was recovered from the filter after vaporization, for a percent yield of 62.4%. A total mass of 0.93 mg was recovered from the test apparatus and substrate, for a total recovery of 100%.

Example 84

Lidocaine (MW 234, melting point 69° C., oral dose 30 mg), an anesthetic, was coated on an aluminum foil substrate (20 cm$^2$) according to Method C. 9.50 mg of drug was applied to the substrate, for a calculated thickness of the drug film of 4.8 µm. The substrate was heated as described in Method C at 90 V for 5 seconds. The purity of the drug-aerosol particles was determined to be 99.8%. 7.3 mg was recovered from the glass tube walls after vaporization, for a percent yield of 76.8%.

Lidocaine was further coated on an aluminum foil substrate (24.5 cm$^2$) according to Method G. 10.4 mg of the drug was applied to the substrate, for a calculated thickness of the drug film of 4.24 µm. The substrate was heated as described in Method G at 90 V for 6 seconds. The purity of the drug-aerosol particles was determined to be >99%. 10.2 mg of the drug was found to have aerosolized, for a percent yield of 98%.

Example 85

Linezolid (MW 337, melting point 183° C., oral dose 600 mg), an anti-infective agent, was coated on a stainless steel cylinder (8 cm$^2$) according to Method D. 1.09 mg of drug was applied to the substrate, for a calculated drug film thickness of 1.3 µm. The substrate was heated as described in Method D by charging the capacitors to 20.5 V. The purity of the drug-aerosol particles was determined to be 95%. 0.70 mg was recovered from the filter after vaporization, for a percent yield of 64.2%. A total mass of 1.09 mg was recovered from the test apparatus and substrate, for a total recovery of 100%.

Example 86

Loperamide (MW 477, oral dose 4 mg), a gastrointestinal agent, was coated on a stainless steel cylinder (9 cm$^2$) according to Method D. 1.57 mg of drug was applied to the substrate, for a calculated drug film thickness of 1.8 μm. The substrate was heated as described in Method D by charging the capacitors to 20.5 V. The purity of the drug-aerosol particles was determined to be 99.4%. 0.871 mg was recovered from the filter after vaporization, for a percent yield of 55.5%. A total mass of 1.57 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 80 milliseconds. Generation of the thermal vapor was complete by 165 milliseconds.

Example 87

Loratadine (MW 383, melting point 136° C., oral dose 10 mg), an antihistamine, was coated on an aluminum foil substrate (20 cm$^2$) according to Method C. 5.80 mg of drug was applied to the substrate, for a calculated thickness of the drug film of 2.9 μm. The substrate was heated as described in Method C at 60 V for 9 seconds. The purity of the drug-aerosol particles was determined to be 99%. 3.5 mg was recovered from the glass tube walls after vaporization, for a percent yield of 60.3%.

Another substrate containing loratadine coated (6.60 mg drug) to a film thickness of 3.3 μm was prepared by the same method and heated under an argon atmosphere at 60 V for 9 seconds. The purity of the drug-aerosol particles was determined to be 99.6%. 4.5 mg was recovered from the glass tube walls after vaporization, for a percent yield of 68.2%.

Loratadine was further coated on an aluminum foil substrate (24.5 cm$^2$) according to Method G. 10.4 mg of the drug was applied to the substrate, for a calculated thickness of the drug film of 4.24 μm. The substrate was heated substantially as described in Method G at 90 V for 6 seconds, except that two of the openings of the T-shaped tube were left open and the third connected to the 1 L flask. The purity of the drug-aerosol particles was determined to be >99%. 3.8 mg of the drug was found to have aerosolized, for a percent yield of 36.5%.

Example 88

Lovastatin (MW 405, melting point 175° C., oral dose 20 mg), a cardiovascular agent, was coated on a stainless steel cylinder (8 cm$^2$) according to Method D. 0.71 mg of drug was applied to the substrate, for a calculated drug film thickness of 0.9 μm. The substrate was heated as described in Method D by charging the capacitors to 20.5 V. The purity of the drug-aerosol particles was determined to be 94.1%. 0.43 mg was recovered from the filter after vaporization, for a percent yield of 60.6%. A total mass of 0.63 mg was recovered from the test apparatus and substrate, for a total recovery of 88.7%.

Example 89

Lorazepam N,O-diacetyl (typical inhalation dose 0.5 mg), was coated on a piece of aluminum foil (20 cm$^2$) according to Method C. The calculated thickness of the drug film was 0.5 μm. The substrate was heated as described in Method C at 60 V for 7 seconds. The purity of the drug-aerosol particles was determined to be 90%. 0.87 mg was recovered from the glass tube walls after vaporization, for a percent yield of 87%.

Example 90

Loxapine (MW 328, melting point 110° C., oral dose 30 mg), a psychotherapeutic agent, was coated on a stainless steel cylinder (8 cm$^2$) according to Method D. 7.69 mg of drug was applied to the substrate, for a calculated drug film thickness of 9.2 μm. The substrate was heated as described in Method D by charging the capacitors to 20.5 V. The purity of the drug-aerosol particles was determined to be 99.7%. 3.82 mg was recovered from the filter after vaporization, for a percent yield of 50%. A total mass of 6.89 mg was recovered from the test apparatus and substrate, for a total recovery of 89.6%.

Example 91

Maprotiline (MW 277, melting point 94° C., oral dose 25 mg), a psychotherapeutic agent, was coated on an aluminum foil substrate (20 cm$^2$) according to Method C. 2.0 mg of drug was applied to the substrate, for a calculated thickness of the drug film of 1.0 μm. The substrate was heated as described in Method C at 90 V for 3.5 seconds. The purity of the drug-aerosol particles was determined to be 99.7%. 1.3 mg was recovered from the glass tube walls after vaporization, for a percent yield of 65.0%.

Another substrate containing maprotiline coated to a film thickness of 1.0 μm was prepared by the same method and heated under an argon atmosphere at 90 V for 3.5 seconds. The purity of the drug-aerosol particles was determined to be 99.6%. 1.5 mg was recovered from the glass tube walls after vaporization, for a percent yield of 75%.

Example 92

Meclizine (MW 391, melting point <25° C., oral dose 25 mg), a vertigo agent, was coated on an aluminum foil substrate (20 cm$^2$) according to Method C. 5.20 mg of drug was applied to the substrate, for a calculated thickness of the drug film of 2.6 μm. The substrate was heated as described in Method C at 60 V for 7 seconds. The purity of the drug-aerosol particles was determined to be 90.1%. 3.1 mg was recovered from the glass tube walls after vaporization, for a percent yield of 59.6%.

The same drug coated on an identical substrate (aluminum foil (20 cm$^2$)) to a calculated drug film thickness of 12.5 μm was heated under an argon atmosphere as described in Method C at 60 V for 10 seconds. The purity of the drug-aerosol particles was determined to be 97.3%. 4.81 mg was recovered from the glass tube walls after vaporization, for a percent yield of 19.2%.

The dihydrochloride salt form of the drug was also tested. Meclizine dihydrochloride (MW 464, oral dose 25 mg) was coated on a piece of aluminum foil (20 cm$^2$) according to Method C. 19.4 mg of drug was applied to the substrate, for a calculated thickness of the drug film of 9.7 μm. The substrate was heated as described in Method C at 60 V for 6 seconds. The purity of the drug-aerosol particles was determined to be 75.3%. 0.5 mg was recovered from the glass tube walls after vaporization, for a percent yield of 2.6%.

An identical substrate having a calculated drug film thickness of 11.7 μm was heated under an argon atmosphere at 60 V for 6 seconds. Purity of the drug-aerosol particles was determined to be 70.9%. 0.4 mg was recovered from the glass tube walls after vaporization, for a percent yield of 1.7%.

Example 93

Memantine (MW 179, melting point <25° C., oral dose 20 mg), an antiparkinsonian agent, was coated on a stainless steel cylinder (8 cm$^2$) according to Method D. The calculated thickness of the drug film was 1.7 µm. The substrate was heated as described in Method D by charging the capacitors to 20.5 V. The purity of the drug-aerosol particles determined by LC/MS was >99.5%. 0.008 mg was recovered from the glass tube walls after vaporization, for a percent yield of 0.6%. The total mass recovered was 0.06 mg, for a total recovery yield of 4.5%. The amount of drug trapped on the filter was low, most of the aerosol particles escaped into the vacuum line.

Example 94

Meperidine (MW 247, oral dose 50 mg), an analgesic, was coated on an aluminum foil substrate (20 $cm^2$) according to Method C. 1.8 mg of drug was applied to the substrate, for a calculated thickness of the drug film of 0.9 μm. The substrate was heated as described in Method C at 90 V for 3.5 seconds. The purity of the drug-aerosol particles was determined to be 98.8%. 0.95 mg was recovered from the glass tube walls after vaporization, for a percent yield of 52.8%.

Another substrate containing meperidine coated to a film thickness of 1.1 μm was prepared by the same method and heated under an argon atmosphere at 90 V for 3.5 seconds. The purity of the drug-aerosol particles was determined to be 99.9%. 1.02 mg was recovered from the glass tube walls after vaporization, for a percent yield of 48.6%.

Example 95

Metaproterenol (MW 211, melting point 100° C., oral dose 1.3 mg), a respiratory agent, was coated on a stainless steel cylinder (8 $cm^2$) according to Method D. 1.35 mg of drug was applied to the substrate, for a calculated drug film thickness of 1.6 μm. The substrate was heated as described in Method D by charging the capacitors to 20.5 V. The purity of the drug-aerosol particles was determined to be 99.1%. 0.81 mg was recovered from the filter after vaporization, for a percent yield of 60%. A total mass of 1.2 mg was recovered from the test apparatus and substrate, for a total recovery of 88.9%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 150 milliseconds. Generation of the thermal vapor was complete by 300 milliseconds.

Example 96

Methadone (MW 309, melting point 78° C., oral dose 2.5 mg), an analgesic, was coated on an aluminum foil substrate (20 $cm^2$) according to Method C. 1.80 mg of drug was applied to the substrate, for a calculated thickness of the drug film of 0.9 μm. The substrate was heated as described in Method C at 90 V for 3.5 seconds. The purity of the drug-aerosol particles was determined to be 92.3%. 1.53 mg was recovered from the glass tube walls after vaporization, for a percent yield of 85%.

Example 97

Methoxsalen (MW 216, melting point 148° C., oral dose 35 mg), a skin and mucous membrane agent, was coated on a stainless steel cylinder (8 $cm^2$) according to Method D. 1.03 mg of drug was applied to the substrate, for a calculated drug film thickness of 1.2 μm. The substrate was heated as described in Method D by charging the capacitors to 20.5 V. The purity of the drug-aerosol particles was determined to be 99.6%. 0.77 mg was recovered from the filter after vaporization, for a percent yield of 74.8%. A total mass of 1.03 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 80 milliseconds. Generation of the thermal vapor was complete by 135 milliseconds.

Example 98

Metoprolol (MW 267, oral dose 15 mg), a cardiovascular agent, was coated on an aluminum foil substrate (20 $cm^2$) according to Method C. 10.8 mg of drug was applied to the substrate, for a calculated thickness of the drug film of 5.4 μm. The substrate was heated as described in Method C at 90 V for 5 seconds. The purity of the drug-aerosol particles was determined to be 99.2%. 6.7 mg was recovered from the glass tube walls after vaporization, for a percent yield of 62.0%.

Metoprolol was further coated on an aluminum foil substrate (24.5 $cm^2$) according to Method G. 12.7 mg of the drug was applied to the substrate, for a calculated thickness of the drug film of 5.18 μm. The substrate was heated as described in Method G at 90 V for 6 seconds. The purity of the drug-aerosol particles was determined to be >99%. All of the drug was found to have aerosolized, for a percent yield of 100%.

Example 99

Mexiletine HCl (MW 216, melting point 205° C., oral dose 200 mg), a cardiovascular agent, was coated on a stainless steel cylinder (8 $cm^2$) according to Method D. 0.75 mg of drug was applied to the substrate, for a calculated drug film thickness of 0.9 μm. The substrate was heated as described in Method D by charging the capacitors to 20.5 V. The purity of the drug-aerosol particles was determined to be 99.4%. 0.44 mg was recovered from the filter after vaporization, for a percent yield of 58.7%. A total mass of 0.75 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 75 milliseconds. Generation of the thermal vapor was complete by 200 milliseconds.

Example 100

Midazolam (MW 326, melting point 160° C., oral dose 2.5 mg), a sedative and hypnotic, was coated onto five stainless steel cylindrical substrates according to Method E. The calculated thickness of the drug film on each substrate ranged from about 1.1 μm to about 5.8 μm. The substrates were heated as described in Method E and purity of the drug-aerosol particles determined. The results are shown in FIG. 12.

Another substrate (stainless steel cylindrical, 6 cm$^2$) was prepared by depositing 5.37 mg drug to obtain a drug film thickness of 9 μm. After volatilization of drug from this substrate according to Method E, 3.11 mg was recovered from the filter, for a percent yield of 57.9%. A total mass of 5.06 mg was recovered from the test apparatus and substrate, for a total recovery of 94.2%. Purity of the drug aerosol particles was 99.5%. The yield of aerosol particles was 57.9%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 130 milliseconds. Generation of the thermal vapor was complete by 240 milliseconds.

Midazolam was also coated on an aluminum foil substrate (28.8 cm$^2$) according to Method C. 5.0 mg of the drug was applied to the substrate, for a calculated thickness of the drug film of 1.74 μm. The substrate was heated substantially as described in Method C at 60 V for 6 seconds. The purity of the drug-aerosol particles was determined to be 99.9%.

Another aluminum foil substrate (36 cm$^2$) was prepared essentially according to Method G. 16.7 mg of midazolam was applied to the substrate, for a calculated thickness of the drug film of 4.64 μm. The substrate was heated substantially as described in Method G at 90 V for 6 seconds, except that one of the openings of the T-shaped tube was sealed with a rubber stopper, one was loosely covered with the end of the halogen tube, and the third connected to the 1 L flask. The purity of the drug-aerosol particles was determined to be >99%. All of the drug was found to have aerosolized, for a percent yield of 100%.

Example 101

Mirtazapine (MW 265, melting point 116° C., oral dose 10 mg), a psychotherapeutic agent used as an antidepressant, was coated on an aluminum foil substrate (24.5 cm$^2$) according to Method G. 20.7 mg of drug was applied to the substrate, for a calculated thickness of the drug film of 8.4 μm. The substrate was heated as described in Method G at 90 V for 6 seconds. The purity of the drug-aerosol particles was determined to be 99%. 10.65 mg was recovered from the glass tube walls after vaporization, for a percent yield of 51.4%.

Example 102

Morphine (MW 285, melting point 197° C., oral dose 15 mg), an analgesic, was coated on a stainless steel cylinder (8 cm$^2$) according to Method D. 2.33 mg of drug was applied to the substrate, for a calculated drug film thickness of 2.8 μm. The substrate was heated as described in Method D by charging the capacitors to 20.5 V. The purity of the drug-aerosol particles was determined to be 99.1%. 1.44 mg was recovered from the filter after vaporization, for a percent yield of 61.8%. A total mass of 2.2 mg was recovered from the test apparatus and substrate, for a total recovery of 94.2%.

Morphine (MW 285, melting point 197° C., oral dose 15 mg), an analgesic, was coated on a piece of aluminum foil (20 cm$^2$) according to Method C. The calculated thickness of the drug film was 4.8 μm. The substrate was heated as described in Method C at 90 V for 5 seconds. The purity of the drug-aerosol particles was determined to be 92.5%. 3.1 mg was recovered from the glass tube walls after vaporization, for a percent yield of 32.3%.

Example 103

Figure 13:
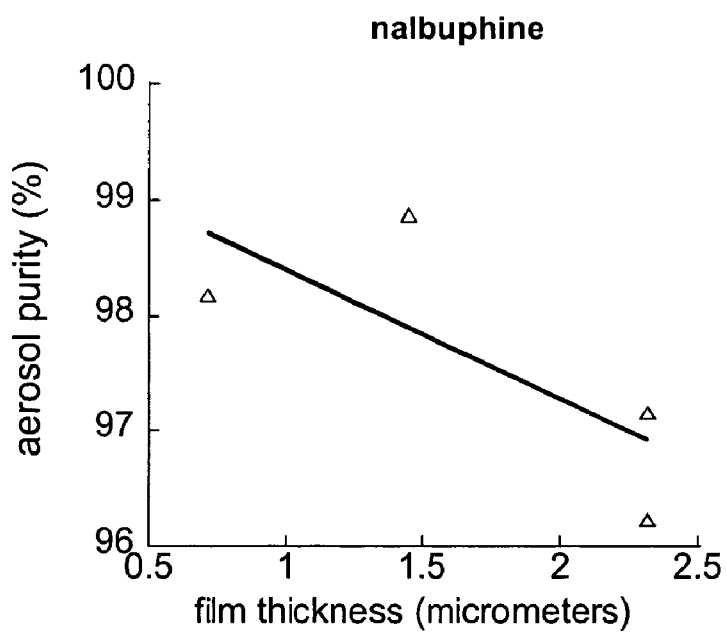
FIG. 13 is plot showing purity of thermal vapor as a function of drug film thickness, in micrometers, for nalbuphine free base.

Nalbuphine (MW 357, melting point 231° C., oral dose 10 mg), an analgesic, was coated onto four stainless steel cylinder substrates (8 cm$^2$) according to Method D. The calculated thickness of the drug film on each substrate ranged from about 0.7 μm to about 2.5 μm. The substrates were heated as described in Method D by charging the capacitors to 20.5 V. The purity of the drug-aerosol particles from each substrate was determined and the results are shown in FIG. 13. For the substrate having a drug film thickness of 0.7 μm, 0.715 mg of drug was applied to the substrate. After volatilization of this substrate, 0.455 mg was recovered from the filter, for a percent yield of 63.6%. A total mass of 0.715 mg was recovered from the test apparatus and substrate, for a total recovery of 100%.

Example 104

Naloxone (MW 327, melting point 184° C., oral dose 0.4 mg), an antidote, was coated on an aluminum foil (20 cm$^2$) according to Method C. 2.10 mg of drug was applied to the substrate, for a calculated thickness of the drug film of 1.1 μm. The substrate was heated as described in Method C at 90 V for 3.5 seconds. The purity of the drug-aerosol particles was determined to be 78.4%. 1.02 mg was recovered from the glass tube walls after vaporization, for a percent yield of 48.6%.

Another substrate containing naloxone coated to a film thickness of 1.0 μm was prepared by the same method and heated under an argon atmosphere at 90 V for 3.5 seconds. The purity of the drug-aerosol particles was determined to be 99.2%. 1.07 mg was recovered from the glass tube walls after vaporization, for a percent yield of 53.5%.

Example 105

Naproxen (MW 230, melting point 154° C., oral dose 200 mg), an analgesic, was coated on a piece of aluminum foil (20 cm$^2$) according to Method C. 8.7 mg were coated on the foil for a calculated thickness of the drug film of 4.4 μm. The substrate was heated as described in Method C at 60 V for 7 seconds. The purity of the drug-aerosol particles was determined to be >99.5%. 4.4 mg was recovered from the glass tube walls after vaporization, for a percent yield of 50.5%.

Example 106

Figure 14:
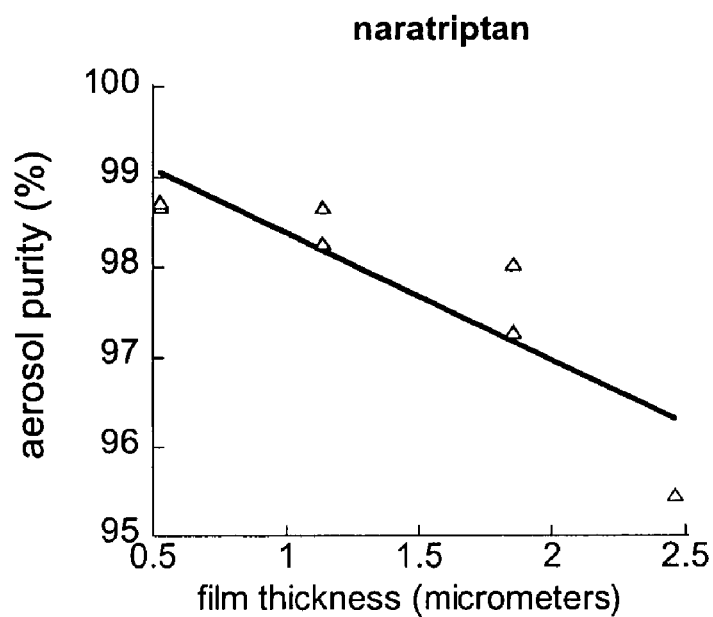
FIG. 14 is plot showing purity of thermal vapor as a function of drug film thickness, in micrometers, for naratriptan free base.

Naratriptan (MW 335, melting point 171° C., oral dose 1 mg), a migraine preparation, was coated onto seven stainless steel cylinder substrates (8 cm$^2$) according to Method D. The calculated thickness of the drug film on each substrate ranged from about 0.5 μm to about 2.5 μm. The substrates were heated as described in Method D by charging the capacitors to 20.5 V. Purity of the drug-aerosol particles from each substrate was determined and the results are shown in FIG. 14. For the substrate having a drug film thickness of 0.6 μm, 0.464 mg of drug was applied to the substrate. After vaporization of this substrate by charging the capacitors to 20.5 V. 0.268 mg was recovered from the filter, for a percent yield of 57.8%. The purity was determined to be 98.7%. A total mass of 0.464 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 100 milliseconds. Generation of the thermal vapor was complete by 250 milliseconds.

Example 107

Nefazodone (MW 470, melting point 84° C., oral dose 75 mg), a psychotherapeutic agent, was coated on a piece of aluminum foil (20 cm$^2$) according to Method C. The calculated thickness of the drug film was 4.6 μm. The substrate was heated as described in Method C at 60 V for 15 seconds. The purity of the drug-aerosol particles was determined to be 91%. 4.4 mg was recovered from the glass tube walls after vaporization, for a percent yield of 47.8%.

Another substrate containing nefazodone coated to a film thickness of 3.2 μm was prepared by the same method and heated under an argon atmosphere at 60 V for 15 seconds. The purity of the drug-aerosol particles was determined to be 97.5%. 4.3 mg was recovered from the glass tube walls after vaporization, for a percent yield of 68.3%.

Example 108

Nortriptyline (MW 263, oral dose 15 mg), a psychotherapeutic agent, was coated on an aluminum foil substrate (20 cm$^2$) according to Method C. The calculated thickness of the drug film was 1.0 μm. The substrate was heated as described in Method C at 90 V for 3.5 seconds. The purity of the drug-aerosol particles was determined to be 99.1%. 1.4 mg was recovered from the glass tube walls after vaporization, for a percent yield of 70.0%.

Another substrate containing nortriptyline was prepared for testing under an argon atmosphere. 1.90 mg of drug was applied to the substrate, for a calculated thickness of the drug film of 1.0 μm. The substrate was heated as described in Method C at 90 V for 3.5 seconds. The purity of the drug-aerosol particles was determined to be 97.8%. 1.6 mg was recovered from the glass tube walls after vaporization, for a percent yield of 84.2%.

Example 109

Figure 15:
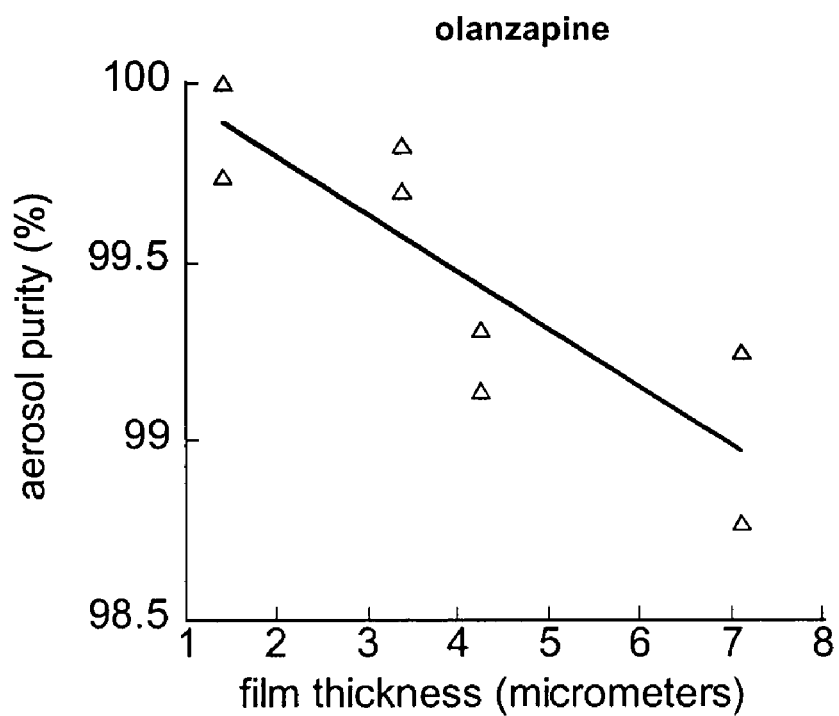
FIG. 15 is plot showing purity of thermal vapor as a function of drug film thickness, in micrometers, for olanzapine free base.

Olanzapine (MW 312, melting point 195° C., oral dose 10 mg), a psychotherapeutic agent, was coated onto eight stainless steel cylinder substrates (8-9 cm$^2$) according to Method D. The calculated thickness of the drug film on each substrate ranged from about 1.2 μm to about 7.1 μm. The substrates were heated as described in Method D by charging the capacitors to 20.5 V. Purity of the drug-aerosol particles from each substrate was determined and the results are shown in FIG. 15. The substrate having a thickness of 3.4 μm was prepared by depositing 2.9 mg of drug. After volatilization of drug from this substrate by charging the capacitors to 20.5 V. 1.633 mg was recovered from the filter, for a percent yield of 54.6%. The purity of the drug aerosol recovered from the filter was found to be 99.8%. The total mass was recovered from the test apparatus and substrate, for a total recovery of ~100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 80 milliseconds. Generation of the thermal vapor was complete by 130 milliseconds.

Olanzapine was also coated on an aluminum foil substrate (24.5 cm$^2$) according to Method G. 11.3 mg of drug was applied to the substrate, for a calculated thickness of the drug film of 4.61 μm. The substrate was heated as described in Method G at 90 V for 6 seconds. The purity of the drug-aerosol particles was determined to be >99%. 7.1 mg was collected for a percent yield of 62.8%.

Example 110

Orphenadrine (MW 269, melting point <25° C., oral dose 60 mg), a muscle relaxant, was coated on a piece of aluminum foil (20 cm$^2$) according to Method C. The calculated thickness of the drug film was 1.0 μm. The substrate was heated as described in Method C at 90 V for 3.5 seconds. The purity of the drug-aerosol particles was determined to be >99.5%. 1.35 mg was recovered from the glass tube walls after vaporization, for a percent yield of 71.1%.

Example 111

Oxycodone (MW 315, melting point 220° C., oral dose 5 mg), an analgesic, was coated on an aluminum foil substrate (20 cm$^2$) according to Method C. 2.4 mg of drug was applied to the substrate, for a calculated thickness of the drug film of 1.2 μm. The substrate was heated as described in Method C at 90 V for 3.5 seconds. The purity of the drug-aerosol particles was determined to be 99.9%. 1.27 mg was recovered from the glass tube walls after vaporization, for a percent yield of 52.9%.

Example 112

Oxybutynin (MW 358, oral dose 5 mg), a urinary tract agent, was coated on a piece of aluminum foil (20 cm$^2$) according to Method C. The calculated thickness of the drug film was 2.8 μm. The substrate was heated as described in Method C at 60 V for 6 seconds. The purity of the drug-aerosol particles was determined to be 90.6%. 3.01 mg was recovered from the glass tube walls after vaporization, for a percent yield of 54.7%.

Example 113

Parecoxib (MW 370, oral dose 10 mg), a non-steroidal anti-inflammatory analgesic, was coated on a piece of stainless steel foil (5 cm$^2$) according to Method B. The calculated thickness of the drug film was 6.0 μm. The substrate was heated as described in Method B by charging the capacitors to 15.5 V. The purity of the drug-aerosol particles was determined to be 80%. 1.264 mg was recovered from the filter after vaporization, for a percent yield of 39.5%.

Another substrate (stainless steel foil, 5 cm$^2$) was prepared by applying 0.399 mg drug to form a film having a thickness of 0.8 μm. The substrate was heated as described in Method B by charging the capacitors to 15 V. The purity of the drug-aerosol particles was determined to be 97.2%. 0.323 mg was recovered from the filter after vaporization, for a percent yield of 81.0%. A total mass of 0.324 mg was recovered from the test apparatus and substrate, for a total recovery of 81.3%.

Example 114

Paroxetine (MW 329, oral dose 20 mg), a psychotherapeutic agent, was coated on a stainless steel cylinder (8 cm$^2$) according to Method D. 2.02 mg of drug was applied to the substrate, for a calculated drug film thickness of 2.4 μm. The substrate was heated as described in Method D (with the single exception that the circuit capacitance was 1.5 Farad, not 2.0 Farad), and purity of the drug-aerosol particles was determined to be 99.5%. 1.18 mg was recovered from the filter after vaporization, for a percent yield of 58.4%. A total mass of 1.872 mg was recovered from the test apparatus and substrate, for a total recovery of 92.7%.

Paroxetine was also coated on an aluminum foil substrate (24.5 cm$^2$) as described in Method G. 19.6 mg of drug was applied to the substrate, for a calculated drug film thickness of 8 µm. The substrate was heated as described in Method G at 90 V for 6 seconds purity of the drug-aerosol particles was determined to be 88%. 7.4 mg were lost from the substrate after vaporization, for a percent yield of 37.8%.

Example 115

Pergolide (MW 314, melting point 209° C., oral dose 1 mg), an antiparkinsonian agent, was coated on a stainless steel cylinder (8 cm$^2$) according to Method D. 1.43 mg of drug was applied to the substrate, for a calculated drug film thickness of 1.9 µm. The substrate was heated as described in Method D by charging the capacitors to 20.5 V. The purity of the drug-aerosol particles was determined to be 99.7%. 1.18 mg was recovered from the filter after vaporization, for a percent yield of 82.5%. A total mass of 1.428 mg was recovered from the test apparatus and substrate, for a total recovery of 99.9%.

Pergolide was also coated on a piece of aluminum foil (20 cm$^2$) according to Method C. The calculated thickness of the drug film was 1.2 µm. The substrate was heated as described in Method C at 90 V for 3.5 seconds. The purity of the drug-aerosol particles was determined to be 98%. 0.52 mg was recovered from the glass tube walls after vaporization, for a percent yield of 22.6%.

High speed photographs were taken as the drug-coated substrate according to Method D was heated to monitor visually formation of a thermal vapor. The photographs showed that a thermal vapor was initially visible 30 milliseconds after heating was initiated, with the majority of the thermal vapor formed by 225 milliseconds. Generation of the thermal vapor was complete by 800 milliseconds.

Pergolide was further coated on an aluminum foil substrate (24.5 cm$^2$) according to Method G. 1.0 mg of the drug was applied to the substrate, for a calculated thickness of the drug film of 0.4 µm. The substrate was heated substantially as described in Method G at 90 V for 6 seconds, except that two of the openings of the T-shaped tube were left open and the third connected to the 1 L flask. The purity of the drug-aerosol particles was determined to be >99%. All of the drug was found to have aerosolized via weight loss from the substrate, for a percent yield of 100%.

Example 116

Phenytoin (MW 252, melting point 298° C., oral dose 300 mg), an anti-convulsant, was coated on a stainless steel cylinder (8 cm$^2$) according to Method D. 0.9 mg of drug was applied to the substrate, for a calculated drug film thickness of 1.1 µm. The substrate was heated as described in Method D by charging the capacitors to 20.5 V. The purity of the drug-aerosol particles was determined to be >99.5%. 0.6 mg was recovered from the filter after vaporization, for a percent yield of 66.7%. A total mass of 0.84 mg was recovered from the test apparatus and substrate, for a total recovery of 93.3%.

High speed photographs were taken as the drug-coated substrate was heated to monitor visually formation of a thermal vapor. The photographs, shown in FIGS. 24A-24D, showed that a thermal vapor was initially visible 25 milliseconds after heating was initiated, with the majority of the thermal vapor formed by 90 milliseconds. Generation of the thermal vapor was complete by 225 milliseconds.

Example 117

Pindolol (MW 248, melting point 173° C., oral dose 5 mg), a cardiovascular agent, was coated on an aluminum foil substrate (20 cm$^2$) according to Method C. 4.7 mg of drug was applied to the substrate, for a calculated thickness of the drug film of 2.4 µm. The substrate was heated as described in Method C at 60 V for 7 seconds. The purity of the drug-aerosol particles was determined to be >99.5%. 2.77 mg was recovered from the glass tube walls after vaporization, for a percent yield of 58.9%.

Another substrate containing pindolol coated to a film thickness of 3.3 µm was prepared by the same method and heated under an argon atmosphere at 60 V for 7 seconds. The purity of the drug-aerosol particles was determined to be >99.5%. 3.35 mg was recovered from the glass tube walls after vaporization, for a percent yield of 50.8%.

Example 118

Pioglitazone (MW 356, melting point 184° C., oral dose 15 mg), an antidiabetic agent, was coated on a stainless steel cylinder (8 cm$^2$) according to Method D. 0.48 mg of drug was applied to the substrate, for a calculated drug film thickness of 0.6 µm. The substrate was heated as described in Method D by charging the capacitors to 20.5 V. The purity of the drug-aerosol particles was determined to be 95.6%. 0.30 mg was recovered from the filter after vaporization, for a percent yield of 62.5%. A total mass of 0.37 mg was recovered from the test apparatus and substrate, for a total recovery of 77.1%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 100 milliseconds. Generation of the thermal vapor was complete by 125 milliseconds.

Example 119

Piribedil (MW 298, melting point 98° C., IV dose 3 mg), an antiparkinsonian agent, was coated on a stainless steel cylinder (8 cm$^2$) according to Method D. 1.1 mg of drug was applied to the substrate, for a calculated drug film thickness of 1.5 µm. The substrate was heated as described in Method D by charging the capacitors to 20.5 V. The purity of the drug-aerosol particles was determined to be 99.7%. 1.01 mg was recovered from the filter after vaporization, for a percent yield of 91.8%. A total mass of 1.1 mg was recovered from the test apparatus and substrate, for a total recovery of 100%.

Example 120

Pramipexole (MW 211, oral dose 0.5 mg), an antiparkinsonian agent, was coated on a stainless steel cylinder (8 cm$^2$) according to Method D. 1.05 mg of drug was applied to the substrate, for a calculated drug film thickness of 1.4 µm. The substrate was heated as described in Method D by charging the capacitors to 20.5 V. The purity of the drug-aerosol particles was determined to be 99.3%. 0.949 mg was recovered from the filter after vaporization, for a percent yield of 90.4%.

A total mass of 1.05 mg was recovered from the test apparatus and substrate, for a total recovery of 100%.

Pramipexole was also coated on a piece of stainless steel foil (5 cm$^2$) according to Method B. 0.42 mg of drug was applied to the substrate, for a calculated drug film thickness of 0.9 μm. The substrate was heated as described in Method B by charging the capacitors to 14 V. The purity of the drug-aerosol particles was determined to be 98.9%. 0.419 mg was recovered from the filter after vaporization, for a percent yield of 99.8%. A total mass of 0.42 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 80 milliseconds. Generation of the thermal vapor was complete by 140 milliseconds.

Example 121

Procainamide (MW 236, oral dose 125 mg), a cardiovascular agent, was coated on a stainless steel cylinder (8 cm$^2$) according to Method D. 0.95 mg of drug was applied to the substrate, for a calculated drug film thickness of 1.1 μm. The substrate was heated as described in Method D by charging the capacitors to 20.5 V. The purity of the drug-aerosol particles was determined to be >99.5%. 0.56 mg was recovered from the filter after vaporization, for a percent yield of 58.9%. A total mass of 0.77 mg was recovered from the test apparatus and substrate, for a total recovery of 81.1%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 90 milliseconds. Generation of the thermal vapor was complete by 250 milliseconds.

Example 122

Figure 18:
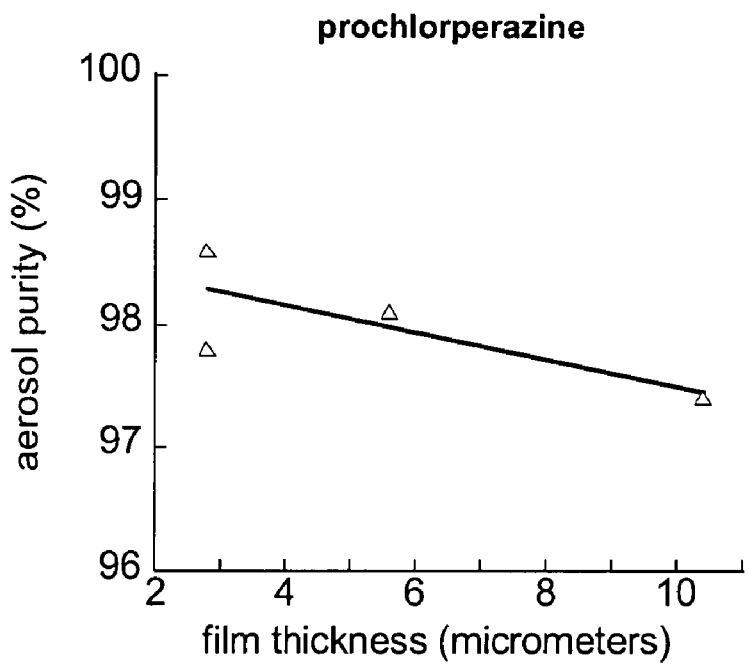
FIG. 18 is plot showing purity of thermal vapor as a function of drug film thickness, in micrometers, for prochlorperazine free base.
Figure 19:
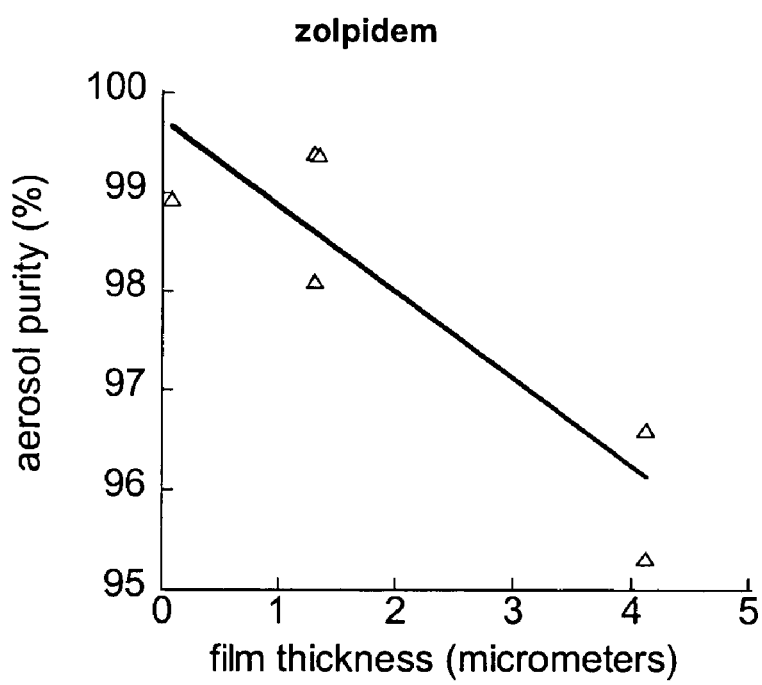
FIG. 19 is plot showing purity of thermal vapor as a function of drug film thickness, in micrometers, for zolpidem free base.
Figure 20:
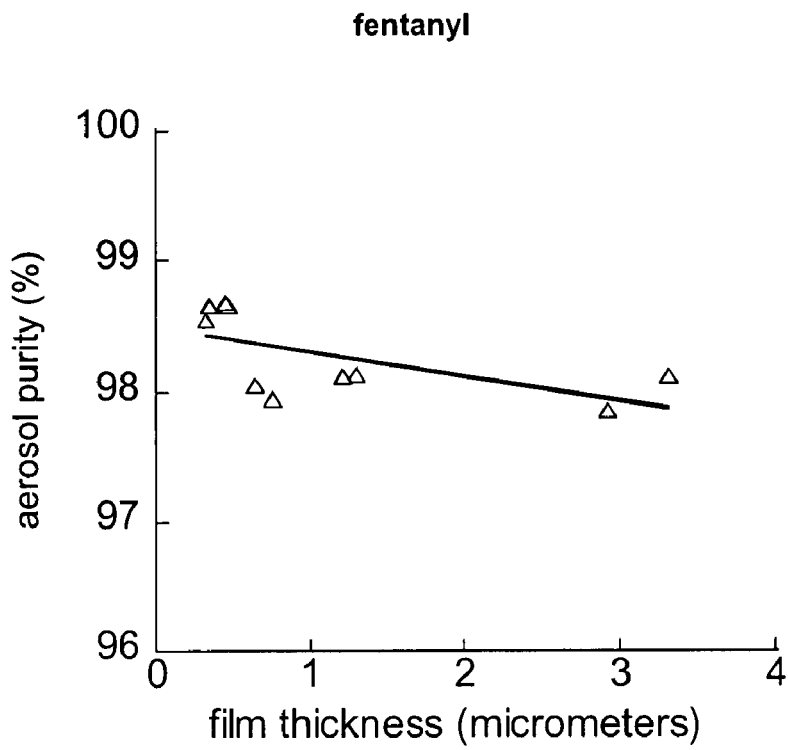
FIG. 20 is plot showing purity of thermal vapor as a function of drug film thickness, in micrometers, for fentanyl free base.

Prochlorperazine free base (MW 374, melting point 60° C., oral dose 5 mg), a psychotherapeutic agent, was coated onto four stainless steel foil substrates (5 cm$^2$) according to Method B. The calculated thickness of the drug film on each substrate ranged from about 2.3 μm to about 10.1 μm The substrates were heated as described in Method B by charging the capacitors to 15 V. Purity of the drug-aerosol particles from each substrate was determined and the results are shown in FIG. 18.

Prochlorperazine, a psychotherapeutic agent, was also coated on a stainless steel cylinder (8 cm$^2$) according to Method D. 1.031 mg of drug was applied to the substrate, for a calculated drug film thickness of 1.0 μm. The substrate was heated as described in Method D by charging the capacitors to 19 V. The purity of the drug-aerosol particles was determined to be 98.7%. 0.592 mg was recovered from the filter after vaporization, for a percent yield of 57.4%. A total mass of 1.031 mg was recovered from the test apparatus and substrate, for a total recovery of 100%.

Example 123

Promazine (MW 284, melting point <25° C., oral dose 25 mg), a psychotherapeutic agent, was coated on a piece of aluminum foil (20 cm$^2$) according to Method C. The calculated thickness of the drug film was 5.3 μm. The substrate was heated as described in Method C at 90 V for 5 seconds. The purity of the drug-aerosol particles was determined to be 94%. 10.45 mg was recovered from the glass tube walls after vaporization, for a percent yield of 99.5%.

Example 124

Promethazine (MW 284, melting point 60° C., oral dose 12.5 mg), a gastrointestinal agent, was coated on an aluminum foil substrate (20 cm$^2$) according to Method C. 5.10 mg of drug was applied to the substrate, for a calculated thickness of the drug film of 2.6 μm. The substrate was heated as described in Method C at 60 V for 10 seconds. The purity of the drug-aerosol particles was determined to be 94.5%. 4.7 mg was recovered from the glass tube walls after vaporization, for a percent yield of 92.2%.

Example 125

Propafenone (MW 341, oral dose 150 mg), a cardiovascular agent, was coated on a stainless steel cylinder (8 cm$^2$) according to Method D. 0.77 mg of drug was applied to the substrate, for a calculated drug film thickness of 0.9 μm. The substrate was heated as described in Method D by charging the capacitors to 20.5 V. The purity of the drug-aerosol particles was determined to be >99.5%. 0.51 mg was recovered from the filter after vaporization, for a percent yield of 66.2%. A total mass of 0.77 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 20 milliseconds after heating was initiated, with the majority of the thermal vapor formed by 60 milliseconds. Generation of the thermal vapor was complete by 110 milliseconds.

Example 126

Propranolol (MW 259, melting point 96° C., oral dose 40 mg), a cardiovascular agent, was coated on an aluminum foil substrate (20 cm$^2$) according to Method C. 10.30 mg of drug was applied to the substrate, for a calculated thickness of the drug film of 5.2 μm. The substrate was heated as described in Method C at 90 V for 5 seconds. The purity of the drug-aerosol particles was determined to be 99.6%. 8.93 mg was recovered from the glass tube walls after vaporization, for a percent yield of 86.7%.

Example 127

Figure 16:
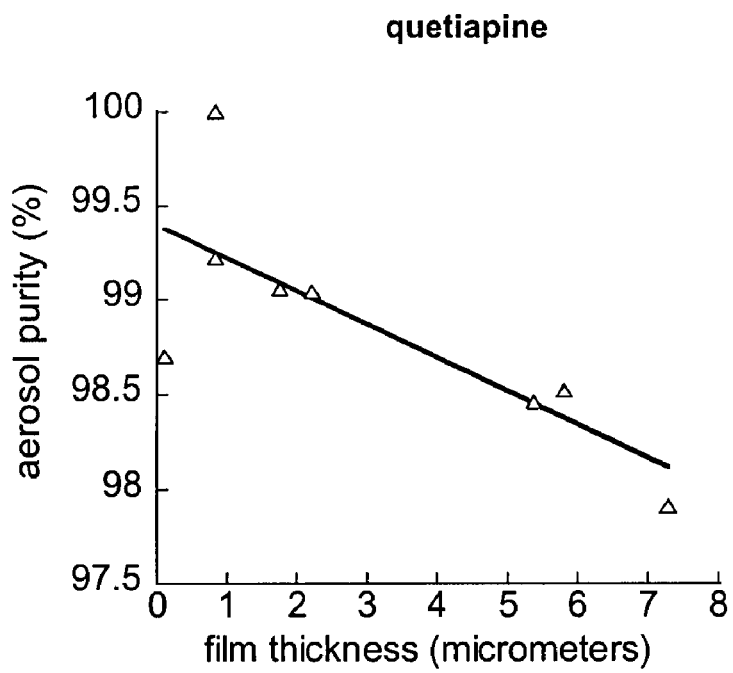
FIG. 16 is plot showing purity of thermal vapor as a function of drug film thickness, in micrometers, for quetiapine free base.

Quetiapine (MW 384, oral dose 75 mg), a psychotherapeutic agent, was coated onto eight stainless steel cylinder substrates (8 cm$^2$) according to Method D. The calculated thickness of the drug film on each substrate ranged from about 0.1 μm to about 7.1 μm. The substrates were heated as described in Method D by charging the capacitors to 20.5 V. Purity of the drug-aerosol particles from each substrate was determined and the results are shown in FIG. 16. The substrate having a drug film thickness of 1.8 μm was prepared by depositing 1.46 mg drug. After volatilization of drug this substrate by charging the capacitors to 20.5 V. 0.81 mg was recovered from the filter, for a percent yield of 55.5%. The purity of the drug aerosol recovered from the filter was found to be 99.1%. A total mass of 1.24 mg was recovered from the test apparatus and substrate, for a total recovery of 84.9%.

Example 128

Quinidine (MW 324, melting point 175° C., oral dose 100 mg), a cardiovascular agent, was coated on a stainless steel cylinder (8 cm$^2$) according to Method D. 1.51 mg of drug was applied to the substrate, for a calculated drug film thickness of 1.8 μm. The substrate was heated as described in Method D by charging the capacitors to 20.5 V. The purity of the drug-aerosol particles was determined to be >99.5%. 0.88 mg was recovered from the filter after vaporization, for a percent yield of 58.3%. A total mass of 1.24 mg was recovered from the test apparatus and substrate, for a total recovery of 82.1%.

Example 129

Rizatriptan (MW 269, melting point 121° C., oral dose 5 mg), a migraine preparation, was coated on a stainless steel cylinder (6 $cm^2$) according to Method E. 2.1 mg of drug was applied to the substrate, for a calculated drug film thickness of 3.5 μm. The substrate was heated as described in Method E and purity of the drug-aerosol particles was determined to be 99.2%. 1.66 mg was recovered from the filter after vaporization, for a percent yield of 79%. A total mass of 2.1 mg was recovered from the test apparatus and substrate, for a total recovery of 100%.

Rizatriptan was further coated on an aluminum foil substrate (150 $cm^2$) according to Method F. 10.4 mg of the drug was applied to the substrate, for a calculated thickness of the drug film of 0.7 μm. The substrate was heated as described in Method F at 250° C. and the purity of the drug-aerosol particles was determined to be 99%. 1.9 mg was collected in glass wool for a percent yield of 18.3%.

Another aluminum foil substrate (36 $cm^2$) was prepared according to Method G. 11.6 mg of rizatriptan was applied to the substrate, for a calculated thickness of the drug film of 3.2 μm. The substrate was heated substantially as described in Method G at 90 V for 7 seconds, except that one of the openings of the T-shaped tube was sealed with a rubber stopper, one was loosely covered with the end of the halogen tube, and the third connected to the 1 L flask. The purity of the drug-aerosol particles was determined to be >99%. All of the drug was found to have aerosolized, for a percent yield of 100%.

Example 130

Rofecoxib (MW 314, oral dose 50 mg), an analgesic, was coated on an aluminum foil substrate (20 $cm^2$) according to Method C. 6.5 mg of drug was applied to the substrate, for a calculated thickness of the drug film of 3.3 μm. The substrate was heated as described in Method C at 60 V for 17 seconds. The purity of the drug-aerosol particles was determined to be 97.5%. 4.1 mg was recovered from the glass tube walls after vaporization, for a percent yield of 63.1%.

Example 131

Ropinirole (MW 260, oral dose 0.25 mg), an antiparkinsonian agent, was coated on a stainless steel cylinder (8 $cm^2$) according to Method D. 0.754 mg of drug was applied to the substrate, for a calculated drug film thickness of 1.0 μm. The substrate was heated as described in Method D by charging the capacitors to 20.5 V. The purity of the drug-aerosol particles was determined to be 99%. 0.654 mg was recovered from the filter after vaporization, for a percent yield of 86.7%. A total mass of 0.728 mg was recovered from the test apparatus and substrate, for a total recovery of 96.6%.

Example 132

Sertraline (MW 306, oral dose 25 mg), a psychotherapeutic agent used as an antidepressant (Zoloft®), was coated on a stainless steel cylinder (6 $cm^2$) according to Method E. 3.85 mg of drug was applied to the substrate, for a calculated drug film thickness of 6.4 μm. The substrate was heated as described in Method E and purity of the drug-aerosol particles was determined to be 99.5%. 2.74 mg was recovered from the filter after vaporization, for a percent yield of 71.2%.

Sertraline was also coated on a piece of aluminum foil (20 $cm^2$) according to Method C. The calculated thickness of the drug film was 3.3 μm. The substrate was heated as described in Method C at 60 V for 10 seconds. The purity of the drug-aerosol particles was determined to be 98.0%. 5.35 mg was recovered from the glass tube walls after vaporization, for a percent yield of 81.1%.

Another sertraline coated substrate (aluminum foil, 20 $cm^2$) having a drug film thickness of 0.9 μm was heated as described in Method C under a pure argon atmosphere at 90 V for 3.5 seconds. The purity of the drug-aerosol particles was determined to be 98.7%. 1.29 mg was recovered from the glass tube walls after vaporization, for a percent yield of 75.9%.

High speed photographs were taken as the drug-coated substrate from Method D was heated to monitor visually formation of a thermal vapor. The photographs showed that a thermal vapor was initially visible 30 milliseconds after heating was initiated, with the majority of the thermal vapor formed by 135 milliseconds. Generation of the thermal vapor was complete by 250 milliseconds.

Example 133

Selegiline (MW 187, melting point <25° C., oral dose 5 mg), an antiparkinsonian agent, was coated on an aluminum foil substrate (20 $cm^2$) according to Method C. 3.7 mg of drug was applied to the substrate, for a calculated thickness of the drug film of 1.9 μm. The substrate was heated as described in Method C at 60 V for 8 seconds. The purity of the drug-aerosol particles was determined to be 99.2%. 2.41 mg was recovered from the glass tube walls after vaporization, for a percent yield of 65.1%.

Example 134

Sildenafil (MW 475, melting point 189° C., oral dose 25 mg), an agent used for erectile dysfunction (Viagra®), was coated onto six stainless steel foil substrates (5 $cm^2$) according to Method B. The calculated thickness of the drug film on each substrate ranged from about 0.5 μm to about 1.6 μm. The substrates were heated as described in Method B by charging the capacitors to 16 V. Purity of the drug-aerosol particles from each substrate was determined and the results are shown in FIG. 22.

Sildenafil was also coated on a stainless steel cylinder (6 $cm^2$) according to Method E. 1.9 mg of drug was applied to the substrate, for a calculated drug film thickness of 3.2 μm. The substrate was heated as described in Method E and purity of the drug-aerosol particles was determined to be 81%. 1.22 mg was recovered from the filter after vaporization, for a percent yield of 64.2%. A total mass of 1.5 mg was recovered from the test apparatus and substrate, for a total recovery of 78.6%.

Sildenafil was also coated on a piece of aluminum foil (20 $cm^2$) according to Method C. The calculated thickness of the drug film was 2.5 μm. The substrate was heated as described in Method C at 90 V for 4 seconds. The purity of the drug-aerosol particles was determined to be 66.3%. 1.05 mg was recovered from the glass tube walls after vaporization, for a percent yield of 21%.

Figure 17:
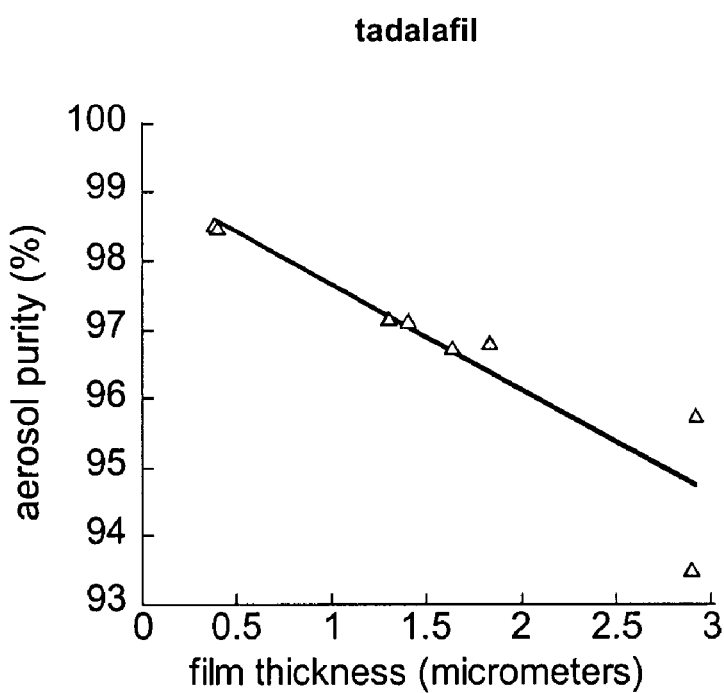
FIG. 17 is plot showing purity of thermal vapor as a function of drug film thickness, in micrometers, for tadalafil free base.

Sildenafil was also coated on a piece of stainless steel foil (6 cm$^2$) according to Method B. 0.227 mg of drug was applied to the substrate, for a calculated drug film thickness of 0.4 μm. The substrate was heated as described in Method B by charging the capacitors to 16 V. The purity of the drug-aerosol particles was determined to be 99.3%. 0.224 mg was recovered from the filter after vaporization, for a percent yield of 98.7%. A total mass of 0.227 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 45 milliseconds after heating was initiated, with the majority of the thermal vapor formed by 250 milliseconds. Generation of the thermal vapor was complete by 400 milliseconds.

Sildenafil was also coated on a piece of aluminum foil at a calculated film thickness of 3.4 μm, 3.3 μm, 1.6 μm, 0.8 μm, 0.78 μm, 0.36 μm, 0.34 μm, 0.29 μm, and 0.1 μm. The coated substrate was placed on an aluminum block that was preheated to 275° C. using a hot plate. A Pyrex© beaker was synchronously placed over the foil and the substrate was heated for 1 minute. The material collected on the beaker walls was recovered and analyzed by reverse-phase HPLC analysis with detection by absorption of 250 nm light to determine the purity of the aerosol. The purity of the drug-aerosol particles was determined to be 84.8% purity at 3.4 μm thickness; 80.1% purity at 3.3 μm thickness; 89.8% purity at 1.6 μm thickness; 93.8% purity at 0.8 μm thickness; 91.6% purity at 0.78 μm thickness; 98.0% purity at 0.36 μm thickness; 98.6% purity at 0.34 μm thickness; 97.6% purity at 0.29 μm thickness; and 100% purity at 0.1 μm thickness.

Example 135

Spironolactone (MW 417, melting point 135° C., oral dose 25 mg), a cardiovascular agent, was coated on a stainless steel cylinder (8 $cm^2$) according to Method D. 0.71 mg of drug was applied to the substrate, for a calculated drug film thickness of 0.9 μm. The substrate was heated as described in Method D by charging the capacitors to 20.5 V. The purity of the drug-aerosol particles was determined to be >99.5%. 0.41 mg was recovered from the filter after vaporization, for a percent yield of 57.7%. A total mass of 0.7 mg was recovered from the test apparatus and substrate, for a total recovery of 98.6%.

Example 136

Sumatriptan (MW 295, melting point 171° C., oral dose 6 mg), a migraine preparation, was coated on a stainless steel cylinder (8 $cm^2$) according to Method E. 1.22 mg of drug was applied to the substrate, for a calculated drug film thickness of 1.5 μm. The substrate was heated as described in Method E and purity of the drug-aerosol particles was determined to be 97.9%. 0.613 mg was recovered from the filter after vaporization, for a percent yield of 50.2%. A total mass of 1.03 mg was recovered from the test apparatus and substrate, for a total recovery of 84.4%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 175 milliseconds. Generation of the thermal vapor was complete by 600 milliseconds.

Example 137

Sibutramine (MW 280, oral dose 10 mg), an obesity management appetite suppressant, was coated on a stainless steel cylinder (8 $cm^2$) according to Method D. 1.667 mg of drug was applied to the substrate, for a calculated drug film thickness of 2 μm. The substrate was heated as described in Method D (with the single exception that the circuit capacitance was 1.5 Farad, not 2.0 Farad), and purity of the drug-aerosol particles was determined to be 94%. 0.861 mg was recovered from the filter after vaporization, for a percent yield of 51.6%. A total mass of 1.35 mg was recovered from the test apparatus and substrate, for a total recovery of 81%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 55 milliseconds. Generation of the thermal vapor was complete by 150 milliseconds.

Example 138

Tamoxifen (MW 372, melting point 98° C., oral dose 10 mg), an antineoplastic, was coated on a stainless steel cylinder (8 $cm^2$) according to Method D. 0.46 mg of drug was applied to the substrate, for a calculated drug film thickness of 0.6 μm. The substrate was heated as described in Method D by charging the capacitors to 20.5 V. The purity of the drug-aerosol particles was determined to be 91.4%. 0.27 mg was recovered from the filter after vaporization, for a percent yield of 58.7%. A total mass of 0.39 mg was recovered from the test apparatus and substrate, for a total recovery of 84.8%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 70 milliseconds. Generation of the thermal vapor was complete by 250 milliseconds.

Example 139

Tacrine (MW 198, melting point 184° C.), an Alzheimer's disease manager, was coated on a stainless steel cylinder (8 $cm^2$) according to Method D. 0.978 mg of drug was applied to the substrate, for a calculated drug film thickness of 1.2 μm. The substrate was heated as described in Method D by charging the capacitors to 20.5 V. The purity of the drug-aerosol particles was determined to be 99.8%. 0.502 mg was recovered from the filter after vaporization, for a percent yield of 51.3%. A total mass of 0.841 mg was recovered from the test apparatus and substrate, for a total recovery of 86%.

Example 140

Tadalafil (MW 389, oral dose 5 mg), an erectile dysfunction therapeutic agent, was coated onto eight stainless steel foil substrates (5 $cm^2$) according to Method B. The calculated thickness of the drug film on each substrate ranged from about 0.5 μm to about 2.9 μm. The substrates were heated as described in Method B by charging the capacitors to 16 V.

Purity of the drug-aerosol particles from each substrate was determined and the results are shown in FIG. 17.

Tadalafil was also coated on a stainless steel cylinder (8 cm$^2$). The calculated thickness of the drug film was 4.5 μm. The substrate was heated as described by the flashbulb and the purity of the drug-aerosol particles was determined to be 94.9%. 0.67 mg was recovered from the filter after vaporization, for a percent yield of 18.1%. A total mass of 1.38 mg was recovered from the test apparatus and substrate, for a total recovery of 37.3%.

Tadalafil was also coated on a piece of aluminum foil (20 cm$^2$) according to Method C. The calculated thickness of the drug film was 0.5 μm. The substrate was heated as described in Method C at 60 V for 13 seconds. The purity of the drug-aerosol particles was determined to be 91.2%. 0.45 mg was recovered from the glass tube walls after vaporization, for a percent yield of 45%.

Tadalafil was also coated on a piece of stainless steel foil (5 cm$^2$) according to Method B. 1.559 mg of drug was applied to the substrate, for a calculated drug film thickness of 2.9 μm. The substrate was heated as described in Method B by charging the capacitors to 16 V. The purity of the drug-aerosol particles was determined to be 95.8%. 1.42 mg, was recovered from the filter after vaporization, for a percent yield of 91.1%. A total mass of 1.559 mg was recovered from the test apparatus and substrate, for a total recovery of 100%.

The drug was also coated (1.653 mg) to a thickness of 3.1 μm on a piece of stainless steel foil (5 cm$^2$) according to Method B. The substrate was heated under an N$_2$ atmosphere by charging the capacitors to 16 V. The purity of the drug-aerosol particles was determined to be 99.2%. 1.473 mg was recovered from the filter after vaporization, for a percent yield of 89.1%. A total mass of 1.653 mg was recovered from the test apparatus and substrate, for a total recovery of 100%.

Example 141

Terbutaline (MW 225, melting point 122° C., oral dose 0.2 mg), a respiratory agent, was coated on a stainless steel cylinder (9 cm$^2$) according to Method D. 2.32 mg of drug was applied to the substrate, for a calculated drug film thickness of 2.7 μm. The substrate was heated as described in Method D by charging the capacitors to 20.5 V. The purity of the drug-aerosol particles was determined to be 99.3%. 1.54 mg was recovered from the filter after vaporization, for a percent yield of 66.4%. A total mass of 1.938 mg was recovered from the test apparatus and substrate, for a total recovery of 83.5%.

Example 142

Testosterone (MW 288, melting point 155° C., oral dose 3 mg), a hormone, was coated on a stainless steel cylinder (8 $cm^2$) according to Method D. 0.96 mg of drug was applied to the substrate, for a calculated drug film thickness of 1.2 μm. The substrate was heated as described in Method D by charging the capacitors to 20.5 V. The purity of the drug-aerosol particles was determined to be 99.6%. 0.62 mg was recovered from the filter after vaporization, for a percent yield of 64.6%. A total mass of 0.96 mg was recovered from the test apparatus and substrate, for a total recovery of 100%.

Example 143

Thalidomide (MW 258, melting point 271° C., oral dose 100 mg), an immunomodulator, was coated on a stainless steel cylinder (8 $cm^2$) according to Method D. 0.57 mg of drug was applied to the substrate, for a calculated drug film thickness of 0.7 μm. The substrate was heated as described in Method D by charging the capacitors to 20.5 V. The purity of the drug-aerosol particles was determined to be >99.5%. 0.43 mg was recovered from the filter after vaporization, for a percent yield of 75.4%. A total mass of 0.54 mg was recovered from the test apparatus and substrate, for a total recovery of 94.7%.

Example 144

Theophylline (MW 180, melting point 274° C., oral dose 200 mg), a respiratory agent, was coated on a stainless steel cylinder (8 $cm^2$) according to Method D. 0.859 mg of drug was applied to the substrate, for a calculated drug film thickness of 1.0 μm. The substrate was heated as described in Method D by charging the capacitors to 20.5 V. The purity of the drug-aerosol particles was determined to be 100.0%. 0.528 mg was recovered from the filter after vaporization, for a percent yield of 61.5%. A total mass of 0.859 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 160 milliseconds. Generation of the thermal vapor was complete by 350 milliseconds.

Example 145

Tocainide (MW 192, melting point 247° C., oral dose 400 mg), a cardiovascular agent, was coated on a stainless steel cylinder (8 $cm^2$) according to Method D. 0.86 mg of drug was applied to the substrate, for a calculated drug film thickness of 1 μm. The substrate was heated as described in Method D by charging the capacitors to 20.5 V. The purity of the drug-aerosol particles was determined to be 99.7%. 0.65 mg was recovered from the filter after vaporization, for a percent yield of 75.6%. A total mass of 0.86 mg was recovered from the test apparatus and substrate, for a total recovery of 100%.

High speed photographs were taken as the drug-coated substrate was heated to monitor visually formation of a thermal vapor. The photographs showed that a thermal vapor was initially visible. 25 milliseconds after heating was initiated, with the majority of the thermal vapor formed by 75 milliseconds. Generation of the thermal vapor was complete by 130 milliseconds.

Example 146

Tolfenamic Acid (MW 262, melting point 208° C., oral dose 200 mg), an analgesic, was coated on a piece of aluminum foil (20 $cm^2$) according to Method C. The calculated thickness of the drug film was 5.0 μm. The substrate was heated as described in Method C at 60 V for 6 seconds. The purity of the drug-aerosol particles was determined to be 94.2%. 6.49 mg was recovered from the glass tube walls after vaporization, for a percent yield of 65.6%.

Example 147

Tolterodine (MW 325, oral dose 2 mg), an urinary tract agent, was coated on a stainless steel cylinder (8 $cm^2$) according to Method D. 1.39 mg of drug was applied to the substrate, for a calculated drug film thickness of 1.7 μm. The substrate was heated as described in Method D by charging the capacitors to 20.5 V. The purity of the drug-aerosol particles was determined to be 96.9%. 1.03 mg was recovered from the filter after vaporization, for a percent yield of 74.1%. A total mass of 1.39 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 80 milliseconds. Generation of the thermal vapor was complete by 100 milliseconds.

Example 148

Toremifene (MW 406, melting point 110° C., oral dose 60 mg), an antineoplastic, was coated on a stainless steel cylinder (8 cm$^2$). 1.20 mg of drug was applied to the substrate, for a calculated thickness of the drug film of 1.4 μm, and heated to form drug-aerosol particles according to Method D by charging the capacitors to 20.5 V. The purity of the drug-aerosol particles was determined to be 98.7%. The yield of aerosol particles was 50%. 1.09 mg of total mass was recovered for a total recovery yield of 90.8%.

Example 149

Tramadol (MW 263, oral dose 50 mg), an analgesic, was coated on an aluminum foil substrate (20 $cm^2$) according to Method C. 4.90 mg of drug was applied to the substrate, for a calculated thickness of the drug film of 2.5 μm. The substrate was heated as described in Method C at 108 V for 2.25 seconds. The purity of the drug-aerosol particles was determined to be 96.9%. 3.39 mg was recovered from the glass tube walls after vaporization, for a percent yield of 69.2%.

Tramadol (2.6 mg) was also coated on a piece of aluminum foil (20 $cm^2$) according to Method C to a film thickness (calculated) of 1.3 μm. The substrate was heated as described in Method C under an argon atmosphere at 90 V for 3.5 seconds. The purity of the drug-aerosol particles was determined to be 96.1%. 1.79 mg was recovered from the glass tube walls after vaporization, for a percent yield of 68.8%.

Tramadol (2.1 mg) was also coated on a piece of aluminum foil (20 $cm^2$) according to Method C to a film thickness (calculated) of 1.1 μm. The substrate was heated as described in Method C under air at 90 V for 3.5 seconds. The purity of the drug-aerosol particles was determined to be 96.6%. 1.33 mg was recovered from the glass tube walls after vaporization, for a percent yield of 63.8%.

The hydrochloride salt form was also tested. 2.6 mg of drug was coated onto an aluminum foil substrate (20 $cm^2$) according to Method C to a film thickness (calculated) of 1.3 μm. The substrate was heated as described in Method C and purity of the drug-aerosol particles was determined to be 97.6%. 1.67 mg was recovered from the glass tube walls after vaporization, for a percent yield of 64.2%. An identical substrate having an identical drug film thickness was tested under an argon atmosphere at 90 V for 3.5 seconds. The purity of the drug-aerosol particles was determined to be 89%. 1.58 mg was recovered from the glass tube walls after vaporization, for a percent yield of 60.8%

Tramadol (17.5 mg) was also coated on a piece of aluminum foil (40 $cm^2$) according to Method F to a film thickness (calculated) of 4.38 μm. The substrate was heated as described in Method F and purity of the drug-aerosol particles was determined to be 97.3%.

Example 150

Tranylcypromine (MW 133, melting point <25° C., oral dose 30 mg), a psychotherapeutic agent, was coated on a piece of aluminum foil (20 $cm^2$) according to Method C. The calculated thickness of the drug film was 5.4 μm. The substrate was heated as described in Method C at 90 V for 5 seconds. The purity of the drug-aerosol particles was determined to be 93.7%. 7.4 mg was recovered from the glass tube walls after vaporization, for a percent yield of 68.5%.

Another substrate containing tranylcypromine coated to a film thickness of 2.7 μm was prepared by the same method and heated under an argon atmosphere at 90 V for 3.5 seconds. The purity of the drug-aerosol particles was determined to be 95.9%. 3 mg was recovered from the glass tube walls after vaporization, for a percent yield of 56.6%.

Tranylcypromine HCl (MW 169, melting point 166° C., oral dose 30 mg), a psychotherapeutic agent, was coated on a piece of aluminum foil (20 $cm^2$) according to Method C. The calculated thickness of the drug film was 1.2 μm. The substrate was heated as described in Method C at 90 V for 3.5 seconds. The purity of the drug-aerosol particles was determined to be 97.5%. 1.3 mg was recovered from the glass tube walls after vaporization, for a percent yield of 56.5%.

Example 151

Trazodone (MW 372, melting point 87° C., oral dose 400 mg), a psychotherapeutic agent, was coated on an aluminum foil substrate (20 $cm^2$) according to Method C. 10.0 mg of drug was applied to the substrate, for a calculated thickness of the drug film of 5.0 μm. The substrate was heated as described in Method C at 60 V for 15 seconds. The purity of the drug-aerosol particles was determined to be 98.9%. 8.5 mg was recovered from the glass tube walls after vaporization, for a percent yield of 85%.

Trazodone was further coated on an aluminum foil substrate according to Method G. The substrate was heated as described in Method G at 90 V for 3.5 seconds. The purity of the drug-aerosol particles was determined to be 97.9%. The percent yield of the aerosol was 29.1%. The purity of the drug-aerosol particles was determined to be 98.5% when the system was flushed through with argon prior to volatilization. The percent yield of the aerosol was 25.5%.

Example 152

Triazolam (MW 343, melting point 235° C., oral dose 0.13 mg), a sedative and hypnotic, was coated on an aluminum foil substrate (20 $cm^2$) according to Method C. 1.7 mg of drug was applied to the substrate, for a calculated thickness of the drug film of 0.9 μm. The substrate was heated as described in Method C at 45 V for 18 seconds. The purity of the drug-aerosol particles was determined to be 99.2%. 1.6 mg was recovered from the glass tube walls after vaporization, for a percent yield of 94.1%.

Another aluminum foil substrate (28.8 $Cm^2$) was prepared according to Method C. 1.7 mg of triazolam was applied to the substrate, for a calculated thickness of the drug film of 0.69 μm. The substrate was heated substantially as described in Method C at 75 V for 2 seconds and then at 45 V for 8 seconds. The purity of the drug-aerosol particles was determined to be 99.3%. 1.7 mg of aerosol particles were collected for a percent yield of 100%

Triazolam was also applied to an aluminum foil substrate (36 $cm^2$) according to Method G. 0.6 mg of the drug was applied to the substrate, for a calculated thickness of the drug film of 0.17 μm. The substrate was heated substantially as described in Method G at 90 V for 6 seconds, except that one of the openings of the T-shaped tube was sealed with a rubber stopper, one was loosely covered with the end of the halogen tube, and the third connected to the 1 L flask. The purity of the drug-aerosol particles was determined to be >99%. All of the drug was found to have aerosolized, for a percent yield of 100%.

Example 153

Trifluoperazine (MW 407, melting point <25° C., oral dose 7.5 mg), a psychotherapeutic agent, was coated on a stainless steel cylinder (9 cm$^2$) according to Method D. 1.034 mg of drug was applied to the substrate, for a calculated drug film thickness of 1.1 μm. The substrate was heated as described in Method D by charging the capacitors to 19 V. The purity of the drug-aerosol particles was determined to be 99.8%. 0.669 mg was recovered from the filter after vaporization, for a percent yield of 64.7%. A total mass of 1.034 mg was recovered from the test apparatus and substrate, for a total recovery of 100%.

Trifluoperazine 2HCl salt (MW 480, melting point 243° C., oral dose 7.5 mg) was coated on an identical substrate. Specifically, 0.967 mg of drug was applied to the substrate, for a calculated drug film thickness of 1.1 μm. The substrate was heated as described in Method D by charging the capacitors to 20.5 V. The purity of the drug-aerosol particles was determined to be 87.5%. 0.519 mg was recovered from the filter after vaporization, for a percent yield of 53.7%. A total mass of 0.935 mg was recovered from the test apparatus and substrate, for a total recovery of 96.7%.

High speed photographs of trifluoperazine 2HCl were taken as the drug-coated substrate was heated to monitor visually formation of a thermal vapor. The photographs showed that a thermal vapor was initially visible 25 milliseconds after heating was initiated, with the majority of the thermal vapor formed by 120 milliseconds. Generation of the thermal vapor was complete by 250 milliseconds.

Example 154

Trimipramine maleate (MW 411, melting point 142° C., oral dose 50 mg), a psychotherapeutic agent, was coated on a piece of aluminum foil (20 cm$^2$) according to Method C. The calculated thickness of the drug film was 1.2 μm. The substrate was heated as described in Method C at 90 V for 3.5 seconds. The purity of the drug-aerosol particles was determined to be 95.9%. 1.6 mg was recovered from the glass tube walls after vaporization, for a percent yield of 66.7%.

Another substrate containing trimipramine maleate coated to a film thickness of 1.1 μm was prepared by the same method and heated under an argon atmosphere at 90 V for 3.5 seconds. The purity of the drug-aerosol particles was determined to be 97.4%. 2.1 mg was recovered from the glass tube walls after vaporization, for a percent yield of 95.5%.

Example 155

Valdecoxib (MW 314, melting point 155° C., oral dose 10 mg), an anti-rheumatic agent, was coated on a piece of stainless steel foil (5 cm$^2$) according to Method B. The calculated thickness of the drug film was 8.0 μm. The substrate was heated as described in Method B by charging the capacitors to 15.5 V. The purity of the drug-aerosol particles was determined to be 96.9%. 1.235 mg was recovered from the filter after vaporization, for a percent yield of 28.9%. A total mass of 3.758 mg was recovered from the test apparatus and substrate, for a total recovery of 87.9%.

Valdecoxib was also coated on a piece of stainless steel foil (6 cm$^2$) according to Method B. 0.716 mg of drug was applied to the substrate, for a calculated drug film thickness of 1.3 μm. The substrate was heated as described in Method B by charging the capacitors to 15 V. The purity of the drug-aerosol particles was determined to be 98.6%. 0.466 mg was recovered from the filter after vaporization, for a percent yield of 65.1%. A total mass of 0.49 mg was recovered from the test apparatus and substrate, for a total recovery of 68.4%.

Example 156

Valproic Acid (MW 144, melting point <25° C., oral dose 60 mg), an anticonvulsant, was coated on a metal substrate (50 cm$^2$) according to Method F. 82.4 mg of drug was applied to the substrate, for a calculated drug film thickness of 16.5 μm. The substrate was heated according to Method F at 300° C. to form drug-aerosol particles. Purity of the drug-aerosol particles was determined to be 99.7% by GC analysis. 60 mg of the drug were collected for a percent yield of 72.8%.

Example 157

Vardenafil (MW 489, oral dose 5 mg), an erectile dysfunction therapy agent, was coated on a stainless steel cylinder (6 cm$^2$) according to Method E. The calculated thickness of the drug film was 2.7 μm. The substrate was heated as described in Method E and purity of the drug-aerosol particles was determined to be 79%. 0.723 mg was recovered from the filter after vaporization, for a percent yield of 44.4%.

Another substrate (stainless steel cylinder (6 cm$^2$)) was prepared by applying 0.18 mg drug to form a film 0.3 μm in thickness. The substrate was heated as described in Method E and purity of the drug-aerosol particles was determined to be 96.8%. 0.11 mg was recovered from the filter after vaporization, for a percent yield of 63.1%. A total mass of 0.14 mg was recovered from the test apparatus and substrate, for a total recovery of 81.8%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 90 milliseconds. Generation of the thermal vapor was complete by 110 milliseconds.

Example 158

Venlafaxine (MW 277, oral dose 50 mg), a psychotherapeutic agent, was coated on a stainless steel cylinder (6 cm$^2$) according to Method E. 5.85 mg of drug was applied to the substrate, for a calculated drug film thickness of 9.8 μm. The substrate was heated as described in Method E and purity of the drug-aerosol particles was determined to be 99.4%. 3.402 mg was recovered from the filter after vaporization, for a percent yield of 58.1%. A total mass of 5.85 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 100 milliseconds. Generation of the thermal vapor was complete by 400 milliseconds.

Example 159

Verapamil (MW 455, melting point <25° C., oral dose 40 mg), a cardiovascular agent, was coated on a piece of aluminum foil (20 cm$^2$) according to Method C. The calculated thickness of the drug film was 1.1 µm. The substrate was heated under an argon atmosphere at 90 V for 3.5 seconds. The purity of the drug-aerosol particles was determined to be 96.2%. 1.41 mg was recovered from the glass tube walls after vaporization, for a percent yield of 64.1%.

Verapamil was also coated on a stainless steel cylinder (8 cm$^2$) according to Method D. 0.75 mg of drug was applied to the substrate, for a calculated drug film thickness of 0.9 µm. The substrate was heated as described in Method D by charging the capacitors to 20.5 V. The purity of the drug-aerosol particles was determined to be 89.6%. 0.32 mg was recovered from the filter after vaporization, for a percent yield of 42.7%. A total mass of 0.6 mg was recovered from the test apparatus and substrate, for a total recovery of 80%.

Example 160

Vitamin E (MW 430, melting point 4° C.), a dietary supplement, was coated on a stainless steel cylinder (8 cm$^2$) according to Method D. 0.78 mg of drug was applied to the substrate, for a calculated drug film thickness of 0.9 µm. The substrate was heated as described in Method D by charging the capacitors to 20.5 V. The purity of the drug-aerosol particles was determined to be 99.3%. 0.48 mg was recovered from the filter after vaporization, for a percent yield of 61.8%. A total mass of 0.6 mg was recovered from the test apparatus and substrate, for a total recovery of 81.4%.

Example 161

Zaleplon (MW 305, melting point 159° C., oral dose 5 mg), a sedative and hypnotic, was coated on a piece of aluminum foil (20 cm$^2$) according to Method C. The calculated thickness of the drug film was 2.3 µm. The substrate was heated as described in Method C at 60 V for 12 seconds. The purity of the drug-aerosol particles was determined to be 99.5%. 4.07 mg was recovered from the glass tube walls after vaporization, for a percent yield of 90.4%.

Example 162

Zolmitriptan (MW 287, melting point 141° C., oral dose 1.25 mg), a migraine preparation, was coated on a piece of aluminum foil (20 cm$^2$) according to Method C. The calculated thickness of the drug film was 1.6 µm. The substrate was heated as described in Method C at 60 V for 11 seconds. The purity of the drug-aerosol particles was determined to be 93%. 1.1 mg was recovered from the glass tube walls after vaporization, for a percent yield of 35.5%.

Another substrate containing zolmitriptan coated to a film thickness of 2.0 µm was prepared by the same method and heated under an argon atmosphere at 90 V for 4 seconds. The purity of the drug-aerosol particles was determined to be 98.4%. 0.6 mg was recovered from the glass tube walls after vaporization, for a percent yield of 15%.

Another substrate (36 cm$^2$) containing zolmitriptan was prepared according to Method C. 9.8 mg of the drug was applied to the substrate, for a calculated thickness of the drug film of 2.7 µm. The substrate was heated substantially as described in Method C at 60 V for 15 seconds. The purity of the drug-aerosol particles was determined to be 98%. The aerosol percent yield was 38%.

Zolmitriptan was further coated on an aluminum foil substrate (24.5 cm$^2$) according to Method G. 2.6 mg of the drug was applied to the substrate, for a calculated thickness of the drug film of 1.1 µm. The substrate was heated as described in Method G at 90 V for 6 seconds. The purity of the drug-aerosol particles was determined to be >96%. 1.5 mg of the drug was found to have aerosolized, for a percent yield of 57.7%.

Example 163

Zolpidem (MW 307, melting point 196° C., oral dose 5 mg), a sedative and hypnotic, was coated onto six stainless steel cylindrical substrates according to Method E. The calculated thickness of the drug film on each substrate ranged from about 0.1 μm to about 4.2 μm. The substrates were heated as described in Method E and purity of the drug-aerosol particles generated from each substrate determined. The results are shown in FIG. 19.

Zolpidem was also coated on a stainless steel cylinder (6 $cm^2$) according to Method E. 4.13 mg of drug was applied to the substrate, for a calculated drug film thickness of 6.9 μm. The substrate was heated as described in Method E and purity of the drug-aerosol particles was determined to be 96.6%. 2.6 mg was recovered from the filter after vaporization, for a percent yield of 63%. A total mass of 3.18 mg was recovered from the test apparatus and substrate, for a total recovery of 77%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 120 milliseconds. Generation of the thermal vapor was complete by 225 milliseconds.

Zolpidem was also coated on an aluminum substrate (24.5 $cm^2$) according to Method G. 8.3 mg of drug was applied to the substrate, for a calculated drug film thickness of 3.4 μm. The substrate was heated as described in Method G at 90 V for 6 seconds. The purity of the drug-aerosol particles was determined to be >97%. 7.4 mg of the drug was found to have aerosolized by weight loss from substrate mass, for a percent yield of 89.2%.

Example 164

Zopiclone (MW 388, melting point 178° C., oral dose 7.50 mg), a sedative and hypnotic, was coated on an aluminum foil substrate (20 $cm^2$) according to Method C. 3.7 mg of drug was applied to the substrate, for a calculated thickness of the drug film of 1.9 μm. The substrate was heated as described in Method C at 60 V for 9 seconds. The purity of the drug-aerosol particles was determined to be 97.9%. 2.5 mg was recovered from the glass tube walls after vaporization, for a percent yield of 67.6%.

Zopiclone was further coated on an aluminum foil substrate (24 $cm^2$) according to Method C. 3.5 mg of drug was applied to the substrate, for a calculated thickness of the drug film of 1.5 μm. The substrate was heated substantially as described in Method C at 60 V for 6 seconds. The purity of the drug-aerosol particles was determined to be >99%.

Example 165

Zotepine (MW 332, melting point 91° C., oral dose 25 mg), a psychotherapeutic agent, was coated on a stainless steel cylinder (8 $cm^2$) according to Method D. 0.82 mg of drug was applied to the substrate, for a calculated drug film thickness of 1 μm. The substrate was heated as described in Method D by charging the capacitors to 20.5 V. The purity of the drug-aerosol particles was determined to be 98.3%. 0.72 mg was recovered from the filter after vaporization, for a percent yield of 87.8%. A total mass of 0.82 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 60 milliseconds. Generation of the thermal vapor was complete by 110 milliseconds.

Example 166

Adenosine (MW 267, melting point 235° C., oral dose 6 mg), an anti-arrhythmic cardiovascular agent, was coated on a stainless steel cylinder (8 cm$^2$) according to Method D. 1.23 mg of drug was applied to the substrate, for a calculated drug film thickness of 1.5 μm. The substrate was heated as described in Method D by charging the capacitors to 20.5 V. The purity of the drug-aerosol particles was determined to be 70.6%. 0.34 mg was recovered from the filter after vaporization, for a percent yield of 27.6%. A total mass of 0.68 mg was recovered from the test apparatus and substrate, for a total recovery of 55.3%.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 250 milliseconds. Generation of the thermal vapor was complete by 535 milliseconds.

Example 167

Amoxapine (MW 314, melting point 176° C., oral dose 25 mg), an anti-psychotic agent, was coated on a stainless steel cylinder (8 cm$^2$) according to Method D. 6.61 mg of drug was applied to the substrate, for a calculated drug film thickness of 7.9 μm. The substrate was heated as described in Method D by charging the capacitors to 20.5 V. The purity of the drug-aerosol particles was determined to be 99.7%. 3.13 mg was recovered from the filter after vaporization, for a percent yield of 47.4%. A total mass of 6.61 mg was recovered from the test apparatus and substrate, for a total recovery of 100%.

Example 168

Apomorphine 10,11 cyclocarbonate (MW 293, typical aerosol dose 1 mg), a dopaminergic agent used in Parkinson's patients, was coated on a piece of aluminum foil (20 cm$^2$) according to Method C. The calculated thickness of the drug film was 1.2 μm. The substrate was heated as described in Method C at 90 V for 3 seconds. The purity of the drug-aerosol particles was determined to be 78.4%. 1.46 mg was recovered from the glass tube walls after vaporization, for a percent yield of 60.8%.

Example 169

Aripiprazole (MW 448, melting point 140° C., oral dose 5 mg), an anti-psychotic agent, was coated on a stainless steel cylinder (8 cm$^2$) according to Method D. 1.139 mg of drug was applied to the substrate, for a calculated drug film thickness of 1.4 μm. The substrate was heated as described in Method D by charging the capacitors to 20.5 V. The purity of the drug-aerosol particles was determined to be 91.1%. 0.251 mg was recovered from the filter after vaporization, for a percent yield of 22%. A total mass of 1.12 mg was recovered from the test apparatus and substrate, for a total recovery of 98%.

High speed photographs were taken as the drug-coated substrate was heated to monitor visually formation of a thermal vapor. The photographs showed that a thermal vapor was initially visible 55 milliseconds after heating was initiated, with the majority of the thermal vapor formed by 300 milliseconds. Generation of the thermal vapor was complete by 1250 milliseconds.

A second substrate coated with arirpirazole was prepared for testing. 1.139 mg was coated on a stainless steel cylinder (8 cm$^2$) according to Method D, for a calculated drug film thickness of 1.4 μm. The substrate was heated as described in Method D by charging the capacitors to 20.5 V. The purity of the drug-aerosol particles was determined to be 86.9%. 0.635 mg was recovered from the filter after vaporization, for a percent yield of 55.8%. A total mass of 1.092 mg was recovered from the test apparatus and substrate, for a total recovery of 95.8%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 200 milliseconds. Generation of the thermal vapor was complete by 425 milliseconds.

Example 170

Aspirin (MW 180, melting point 135° C., oral dose 325 mg), an analgesic agent, was coated on a piece of aluminum foil (20 cm$^2$) according to Method C. The calculated thickness of the drug film was 1.2 μm. The substrate was heated as described in Method C at 60 V for 5 seconds. The purity of the drug-aerosol particles was determined to be 82.1%. 1.23 mg was recovered from the glass tube walls after vaporization, for a percent yield of 53.5%.

Example 171

Astemizole (MW 459, melting point 173° C., oral dose 10 mg), an antihistamine, was coated on an aluminum foil substrate (20 cm$^2$) according to Method C. 5.0 mg of drug was applied to the substrate, for a calculated thickness of the drug film of 2.5 μm. The substrate was heated as described in Method C at 60 V for 11 seconds. The purity of the drug-aerosol particles was determined to be 88%. 1.6 mg was recovered from the glass tube walls after vaporization, for a percent yield of 32.0%.

A similarly prepared substrate having the same film thickness was heated at 60 V for 11 seconds under a pure argon atmosphere. The purity of the drug-aerosol particles was determined to be 93.9%. 1.7 mg was recovered from the glass tube walls after vaporization, for a percent yield of 34.0%.

Example 172

Atenolol (MW 266, melting point 152° C., oral dose 25 mg), a beta adrenergic blocking agent, was coated on a piece of aluminum foil (20 cm$^2$) according to Method C. 22.6 mg was applied to the substrate, for a calculated thickness of the drug film of 11.3 μm. The substrate was heated as described in Method C at 60 V for 11 seconds. The purity of the drug-aerosol particles was determined to be 94%. 1.0 mg was recovered from the glass tube walls after vaporization, for a percent yield of 4.4%.

Another atenolol-coated substrate was prepared by the same method, with 17.9 mg of drug applied to the substrate, for a calculated film thickness of 9.0 µm. The substrate was heated under an argon atmosphere according to Method C at 60 V for 3.5 seconds. The purity of the drug-aerosol particles was determined to be >99.5%. 2.0 mg was recovered from the glass tube walls after vaporization, for a percent yield of 11%.

Atenolol was further coated on an aluminum foil substrate according to Method G. The substrate was heated as described in Method G, and the purity of the drug-aerosol particles was determined to be 100%. The percent yield of the aerosol was 10%.

Example 173

Benazepril (MW 424, melting point 149° C., oral dose 10 mg), an ACE inhibitor, cardiovascular agent, was coated on a stainless steel cylinder (8 $cm^2$) according to Method D. The calculated thickness of the drug film was 0.9 μm. The substrate was heated as described in Method D by charging the capacitors to 20.5 V. The purity of the drug-aerosol particles was determined to be 90%. 0.34 mg was recovered from the filter after vaporization, for a percent yield of 45.3%. A total mass of 0.6 mg was recovered from the test apparatus and substrate, for a total recovery of 77.3%.

Example 174

Benztropine (MW 307, melting point 143° C., oral dose 1 mg), an anti-cholinergic, antiparkinsonian agent, was coated onto an aluminum foil substrate (20 $cm^2$) according to Method C. 2.10 mg of drug was applied to the substrate, for a calculated thickness of the drug film of 1.1 μm. The substrate was heated as described in Method C at 90 V for 3.5 seconds. The purity of the drug-aerosol particles was determined to be 98.3%. 0.83 mg was recovered from the glass tube walls after vaporization, for a percent yield of 39.5%.

Another benztropine-coated substrate was prepared by the same method, with 2.0 mg of drug was applied to the substrate, for a calculated film thickness of 1.0 μm. The substrate was heated under an argon atmosphere at 90 V for 3.5 seconds. The purity of the drug-aerosol particles was determined to be 99.5%. 0.96 mg was recovered from the glass tube walls after vaporization, for a percent yield of 48%.

Example 175

Bromazepam (MW 316, melting point 239° C., oral dose 2 mg), a psychotherapeutic agent used as an anti-anxiety drug, was coated on a piece of aluminum foil (20 $cm^2$) according to Method C. The calculated thickness of the drug film was 5.2 μm. The substrate was heated as described in Method C at 30 V for 45 seconds. The purity of the drug-aerosol particles was determined to be 96.9%. 2.2 mg was recovered from the glass tube walls after vaporization, for a percent yield of 21.2%.

Example 176

Budesonide (MW 431, melting point 232° C., oral dose 0.2 mg), an anti-inflammatory steroid used as a respiratory agent, was coated on a stainless steel cylinder (9 $cm^2$) according to Method D. 1.46 mg of drug was applied to the substrate, for a calculated drug film thickness of 1.7 μm. The substrate was heated as described in Method D by charging the capacitors to 20.5 V. The purity of the drug-aerosol particles was determined to be 70.5%. 0.37 mg was recovered from the filter after vaporization, for a percent yield of 25.3%. A total mass of 0.602 mg was recovered from the test apparatus and substrate, for a total recovery of 41.2%.

Example 177

Buspirone (MW 386, oral dose 15 mg), a psychotherapeutic agent, was coated on an aluminum foil substrate (20 $cm^2$) according to Method C. 7.60 mg of drug was applied to the substrate, for a calculated thickness of the drug film of 3.8 μm. The substrate was heated as described in Method C at 60 V for 7 seconds. The purity of the drug-aerosol particles was determined to be 96.5%. 1.75 mg was recovered from the glass tube walls after vaporization, for a percent yield of 23%.

Another substrate containing buspirone coated to a film thickness of 4.6 μm was prepared by the same method and heated under an argon atmosphere at 60 V for 7 seconds. The purity of the drug-aerosol particles was determined to be 96.1%. 2.7 mg was recovered from the glass tube walls after vaporization, for a percent yield of 29.7%.

The hydrochloride salt (MW 422) was also tested. Buspirone hydrochloride was coated on a piece of aluminum foil (20 $cm^2$) according to Method C. 8.30 mg of drug was applied to the substrate, for a calculated thickness of the drug film of 4.2 μm. The substrate was heated as described in Method C at 90 V for 5 seconds. The purity of the drug-aerosol particles was determined to be 97.8%. 2.42 mg was recovered from the glass tube walls after vaporization, for a percent yield of 29.2%.

Example 178

Caffeine (MW 194, melting point 238° C., oral dose 100 mg), a central nervous system stimulant, was coated on a metal substrate (50 $cm^2$). 100 mg of drug was applied to the substrate, for a calculated drug film thickness of 14 μm and heated to 300° C. according to Method F to form drug-aerosol particles. Purity of the drug-aerosol particles was determined to be >99.5%. 40 mg was recovered from the glass wool after vaporization, for a percent yield of 40%.

Example 179

Captopril (MW 217, melting point 104° C., oral dose 25 mg), an ACE inhibitor, cardiovascular agent, was coated on a stainless steel cylinder (8 $cm^2$) according to Method D. 0.88 mg of drug was applied to the substrate, for a calculated drug film thickness of 1.1 μm. The substrate was heated as described in Method D by charging the capacitors to 20.5 V. The purity of the drug-aerosol particles was determined to be 87.5%. 0.54 mg was recovered from the filter after vaporization, for a percent yield of 61.4%. A total mass of 0.8 mg was recovered from the test apparatus and substrate, for a total recovery of 90.9%.

High speed photographs were taken as the drug-coated substrate was heated to monitor visually formation of a thermal vapor. The photographs showed that a thermal vapor was initially visible 20 milliseconds after heating was initiated, with the majority of the thermal vapor formed by 100 milliseconds. Generation of the thermal vapor was complete by 170 milliseconds.

Example 180

Carbamazepine (MW 236, melting point 193° C., oral dose 200 mg), an anticonvulsant agent, was coated on a stainless steel cylinder (8 cm$^2$) according to Method D. 0.73 mg of drug was applied to the substrate, for a calculated drug film thickness of 0.9 μm. The substrate was heated as described in Method D by charging the capacitors to 20.5 V. The purity of the drug-aerosol particles was determined to be 88.9%. 0.43 mg was recovered from the filter after vaporization, for a percent yield of 58.9%. A total mass of 0.6 mg was recovered from the test apparatus and substrate, for a total recovery of 78.1%.

Example 181

Cinnarizine (MW 369, oral dose 15 mg), an antihistamine, was coated on an aluminum foil substrate (20 cm$^2$) according to Method C. 18.0 mg of drug was applied to the substrate, for a calculated thickness of the drug film of 9 μm. The substrate was heated as described in Method C at 60 V for 8 seconds. The purity of the drug-aerosol particles was determined to be 96.7%. 3.15 mg was recovered from the glass tube walls after vaporization, for a percent yield of 17.5%.

Another substrate containing cinnarizine coated (5.20 mg drug) to a film thickness of 2.6 μm was prepared by the same method and heated under an argon atmosphere at 60 V for 8 seconds. The purity of the drug-aerosol particles was determined to be 91.8%. 2.3 mg was recovered from the glass tube walls after vaporization, for a percent yield of 44.2%.

Example 182

Clemastine (MW 344, melting point <25° C., oral dose 1 mg), a antihistamine, was coated on a piece of aluminum foil (20 cm$^2$) according to Method C. The calculated thickness of the drug film was 3.2 μm. The substrate was heated as described in Method C at 60 V for 7 seconds. The purity of the drug-aerosol particles was determined to be 94.3%. 3 mg was recovered from the glass tube walls after vaporization, for a percent yield of 46.9%.

Clemastine fumarate (MW 460, melting point 178° C., oral dose 1.34 mg) was coated on an identical substrate to a thickness of 2.9 μm. The substrate was heated at 60 V for 8 seconds. The purity of the drug-aerosol particles was determined to be 76.6%. 1.8 mg was recovered from the glass tube walls after vaporization, for a percent yield of 31.6%.

Example 183

Clofazimine (MW 473, melting point 212° C., oral dose 100 mg), an anti-infective agent, was coated on a stainless steel cylinder (6 cm$^2$) according to Method D. 0.48 mg of drug was applied to the substrate, for a calculated drug film thickness of 0.8 μm. The substrate was heated as described in Method D by charging the capacitors to 20.5 V. The purity of the drug-aerosol particles was determined to be 84.4%. 0.06 mg was recovered from the filter after vaporization, for a percent yield of 12.5%. A total mass of 0.48 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 45 milliseconds after heating was initiated, with the majority of the thermal vapor formed by 300 milliseconds. Generation of the thermal vapor was complete by 1200 milliseconds.

Example 184

Desipramine (MW 266, melting point <25° C., oral dose 25 mg), a psychotherapeutic agent, was coated on a piece of aluminum foil (20 cm$^2$) according to Method C. The calculated thickness of the drug film was 5.2 μm. The substrate was heated as described in Method C at 90 V for 5 seconds. The purity of the drug-aerosol particles was determined to be 82.2%. 7.2 mg was recovered from the glass tube walls after vaporization, for a percent yield of 69.9%.

Example 185

Dipyridamole (MW 505, melting point 163° C., oral dose 75 mg), a blood modifier, was coated on a stainless steel cylinder (6 cm$^2$) according to Method D. 1.15 mg of drug was applied to the substrate, for a calculated drug film thickness of 1.9 μm. The substrate was heated as described in Method D by charging the capacitors to 20.5 V. The purity of the drug-aerosol particles was determined to be 95.3%. 0.22 mg was recovered from the filter after vaporization, for a percent yield of 19.1%. A total mass of 1.1 mg was recovered from the test apparatus and substrate, for a total recovery of 94.8%.

Example 186

Dolasetron (MW 324, oral dose 100 mg), a gastrointestinal agent, was coated on a piece of aluminum foil (20 cm$^2$) according to Method C. The calculated thickness of the drug film was 5 μm. The substrate was heated as described in Method C at 30 V for 45 seconds. The purity of the drug-aerosol particles was determined to be 83%. 6 mg was recovered from the glass tube walls after vaporization, for a percent yield of 60%.

Dolasetron was further coated on an aluminum foil substrate according to Method C. The substrate was heated substantially as described in Method C, and the purity of the drug-aerosol particles was determined to be 99%.

Example 187

Doxylamine (MW 270, melting point <25° C., oral dose 12.5 mg), an antihistamine, was coated on a stainless steel cylinder (8 cm$^2$) according to Method D. The calculated thickness of the drug film was 7.8 μm. The substrate was heated as described in Method D by charging the capacitors to 20.5 V. The purity of the drug-aerosol particles was determined to be 99.8%. 2.96 mg was recovered from the filter after vaporization, for a percent yield of 45.6%. A total mass of 6.49 mg was recovered from the test apparatus and substrate, for a total recovery of 100%.

Example 188

Droperidol (MW 379, melting point 147° C., oral dose 1 mg), a psychotherapeutic agent, was coated on a piece of aluminum foil (20 cm$^2$) according to Method C. The calculated thickness of the drug film was 1.1 μm. The substrate was heated as described in Method C at 90 V for 3.5 seconds. The purity of the drug-aerosol particles was determined to be 51%. 0.27 mg was recovered from the glass tube walls after vaporization, for a percent yield of 12.9%.

Another substrate containing droperidol coated to a film thickness of 1.0 μm was prepared by the same method and heated under an argon atmosphere at 90 V for 3.5 seconds. The purity of the drug-aerosol particles was determined to be 65%. 0.24 mg was recovered from the glass tube walls after vaporization, for a percent yield of 12.6%.

Example 189

Enalapril maleate (MW 493, melting point 145° C., oral dose 5 mg), a cardiovascular agent, was coated on a stainless steel cylinder (8 cm$^2$) according to Method D. The calculated thickness of the drug film was 1.1 μm. The substrate was heated as described in Method D by charging the capacitors to 20.5 V. The purity of the drug-aerosol particles was determined to be 61%. 0.29 mg was recovered from the filter after vaporization, for a percent yield of 34.1%. A total mass of 0.71 mg was recovered from the test apparatus and substrate, for a total recovery of 83.5%.

Example 190

Estradiol-17-acetate (MW 314, oral dose 2 mg), a hormonal pro-drug, was coated on a piece of aluminum foil (20 cm$^2$) according to Method C. The calculated thickness of the drug film was 0.9 μm. The substrate was heated as described in Method C at 60 V for 6 seconds. The purity of the drug-aerosol particles was determined to be 98.6%. 0.59 mg was recovered from the glass tube walls after vaporization, for a percent yield of 34.7%.

Example 191

Estradiol 17-heptanoate (MW 384 melting point 94° C., oral dose 1 mg), a hormone, was coated on a metal substrate (50 cm$^2$). 42 mg was applied to the substrate, for a calculated drug film thickness of 8.4 μm and heated according to Method F at 300° C. to form drug-aerosol particles. Purity of the drug-aerosol particles was determined to be 90% by GC analysis. The total mass recovered was 11.9%.

Example 192

Fluphenazine (MW 438, melting point <25° C., oral dose 1 mg), a psychotherapeutic agent, was coated on a piece of aluminum foil (20 cm$^2$) according to Method C. The calculated thickness of the drug film was 1.1 μm. The substrate was heated as described in Method C at 90 V for 3.5 seconds. The purity of the drug-aerosol particles was determined to be 93%. 0.7 mg was recovered from the glass tube walls after vaporization, for a percent yield of 33.3%.

The fluphenazine 2HCl salt form of the drug (MW 510, melting point 237° C.) was also tested. The drug was coated on a metal substrate (10 cm$^2$) according to Method D. The calculated thickness of the drug film was 0.8 μm. The substrate was heated as described in Method D by charging the capacitors to 20.5 V. The purity of the drug-aerosol particles was determined to be 80.7%. 0.333 mg was recovered from the filter after vaporization, for a percent yield of 42.6%. A total mass of 0.521 mg was recovered from the test apparatus and substrate, for a total recovery of 66.7%.

Example 193

Flurazepam (MW 388, melting point 82° C., oral dose 15 mg), sedative and hypnotic, was coated on a piece of aluminum foil (20 cm$^2$) according to Method C. The calculated thickness of the drug film was 2.5 μm. The substrate was heated as described in Method C at 60 V for 6 seconds. The purity of the drug-aerosol particles was determined to be 99.2%. 1.8 mg was recovered from the glass tube walls after vaporization, for a percent yield of 36%.

Flurazepam was further coated on an aluminum foil substrate (24 cm$^2$) according to Method C. 5 mg of the drug was applied to the substrate, for a calculated thickness of the drug film of 2.08 μm. The substrate was heated substantially as described in Method C at 60 V for 5 seconds. The purity of the drug-aerosol particles was determined to be 99.6%. The percent yield of the aerosol was 36%.

Example 194

Flurbiprofen (MW 244, melting point 111° C., oral dose 50 mg), an analgesic, was coated on a piece of aluminum foil (20 cm$^2$) according to Method C. The calculated thickness of the drug film was 4.7 μm. The substrate was heated as described in Method C at 60 V for 5 seconds. The purity of the drug-aerosol particles was determined to be >99.5%. 4.1 mg was recovered from the glass tube walls after vaporization, for a percent yield of 43.6%.

Example 195

Fluvoxamine (MW 318, oral dose 50 mg), a psychotherapeutic agent, was coated on a piece of aluminum foil (20 cm$^2$) according to Method C. The calculated thickness of the drug film was 4.4 μm. The substrate was heated as described in Method C at 90 V for 5 seconds. The purity of the drug-aerosol particles was determined to be 65%. 6.5 mg was recovered from the glass tube walls after vaporization, for a percent yield of 77.8%.

Another substrate containing fluvoxamine coated to a film thickness of 4.4 μm was prepared by the same method and heated under an argon atmosphere at 60 V for 8 seconds. The purity of the drug-aerosol particles was determined to be 88%. 6.9 mg was recovered from the glass tube walls after vaporization, for a percent yield of 78.4%.

Example 196

Frovatriptan (MW 379, melting point 102° C., oral dose 2.5 mg), a migraine preparation, was coated on a piece of aluminum foil (20 cm$^2$) according to Method C. The calculated thickness of the drug film was 3.3 μm. The substrate was heated as described in Method C at 60 V for 12 seconds. The purity of the drug-aerosol particles was determined to be 73%. 1.4 mg was recovered from the glass tube walls after vaporization, for a percent yield of 21.2%.

Frovatriptan was further coated on an aluminum foil substrate (24.5 cm$^2$) according to Method G. 5.0 mg of the drug was applied to the substrate, for a calculated thickness of the drug film of 2.0 μm. The substrate was heated substantially as described in Method G at 90 V for 6 seconds, except that two of the openings of the T-shaped tube were left open and the third connected to the 1 L flask. The purity of the drug-aerosol particles was determined to be >91%. 2.8 mg of the drug was found to have aerosolized by mass lost from substrate, for a percent yield of 56%.

Example 197

Hydroxyzine (MW 375, oral dose 50 mg), an antihistamine, was coated on a piece of aluminum foil (20 cm$^2$) according to Method C. The calculated thickness of the drug film was 14 μm. The substrate was heated as described in Method C at 60 V for 9 seconds. The purity of the drug-aerosol particles was determined to be 93%. 5.54 mg was recovered from the glass tube walls after vaporization, for a percent yield of 19.9%.

The same drug coated on an identical substrate (aluminum foil, 20 cm$^2$) to a calculated drug film thickness of 7.6 μm was heated under an argon atmosphere as described in Method C at 60 V for 9 seconds. Purity of the drug-aerosol particles was determined to be 98.6%. 4.31 mg was recovered from the glass tube walls after vaporization, for a percent yield of 28.5%.

The dihydrochloride salt form of the drug was also tested. Hydroxyzine dihydrochloride (MW 448, melting point 193° C., oral dose 50 mg) was coated on a piece of aluminum foil (20 cm$^2$) according to Method C. The calculated thickness of the drug film was 13.7 µm. The substrate was heated as described in Method C at 60 V for 7 seconds. The purity of the drug-aerosol particles was determined to be 41.2%. 0.25 mg was recovered from the glass tube walls after vaporization, for a percent yield of 0.9%.

The salt form of the drug coated on an identical substrate (aluminum foil, 20 cm$^2$) to a calculated drug film thickness of 12.8 µm was heated under an argon atmosphere as described in Method C at 60 V for 7 seconds. Purity of the drug-aerosol particles was determined to be 70.8%. 1.4 mg was recovered from the glass tube walls after vaporization, for a percent yield of 5.5%.

Example 198

Ibutilide was coated on a stainless steel cylinder (8 cm$^2$) according to Method D. 1.436 mg of drug was applied to the substrate, for a calculated drug film thickness of 1.7 µm. The substrate was heated as described in Method D by charging the capacitors to 20.5 V. The purity of the drug-aerosol particles was determined to be 98.4%. 0.555 mg was recovered from the filter after vaporization, for a percent yield of 38.6%. A total mass of 1.374 mg was recovered from the test apparatus and substrate, for a total recovery of 95.7%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 300 milliseconds. Generation of the thermal vapor was complete by 1200 milliseconds.

Example 199

Indomethacin norcholine ester (MW 429, oral dose 25 mg), an analgesic, was coated on a piece of aluminum foil (20 cm$^2$) according to Method C. The calculated thickness of the drug film was 5.1 µm. The substrate was heated as described in Method C at 60 V for 7 seconds. The purity of the drug-aerosol particles was determined to be >99.5%. 2.94 mg was recovered from the glass tube walls after vaporization, for a percent yield of 29.1%.

Example 200

Ketorolac (MW 254, melting point 161° C., oral dose 10 mg), an analgesic, was coated on a piece of aluminum foil (20 cm$^2$) according to Method C. The calculated thickness of the drug film was 1.1 µm. The substrate was heated as described in Method C at 60 V for 6 seconds. The purity of the drug-aerosol particles was determined to be 65.7%. 0.73 mg was recovered from the glass tube walls after vaporization, for a percent yield of 33.2%.

Example 201

Ketorolac norcholine ester (MW 326, oral dose 10 mg), was coated on an aluminum foil substrate (20 cm$^2$) according to Method C. 2.70 mg of drug was applied to the substrate, for a calculated thickness of the drug film of 1.4 µm. The substrate was heated as described in Method C at 60 V for 5 seconds. The purity of the drug-aerosol particles was determined to be 98.5%. 1.1 mg was recovered from the glass tube walls after vaporization, for a percent yield of 40.7%.

Example 202

Levodopa (MW 197, melting point 278° C., oral dose 500 mg), an antiparkinsonian agent, was coated on a piece of aluminum foil (20 cm$^2$) according to Method C. The calculated thickness of the drug film was 3.7 µm. The substrate was heated as described in Method C at 45 V for 15 seconds, then at 30 V for 10 seconds. The purity of the drug-aerosol particles was determined to be 60.6%. The percent yield of the aerosol was 7.2%.

Example 203

Melatonin (MW 232, melting point 118° C., oral dose 3 mg), a dietary supplement, was coated on an aluminum foil substrate (20 cm$^2$) according to Method C. 2.0 mg of drug was applied to the substrate, for a calculated thickness of the drug film of 1.0 µm. The substrate was heated as described in Method C at 90 V for 3.5 seconds. The purity of the drug-aerosol particles was determined to be >99.5%. 0.43 mg was recovered from the glass tube walls after vaporization, for a percent yield of 21.5%.

Another substrate containing melatonin coated to a film thickness of 1.1 µm was prepared by the same method and heated under an argon atmosphere at 90 V for 3.5 seconds. The purity of the drug-aerosol particles was determined to be >99.5%. 1.02 mg was recovered from the glass tube walls after vaporization, for a percent yield of 46.4%.

Example 204

Methotrexate (oral dose 2.5 mg) was coated on a stainless steel cylinder (8 cm$^2$) according to Method D. The calculated thickness of the drug film was 1.3 µm. The substrate was heated as described in Method D by charging the capacitors to 20.5 V. The purity of the drug-aerosol particles was determined to be 66.3%. The percent yield of the aerosol was 2.4%.

Example 205

Methysergide (MW 353, melting point 196° C., oral dose 2 mg), a migraine preparation, was coated on a piece of aluminum foil (20 cm$^2$) according to Method C. The calculated thickness of the drug film was 1.0 µm. The substrate was heated as described in Method C at 90 V for 3.5 seconds. The purity of the drug-aerosol particles was determined to be 67.5%. 0.21 mg was recovered from the glass tube walls after vaporization, for a percent yield of 10.5%.

Example 206

Metoclopramide (MW 300, melting point 148° C., oral dose 10 mg), a gastrointestinal agent, was coated on an aluminum foil substrate (20 cm$^2$) according to Method C. 2.0 mg of drug was applied to the substrate, for a calculated thickness of the drug film of 1.0 µm. The substrate was heated as under an argon atmosphere at 90 V for 3.5 seconds. The purity of the drug-aerosol particles was determined to be 99.1%. 0.43 mg was recovered from the glass tube walls after vaporization, for a percent yield of 21.7%.

Example 207

Nabumetone (MW 228, melting point 80° C., oral dose 1000 mg), an analgesic, was coated on a piece of aluminum foil (20 cm²) according to Method C. The calculated thickness of the drug film was 4.9 μm. The substrate was heated as described in Method C at 60 V for 6 seconds. The purity of the drug-aerosol particles was determined to be >99.5%. 4.8 mg was recovered from the glass tube walls after vaporization, for a percent yield of 49%.

Example 208

Naltrexone (MW 341, melting point 170° C., oral dose 25 mg), an antidote, was coated on an aluminum foil substrate (20 cm²) according to Method C. 10.3 mg of drug was applied to the substrate, for a calculated thickness of the drug film of 5.2 μm. The substrate was heated as described in Method C at 90 V for 5 seconds. The purity of the drug-aerosol particles was determined to be 96%. 3.3 mg was recovered from the glass tube walls after vaporization, for a percent yield of 32%.

Naltrexone was coated on an aluminum foil substrate (20 cm²) according to Method C. 1.8 mg of drug was applied to the substrate, for a calculated thickness of the drug film of 0.9 μm. The substrate was heated as described in Method C at 90 V for 3.5 seconds under an argon atmosphere. The purity of the drug-aerosol particles was determined to be 97.4%. 1.0 mg was recovered from the glass tube walls after vaporization, for a percent yield of 55.6%.

Example 209

Nalmefene (MW 339, melting point 190° C., IV dose 0.5 mg), an antidote, was coated on a metal substrate (50 cm²). 7.90 mg of drug was coated on the substrate, to form a calculated film thickness of 1.6 μm, and heated according to Method F to form drug-aerosol particles. Purity of the drug-aerosol particles was determined to be 80%. 2.7 mg was recovered from the glass wool after vaporization, for a percent yield of 34%.

Example 210

Perphenazine (MW 404, melting point 100° C., oral dose 2 mg), a psychotherapeutic agent, was coated on an aluminum foil substrate (20 cm²) according to Method C. 2.1 mg of drug was applied to the substrate, for a calculated thickness of the drug film of 1.1 μm. The substrate was heated as described in Method C at 90 V for 3.5 seconds. The purity of the drug-aerosol particles was determined to be 99.1%. 0.37 mg was recovered from the glass tube walls after vaporization, for a percent yield of 17.6%.

Example 211

Pimozide (MW 462, melting point 218° C., oral dose 10 mg), a psychotherapeutic agent, was coated on a piece of aluminum foil (20 cm²) according to Method C. The calculated thickness of the drug film was 4.9 μm. The substrate was heated as described in Method C at 90 V for 5 seconds. The purity of the drug-aerosol particles was determined to be 79%. The percent yield of the aerosol was 6.5%.

Example 212

Piroxicam (MW 248, melting point 200° C., oral dose 20 mg), a CNS-active steroid was coated on a piece of aluminum foil (20 cm²) according to Method C. The calculated thickness of the drug film was 5.0 μm. The substrate was heated as described in Method C at 60 V for 7 seconds. The purity of the drug-aerosol particles was determined to be 87.7%. 2.74 mg was recovered from the glass tube walls after vaporization, for a percent yield of 27.7%.

Example 213

Pregnanolone (MW 318, melting point 150° C., typical inhalation dose 2 mg), an anesthetic, was coated on a metal substrate (50 cm²). 20.75 mg was coated on the substrate, for a calculated film thickness of 4.2 μm, and heated according to Method F at 300° C. to form drug-aerosol particles. Purity of the drug-aerosol particles was determined to be 87%. 9.96 mg of aerosol particles were collected for a percent yield of 48%).

Example 214

Prochlorperazine 2HCl (MW 446, oral dose 5 mg), a psychotherapeutic agent, was coated on a stainless steel cylinder (8 cm²) according to Method D. 0.653 mg of drug was applied to the substrate, for a calculated drug film thickness of 0.8 μm. The substrate was heated as described in Method D by charging the capacitors to 20.5 V. The purity of the drug-aerosol particles was determined to be 72.4%. 0.24 mg was recovered from the filter after vaporization, for a percent yield of 36.8%. A total mass of 0.457 mg was recovered from the test apparatus and substrate, for a total recovery of 70%.

Example 215

Protriptyline HCl (MW 299, melting point 171° C., oral dose 15 mg), a psychotherapeutic agent, was coated on an aluminum foil substrate (20 cm²) according to Method C. 2.20 mg of drug was applied to the substrate, for a calculated thickness of the drug film of 1.1 μm. The substrate was heated as described in Method C at 90 V for 3.5 seconds. The purity of the drug-aerosol particles was determined to be 99.7%. 0.99 mg was recovered from the glass tube walls after vaporization, for a percent yield of 45.0%.

Example 216

Protriptyline (MW 263, oral dose 15 mg) was coated on an aluminum foil substrate (20 cm²) according to Method C. 5.6 mg of drug was applied to the substrate, for a calculated thickness of the drug film of 2.8 μm. The substrate was heated as described in Method C at 90 V for 3.5 seconds. The purity of the drug-aerosol particles was determined to be 89.8%. 1.4 mg was recovered from the glass tube walls after vaporization, for a percent yield of 25%.

Another substrate containing protriptyline coated to a film thickness of 2.7 μm was prepared by the same method and heated under an argon atmosphere at 90 V for 3.5 seconds. The purity of the drug-aerosol particles was determined to be 90.8%. 1.4 mg was recovered from the glass tube walls after vaporization, for a percent yield of 26.4%.

Example 217

Pyrilamine (MW 285, melting point <25° C., oral dose 25 mg), an antihistamine, was coated on a piece of aluminum foil (20 cm²) according to Method C. The calculated thickness of the drug film was 5.2 μm. The substrate was heated as described in Method C at 60 V for 6 seconds. The purity of the drug-aerosol particles was determined to be 98.4%. 4.3 mg was recovered from the glass tube walls after vaporization, for a percent yield of 41.7%.

Pyrilamine maleate (MW 401, melting point 101° C., oral dose 25 mg), an antihistamine, was coated on a piece of aluminum foil (20 cm$^2$) according to Method C. The calculated thickness of the drug film was 10.8 µm. The substrate was heated as described in Method C at 60 V for 7 seconds. The purity of the drug-aerosol particles was determined to be 93.7%. 10.5 mg was recovered from the glass tube walls after vaporization, for a percent yield of 48.8%.

Example 218

Quinine (MW 324, melting point 177° C., oral dose 260 mg), an anti-infective agent, was coated on a piece of aluminum foil (20 cm$^2$) according to Method C. The calculated thickness of the drug film was 1.1 µm. The substrate was heated as described in Method C at 60 V for 6 seconds. The purity of the drug-aerosol particles was determined to be >99.5%. 0.9 mg was recovered from the glass tube walls after vaporization, for a percent yield of 40.9%.

Example 219

Ramipril (MW 417, melting point 109° C., oral dose 1.25 mg), a cardiovascular agent, was coated on a stainless steel cylinder (8 cm$^2$) and heated to form drug-aerosol particles according to Method D by charging the capacitors to 20.5 V. The purity of the drug-aerosol particles was determined to be 61.5%. 0.27 mg was recovered from the filter after vaporization, for a percent yield of 30%. A total mass of 0.56 mg was recovered from the test apparatus and substrate, for a total recovery of 62.2%.

Example 220

Risperidone (MW 410, melting point 170° C., oral dose 2 mg), a psychotherapeutic agent, was coated on a piece of aluminum foil (20 cm$^2$) according to Method C. The calculated thickness of the drug film was 1.4 µm. The substrate was heated as described in Method C at 90 V for 3.5 seconds. The purity of the drug-aerosol particles was determined to be 79%. The percent yield of the aerosol was 7.9%.

Risperidone was also coated on a stainless steel cylinder (8 cm$^2$). 0.75 mg of drug was manually applied to the substrate, for a calculated drug film thickness of 0.9 µm. The substrate was heated as described in Method D by charging the capacitors to 20.5 V. The purity of the drug-aerosol particles was determined to be 87.3%. The percent yield of aerosol particles was 36.7%. A total mass of 0.44 mg was recovered from the test apparatus and substrate, for a total recovery of 59.5%.

Example 221

Scopolamine (MW 303, melting point <25° C., oral dose 1.5 mg), a gastrointestinal agent, was coated on a metal substrate (50 cm$^2$) according to Method F at 200° C. 37.5 mg of drug was applied to the substrate, for a calculated drug film thickness of 7.5 µm. The substrate was heated according to Method F to form drug-aerosol particles. Purity of the drug-aerosol particles was determined to be 90% by GC analysis. 1.2 mg were recovered for a percent yield of 3.2%.

Example 222

Sotalol (MW 272, oral dose 80 mg), a cardiovascular agent, was coated on a stainless steel cylinder (8 cm$^2$) according to Method D. 1.8 mg of drug was applied to the substrate, for a calculated drug film thickness of 2.3 µm. The substrate was heated as described in Method D by charging the capacitors to 20.5 V. The purity of the drug-aerosol particles was determined to be 96.9%. 0.66 mg was recovered from the filter after vaporization, for a percent yield of 36.7%. A total mass of 1.06 mg was recovered from the test apparatus and substrate, for a total recovery of 58.9%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 90 milliseconds. Generation of the thermal vapor was complete by 500 milliseconds.

Example 223

Sulindac (MW 356, melting point 185° C., oral dose 150 mg), an analgesic, was coated on a piece of aluminum foil (20 cm$^2$) according to Method C. The calculated thickness of the drug film was 4.3 µm. The substrate was heated as described in Method C at 60 V for 8 seconds. The purity of the drug-aerosol particles was determined to be 80.4%. 1.19 mg was recovered from the glass tube walls after vaporization, for a percent yield of 14%.

Example 224

Terfenadine (MW 472, melting point 149° C., oral dose 60 mg), an antihistamine, was coated on a piece of aluminum foil (20 cm$^2$) according to Method C. The calculated thickness of the drug film was 2.5 µm. The substrate was heated as described in Method C at 60 V for 8 seconds. The purity of the drug-aerosol particles was determined to be 75.4%. 0.178 mg was recovered from the glass tube walls after vaporization, for a percent yield of 3.6%.

An identical substrate coated with terfenadine (2.8 µm thick) was heated under an argon atmosphere at 60 V for 8 seconds. The purity of the drug-aerosol particles was determined to be 74.7%. 0.56 mg was recovered from the glass tube walls after vaporization, for a percent yield of 10.2%.

Example 225

Triamcinolone acetonide (MW 434, melting point 294° C., oral dose 0.2 mg), a respiratory agent, was coated on a stainless steel cylinder (6 cm$^2$) according to Method D. 0.2 mg of drug was applied to the substrate, for a calculated drug film thickness of 0.3 µm. The substrate was heated as described in Method D by charging the capacitors to 20.5 V. The purity of the drug-aerosol particles was determined to be 92%. 0.02 mg was recovered from the filter after vaporization, for a percent yield of 10%. A total mass of 0.09 mg was recovered from the test apparatus and substrate, for a total recovery of 45%.

Example 226

Trihexyphenidyl (MW 302, melting point 115° C., oral dose 2 mg), an antiparkinsonian agent, was coated on a piece of aluminum foil (20 cm$^2$) according to Method C. The calculated thickness of the drug film was 1.4 µm. The substrate was heated as described in Method C at 90 V for 3.5 seconds. The purity of the drug-aerosol particles was determined to be 77%. 1.91 mg was recovered from the glass tube walls after vaporization, for a percent yield of 68.2%.

Example 227

Thiothixene (MW 444, melting point 149° C., oral dose 10 mg), a psychotherapeutic agent used as an anti-psychotic, was coated on a piece of aluminum foil (20 cm²) according to Method C. The calculated thickness of the drug film was 1.3 µm. The substrate was heated as described in Method C at 90 V for 3.5 seconds. The purity of the drug-aerosol particles was determined to be 74.0%. 1.25 mg was recovered from the glass tube walls after vaporization, for a percent yield of 48.1%.

Example 228

Telmisartan (MW 515, melting point 263° C., oral dose 40 mg), a cardiovascular agent, was coated on a stainless steel cylinder (8 $cm^2$) according to Method D. 2.73 mg of drug was applied to the substrate, for a calculated drug film thickness of 3.3 μm. The substrate was heated as described in Method D by charging the capacitors to 20.5 V. The purity of the drug-aerosol particles was determined to be 96%. 0.64 mg was recovered from the filter after vaporization, for a percent yield of 23.4%. A total mass of 2.73 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 50 milliseconds after heating was initiated, with the majority of the thermal vapor formed by 400 milliseconds. Generation of the thermal vapor was complete by 1100 milliseconds.

Example 229

Temazepam (MW 301, melting point 121° C., oral dose 7.5 mg), a sedative and hypnotic, was coated on an aluminum foil substrate (20 $cm^2$) according to Method C. 4.50 mg of drug was applied to the substrate, for a calculated thickness of the drug film of 2.3 μm. The substrate was heated as described in Method C at 60 V for 7 seconds. The purity of the drug-aerosol particles was determined to be 97.1%. 1.9 mg was recovered from the glass tube walls after vaporization, for a percent yield of 42.2%.

Example 230

Triamterene (MW 253, melting point 316° C., oral dose 100 mg), a cardiovascular agent, was coated on a stainless steel cylinder (8 $cm^2$) according to Method D. 0.733 mg of drug was applied to the substrate, for a calculated drug film thickness of was 0.9 μm. The substrate was heated as described in Method D by charging the capacitors to 20.5 V. The purity of the drug-aerosol particles was determined to be >99.5%. 0.233 mg was recovered from the filter after vaporization, for a percent yield of 31.8%.

Example 231

Trimipramine (MW 294, melting point 45° C., oral dose 50 mg), a psychotherapeutic agent, was coated on a piece of aluminum foil (20 $cm^2$) according to Method C. The calculated thickness of the drug film was 2.8 μm. The substrate was heated as described in Method C at 90 V for 3.5 seconds. The purity of the drug-aerosol particles was determined to be 99.2%. 2.6 mg was recovered from the glass tube walls after vaporization, for a percent yield of 46.4%.

Example 232

Ziprasidone (MW 413, oral dose 20 mg), an anti-psychotic agent, was coated on a stainless steel cylinder (8 $cm^2$) according to Method D. 0.74 mg of drug was applied to the substrate, for a calculated drug film thickness of 0.9 μm. The substrate was heated as described in Method D by charging the capacitors to 20.5 V. The purity of the drug-aerosol particles was determined to be 87.3%. 0.28 mg was recovered from the filter after vaporization, for a percent yield of 37.8%. A total mass of 0.44 mg was recovered from the test apparatus and substrate, for a total recovery of 59.5%.

Example 233

Zonisamide (MW 212, melting point 163° C., oral dose 75 mg), an anticonvulsant, was coated on a metal substrate and heated to form drug-aerosol particles. The substrate was heated as described in Method C and the purity of the drug-aerosol particles was determined to be 99.7%. The percent yield of the aerosol was 38.3%.

Example 234

A. Preparation of Drug-Coated Stainless Steel Foil Substrate

Strips of clean 302/304 stainless-steel foil (0.0025 cm thick, Thin Metal Sales) having dimensions 1.5 cm by 7.0 cm were dip-coated with a drug solution. The final coated area was 5.1 cm by 1.5 cm on both sides of the foil, for a total area of 15 $cm^2$. Foils were prepared as stated above and then extracted with acetonitrile. The amount of drug was determined from quantitative HPLC analysis. Using the known drug-coated surface area, the thickness was then obtained by:

$$\text{film thickness (cm)}=\text{drug mass (g)}/[\text{drug density (g/cm}^3)\times\text{substrate area (cm}^2)]$$

If the drug density is not known, a value of 1 g/$cm^3$ is assumed. The film thickness in microns is obtained by multiplying the film thickness in cm by 10,000.

After drying, the drug-coated foil was placed into a volatilization chamber constructed of a Delrin® block (the airway) and brass bars, which served as electrodes. The dimensions of the airway were 1.0 high by 5.1 wide by 15.2 cm long. The drug-coated foil was placed into the volatilization chamber such that the drug-coated section was between the two sets of electrodes. After securing the top of the volatilization chamber, the electrodes were connected to three 12V batteries wired in series with a switch controlled by circuit. The circuit was designed to close the switch in pulses so as to resistively heat the foil to a temperature within 50 milliseconds (typically between 320° and 470° C.) and maintain that temperature for up to 3 seconds. The back of the volatilization chamber was connected to a two micron Teflon® filter (Savillex) and filter housing, which were in turn connected to the house vacuum. Sufficient airflow was initiated (typically 30.5 L/min=1.0 m/sec). After the drug had vaporized, airflow was stopped and the Teflon® filter was extracted with acetonitrile. Drug extracted from the filter was analyzed by HPLC UV absorbance at 225 nm using a gradient method aimed at detection of impurities to determine percent purity. Also, the extracted drug was quantified to determine a percent yield, based on the mass of drug initially coated onto the substrate. A percent recovery was determined by quantifying any drug remaining on the substrate, adding this to the quantity of drug recovered in the filter and comparing it to the mass of drug initially coated onto the substrate.

Celecoxib and rizatriptan were tested together according to the method above, by coating a solution of the drug onto a piece of stainless steel foil (15 $cm^2$). Twelve substrates were prepared, with film thicknesses ranging from about 4.4 μm to about 11.4 µm. The substrates were heated as described in the method above to 350° C. Purity of the drug aerosol particles from each substrate was determined. The substrate having a thickness of 4.4 μm was prepared by depositing 0.98 mg of rizatriptan and 5.82 mg of celecoxib. After volatilization of drug this substrate, 0.59 mg of rizatriptan and 4.40 mg of celecoxib were recovered from the filter, for a percent yield of 73.6%. The purity of the aerosol particles was 96.5%.

Example 235

Using a solution of 50 mg sildenafil +10 mg caffeine per mL of solvent (2:1 chloroform:methanol), 0.0025 cm thick stainless steel foils (dimensions of 5.0×6.9 cm) were coated with 4.1 mg of sildenafil and 0.5 mg of caffeine on 45 $cm^2$ of surface area. After drying, a variation of Method B was used. However, instead of a capacitive discharge, a feedback circuit, powered by three 12 V sealed lead acid batteries in series, was used to heat the foil to 425° C. and maintain the temperature for 500 milliseconds. Also, the 1.3×2.6×8.9 cm airway/vaporization chamber of Method B was replaced with a 5.1 by 1.0 by 15.3 cm airway to accommodate the larger foils. The airflow rate was set at 30.5 L/m (1.0 m/s). The generated aerosol was captured in a single Teflon filter, which was extracted with acetonitrile and analyzed on HPLC for purity and mass recovery. The purity of the aerosol was 91.9% by peak area under the curve at 225 nm. The mass recovery in the extracted filter was 2.9 mg sildenafil and 0.5 mg caffeine.

Example 236

A number of other drugs were tested according to one of the above methods (A-G) or a similar method, but exhibited purity less than about 60%. These drugs were not further tested for optimization: amiloride, amiodarone, amoxicillin, beclomethasone, bromocriptine, bufexamac, candesartan, candesartan cilexetil, cetirizine, cortisone, cromolyn, cyclosporin A, dexamethasone, diclofenac, dihydroergotamine, disulfiram, dofetilide, edrophonium chloride, famotidine, fexofenadine, formoterol, furosemide, heparin, ipratropium bromide, irbesartan, labetalol, lansoprazole, lisuride, lorazepam, losartan, methocarbamol, metolazone, modafinil, montelukast, myricetin, nadolol, omeprazole, ondansetron, oxazepam, pheneizine, phentermine, propantheline bromide, quinapril hydrochloride, rabeprazole, raloxifene, rosiglitazone, tolmetin, torsemide, valsartan, and zafirlukast.

Although the invention has been described with respect to particular embodiments, it will be apparent to those skilled in the art that various changes and modifications can be made without departing from the invention.

It is claimed:

1. An article for use in an aerosol device, for producing an aerosol, comprising a heat conductive substrate having a surface with a surface area, and a film comprising a drug composition on the surface, the film having a film thickness, wherein the drug composition and film thickness are selected from the group consisting of the following combinations:

alprazolam, film thickness between 0.1 and 10 μm;
amoxapine, thickness between 2 and 20 μm;
apomorphine HCl, film thickness between 0.1 and 5 μm;
atropine, film thickness between 0.1 and 10 μm;
budesonide, film thickness between 0.05 and 20 μm;
bumetanide film thickness between 0.1 and 5 μm;
buprenorphine, film thickness between 0.05 and 10 μm;
butorphanol, film thickness between 0.1 and 10 μm;
celecoxib, film thickness between 2 and 20 μm;
chlorpheniramine, film thickness between 0.05 and 20 μm;
ciclesonide, film thickness between 0.05 and 5 μm;
clomipramine, film thickness between 1 and 8 μm;
diazepam, film thickness between 0.05 and 20 μm;
diphenhydramine, film thickness between 0.05 and 20 μm;
donepezil, film thickness between 1 and 10 μm;
eletriptan, film thickness between 0.2 and 20 μm;
fentanyl, film thickness between 0.05 and 5 μm;
granisetron, film thickness between 0.05 and 20 μm;
hydromorphone, film thickness between 0.05 and 10 μm;
lorazepam, film thickness between 0.05 and 20 μm;
loxapine, film thickness between 1 and 20 μm;
midazolam, film thickness between 0.05 and 20 μm;
morphine, film thickness between 0.2 and 10 μm;
nalbuphine, film thickness between 0.2 and 5 μm;
naratriptan, film thickness between 0.2 and 5 μm;
olanzapine, film thickness between 1 and 20 μm;
parecoxib, film thickness between 0.5 and 2 μm;
paroxetine, film thickness between 1 and 20 μm;
prochlorperazine, film thickness between 0.1 and 20 μm;
quetiapine, film thickness between 1 and 20 μm;
ropinirole, film thickness between 0.05 and 20 μm;
sertraline, film thickness between 1 and 20 μm;
sibutramine, film thickness between 0.5 and 2 μm;
sildenafil, film thickness between 0.2 and 3 μm;
sumatriptan, film thickness between 0.2 and 6 μm;
tadalafil, film thickness between 0.2 and 5 μm;
valdecoxib, film thickness between 0.5 and 10 μm; and
vardenafil, film thickness between 0.1 and 2 μm;
venlafaxine, film thickness between 2 and 20 μm;
zaleplon, film thickness between 0.05 and 20 μm; and
zolpidem, film thickness between 0.1 and 10 μm;

wherein an aerosol formed by vaporizing the drug composition by heating the substrate and condensing the vaporized drug composition contains 10% by weight or less drug degradation products and at least 50% of the total amount of drug composition in the film, and wherein the substrate surface area is such as to yield an effective human therapeutic dose of the drug aerosol.

2. The article of claim 1, wherein said substrate surface area is between about 0.05-100 $cm^2$.

3. The article of claim 1, wherein said substrate surface is impermeable.

4. The article of claim 1, wherein said substrate comprises a material selected from the group consisting of metals, polymers, ceramics, and glass.

5. The article of claim 4, wherein said material is a metal selected from the group consisting of stainless steel and aluminum.

6. The article of claim 1, wherein said substrate has a contiguous surface area of greater than 1 $mm^2$ and a material density of greater than 0.5 g/cc.

7. The article of claim 1, wherein said aerosol has 5% by weight or less drug degradation products.

8. A method of forming an effective human therapeutic inhalation dose of a drug composition aerosol having 10% or less drug degradation products and an aerosol particle mass median aerodynamic diameter (MMAD) between 0.01 and 3 μm, comprising (a) providing a heat conductive substrate having a surface with a surface area, and a film comprising a drug composition on the surface, the film having a film thickness, wherein the drug composition and film thickness are selected from the group consisting of the following combinations:

alprazolam, film thickness between 0.1 and 10 μm;
amoxapine, thickness between 2 and 20 μm;
apomorphine HCl, film thickness between 0.1 and 5 μm;

atropine, film thickness between 0.1 and 10 µm;
budesonide, film thickness between 0.05 and 20 µm;
bumetanide film thickness between 0.1 and 5 µm;
buprenorphine, film thickness between 0.05 and 10 µm;
butorphanol, film thickness between 0.1 and 10 µm;
celecoxib, film thickness between 2 and 20 µm;
chlorpheniramine, film thickness between 0.05 and 20 µm;
ciclesonide, film thickness between 0.05 and 5 µm;
clomipramine, film thickness between 1 and 8 µm;
diazepam, film thickness between 0.05 and 20 µm;
diphenhydramine, film thickness between 0.05 and 20 µm;
donepezil, film thickness between 1 and 10 µm;
eletriptan, film thickness between 0.2 and 20 µm;
fentanyl, film thickness between 0.05 and 5 µm;
granisetron, film thickness between 0.05 and 20 µm;
hydromorphone, film thickness between 0.05 and 10 µm;
lorazepam, film thickness between 0.05 and 20 µm;
loxapine, film thickness between 1 and 20 µm;
midazolam, film thickness between 0.05 and 20 µm;
morphine, film thickness between 0.2 and 10 µm;
nalbuphine, film thickness between 0.2 and 5 µm;
naratriptan, film thickness between 0.2 and 5 µm;
olanzapine, film thickness between 1 and 20 µm;
parecoxib, film thickness between 0.5 and 2 µm;
paroxetine, film thickness between 1 and 20 µm;
prochlorperazine, film thickness between 0.1 and 20 µm;
quetiapine, film thickness between 1 and 20 µm;
ropinirole, film thickness between 0.05 and 20 µm;
sertraline, film thickness between 1 and 20 µm;
sibutramine, film thickness between 0.5 and 2 µm;
sildenafil, film thickness between 0.2 and 3 µm;
sumatriptan, film thickness between 0.2 and 6 µm;
tadalafil, film thickness between 0.2 and 5 µm;
valdecoxib, film thickness between 0.5 and 10 µm; and
vardenafil, film thickness between 0.1 and 2 µm;
venlafaxine, film thickness between 2 and 20 µm;
zaleplon, film thickness between 0.05 and 20 µm; and
zolpidem, film thickness between 0.1 and 10 µm;

(b) heating the substrate to a temperature between 300° C. and 500° C., thereby vaporizing a at least a portion of the drug composition film, and (c) flowing a gas during said heating across the substrate at a gas flow rate effective to produce a desired size of aerosol particles by condensation.

9. The method according to claim 8, wherein said heating vaporizes the drug composition film on the substrate within a time period of 2 seconds.

10. The method according to claim 9, wherein said heating vaporizes the drug composition film on the substrate within a time period of 0.5 seconds.

11. The method of claim 8, wherein said flowing is at a gas flow rate of between 4 and 50 L/minute.

12. The method of claim 8, wherein the aerosol contains 5% by weight or less drug degradation products.

* * * * *